(12) United States Patent
Vancheri

(10) Patent No.: US 12,409,055 B2
(45) Date of Patent: Sep. 9, 2025

(54) ANTI-BACKSPIN COMPONENT FOR VASCULAR PROSTHESIS DELIVERY DEVICE

(71) Applicant: Bolton Medical, Inc., Sunrise, FL (US)

(72) Inventor: Bryan Vancheri, Sunrise, FL (US)

(73) Assignee: Bolton Medical, Inc., Sunrise, FL (US)

(*) Notice: Subject to any disclaimer, the term of this patent is extended or adjusted under 35 U.S.C. 154(b) by 1157 days.

(21) Appl. No.: 17/200,213

(22) Filed: Mar. 12, 2021

(65) Prior Publication Data

US 2021/0401602 A1 Dec. 30, 2021

Related U.S. Application Data

(60) Provisional application No. 63/043,197, filed on Jun. 24, 2020.

(51) Int. Cl.
*A61F 2/966* (2013.01)
*A61F 2/95* (2013.01)

(52) U.S. Cl.
CPC ............ *A61F 2/966* (2013.01); *A61F 2/9517* (2020.05); *A61F 2002/9505* (2013.01)

(58) Field of Classification Search
CPC .................... A61F 2/966; A61F 2/9517; A61F 2002/9505; A61F 2002/9665
See application file for complete search history.

(56) References Cited

U.S. PATENT DOCUMENTS

| | | |
|---|---|---|
| 3,416,531 A | 12/1968 | Edwards |
| 3,485,234 A | 12/1969 | Stevens |
| 3,502,069 A | 3/1970 | Silverman |
| 3,868,956 A | 3/1975 | Alfidi et al. |
| 4,351,333 A | 9/1982 | Lazarus et al. |
| 4,425,919 A | 1/1984 | Alston, Jr. et al. |
| 4,487,808 A | 12/1984 | Lambert |
| 4,515,593 A | 5/1985 | Norton |
| 4,516,972 A | 5/1985 | Samson |
| 4,534,363 A | 8/1985 | Gold |
| 4,572,186 A | 2/1986 | Gould et al. |
| 4,580,568 A | 4/1986 | Gianturco |
| 4,634,432 A | 1/1987 | Kocak |
| 4,655,771 A | 4/1987 | Wallsten |

(Continued)

FOREIGN PATENT DOCUMENTS

| | | |
|---|---|---|
| CN | 1280475 A | 1/2001 |
| CN | 2451136 Y | 10/2001 |

(Continued)

OTHER PUBLICATIONS

Criado et al., "Early Experience with the TalentTM Stent-Graft System for Endoluminal Repair of Abdominal Aortic Aneurysms," Texas Heart Institute Journal, 27:128-135 (2000).

(Continued)

*Primary Examiner* — Melanie R Tyson
*Assistant Examiner* — Rachel S Highland
(74) *Attorney, Agent, or Firm* — Stephen J. Kenny; Emily H. Yasharpour; Foley Hoag LLP

(57) ABSTRACT

A delivery device prevents longitudinal expansion of an aortic prosthesis under compression by engagement of a clutch with a pin upon release of a handle rotating a gearing mechanism about the pin that advances the aortic prosthesis during endovascular implantation at a surgical site.

12 Claims, 38 Drawing Sheets

(56) References Cited

U.S. PATENT DOCUMENTS

| | | |
|---|---|---|
| 4,665,906 A | 5/1987 | Jervis |
| 4,665,918 A | 5/1987 | Garza et al. |
| 4,705,511 A | 11/1987 | Kocak |
| 4,787,899 A | 11/1988 | Lazarus |
| 4,817,613 A | 4/1989 | Jaraczewski et al. |
| 4,990,151 A | 2/1991 | Wallsten |
| 5,000,745 A | 3/1991 | Guest et al. |
| 5,019,057 A | 5/1991 | Truckai |
| 5,041,126 A | 8/1991 | Gianturco |
| 5,057,092 A | 10/1991 | Webster, Jr. |
| 5,067,957 A | 11/1991 | Jervis |
| 5,104,399 A | 4/1992 | Lazarus |
| 5,123,917 A | 6/1992 | Lee |
| 5,154,701 A | 10/1992 | Cheer et al. |
| 5,158,543 A | 10/1992 | Lazarus |
| 5,176,652 A | 1/1993 | Littrell |
| 5,176,660 A | 1/1993 | Truckai |
| 5,201,757 A | 4/1993 | Heyn et al. |
| 5,254,105 A | 10/1993 | Haaga |
| 5,282,824 A | 2/1994 | Gianturco |
| 5,290,295 A | 3/1994 | Querals et al. |
| 5,292,331 A | 3/1994 | Boneau |
| 5,306,263 A | 4/1994 | Voda |
| 5,324,306 A | 6/1994 | Makower et al. |
| 5,334,164 A | 8/1994 | Guy et al. |
| 5,334,168 A | 8/1994 | Hemmer |
| 5,338,295 A | 8/1994 | Cornelius et al. |
| 5,342,384 A | 8/1994 | Sugarbaker |
| 5,358,493 A | 10/1994 | Schweich, Jr. et al. |
| 5,380,304 A | 1/1995 | Parker |
| 5,387,235 A | 2/1995 | Chuter |
| 5,397,345 A | 3/1995 | Lazarus |
| 5,405,377 A | 4/1995 | Cragg |
| 5,415,664 A | 5/1995 | Pinchuk |
| 5,429,617 A | 7/1995 | Hammersmark et al. |
| 5,433,723 A | 7/1995 | Lindenberg et al. |
| 5,456,713 A | 10/1995 | Chuter |
| 5,458,615 A | 10/1995 | Klemm et al. |
| 5,464,449 A | 11/1995 | Ryan et al. |
| 5,474,563 A | 12/1995 | Myler et al. |
| 5,480,423 A | 1/1996 | Ravenscroft et al. |
| 5,489,295 A | 2/1996 | Piplani et al. |
| 5,507,771 A | 4/1996 | Gianturco |
| 5,514,701 A | 5/1996 | Setoi et al. |
| 5,522,881 A | 6/1996 | Lentz |
| 5,522,882 A | 6/1996 | Gaterud et al. |
| 5,531,715 A | 7/1996 | Engelson et al. |
| 5,533,987 A | 7/1996 | Pray et al. |
| 5,534,007 A | 7/1996 | St. Germain et al. |
| 5,540,712 A | 7/1996 | Kleshinski et al. |
| 5,545,210 A | 8/1996 | Hess et al. |
| 5,549,565 A | 8/1996 | Ryan et al. |
| 5,562,726 A | 10/1996 | Chuter |
| 5,562,728 A | 10/1996 | Lazarus et al. |
| 5,569,218 A | 10/1996 | Berg |
| 5,571,135 A | 11/1996 | Fraser et al. |
| 5,575,816 A | 11/1996 | Rudnick et al. |
| 5,575,817 A | 11/1996 | Martin |
| 5,582,614 A | 12/1996 | Feingold |
| 5,591,194 A | 1/1997 | Berthiaume |
| 5,591,195 A | 1/1997 | Taheri et al. |
| 5,591,230 A | 1/1997 | Horn et al. |
| 5,597,378 A | 1/1997 | Jervis |
| 5,601,568 A | 2/1997 | Chevillon et al. |
| 5,607,442 A | 3/1997 | Fischell et al. |
| 5,609,625 A | 3/1997 | Piplani et al. |
| 5,609,627 A | 3/1997 | Goicoechea et al. |
| 5,613,974 A | 3/1997 | Andreas et al. |
| 5,618,270 A | 4/1997 | Orejola |
| 5,628,754 A | 5/1997 | Shevlin et al. |
| 5,628,783 A | 5/1997 | Quiachon et al. |
| 5,632,763 A | 5/1997 | Glastra |
| 5,639,278 A | 6/1997 | Dereume et al. |
| 5,658,263 A | 8/1997 | Dang et al. |
| 5,662,675 A | 9/1997 | Polanskyj Stockert et al. |
| 5,662,700 A | 9/1997 | Lazarus |
| 5,674,208 A | 10/1997 | Berg et al. |
| 5,676,696 A | 10/1997 | Marcade |
| 5,683,449 A | 11/1997 | Marcade |
| 5,693,084 A | 12/1997 | Chuter |
| 5,693,086 A | 12/1997 | Goicoechea et al. |
| 5,695,517 A | 12/1997 | Marin et al. |
| 5,700,269 A | 12/1997 | Pinchuk et al. |
| 5,707,376 A | 1/1998 | Kavteladze et al. |
| 5,709,703 A | 1/1998 | Lukic et al. |
| 5,713,917 A | 2/1998 | Leonhardt et al. |
| 5,716,365 A | 2/1998 | Goicoechea et al. |
| 5,716,393 A | 2/1998 | Lindenberg et al. |
| 5,720,776 A | 2/1998 | Chuter et al. |
| 5,723,003 A | 3/1998 | Winston et al. |
| 5,730,733 A | 3/1998 | Mortier et al. |
| 5,733,267 A | 3/1998 | Del Toro |
| 5,735,859 A | 4/1998 | Fischell et al. |
| 5,741,327 A | 4/1998 | Frantzen |
| 5,749,921 A | 5/1998 | Lenker et al. |
| 5,755,778 A | 5/1998 | Kleshinski |
| 5,776,142 A | 7/1998 | Gunderson |
| 5,782,811 A | 7/1998 | Samson et al. |
| 5,782,904 A | 7/1998 | White et al. |
| 5,782,909 A | 7/1998 | Quiachon et al. |
| 5,788,707 A | 8/1998 | Del Toro et al. |
| 5,792,144 A | 8/1998 | Fischell et al. |
| 5,800,515 A | 9/1998 | Nadal et al. |
| 5,800,517 A | 9/1998 | Anderson et al. |
| 5,800,520 A | 9/1998 | Fogarty et al. |
| 5,807,405 A | 9/1998 | Vanney et al. |
| 5,824,036 A | 10/1998 | Lauterjung |
| 5,824,037 A | 10/1998 | Fogarty et al. |
| 5,824,039 A | 10/1998 | Piplani et al. |
| 5,824,040 A | 10/1998 | Cox et al. |
| 5,824,041 A | 10/1998 | Lenker et al. |
| 5,824,042 A | 10/1998 | Lombardi et al. |
| 5,824,044 A | 10/1998 | Quiachon et al. |
| 5,843,160 A | 12/1998 | Rhodes |
| 5,843,164 A | 12/1998 | Frantzen et al. |
| 5,843,167 A | 12/1998 | Dwyer et al. |
| 5,851,228 A | 12/1998 | Pinheiro |
| 5,860,998 A | 1/1999 | Robinson et al. |
| 5,871,536 A | 2/1999 | Lazarus |
| 5,891,110 A | 4/1999 | Larson et al. |
| 5,891,114 A | 4/1999 | Chien et al. |
| 5,893,868 A | 4/1999 | Hanson et al. |
| 5,899,892 A | 5/1999 | Mortier et al. |
| 5,902,334 A | 5/1999 | Dwyer et al. |
| 5,904,713 A | 5/1999 | Leschinsky |
| 5,906,619 A | 5/1999 | Olson et al. |
| 5,910,101 A | 6/1999 | Andrews et al. |
| 5,911,715 A | 6/1999 | Berg et al. |
| 5,916,263 A | 6/1999 | Goicoechea et al. |
| 5,938,696 A | 8/1999 | Goicoechea et al. |
| 5,944,726 A | 8/1999 | Blaeser et al. |
| 5,947,939 A | 9/1999 | Mortier et al. |
| 5,951,495 A | 9/1999 | Berg et al. |
| 5,954,651 A | 9/1999 | Berg et al. |
| 5,957,949 A | 9/1999 | Leonhardt et al. |
| 5,961,511 A | 10/1999 | Mortier et al. |
| 5,968,069 A | 10/1999 | Dusbabek et al. |
| 5,984,955 A | 11/1999 | Wisselink |
| 5,993,481 A | 11/1999 | Marcade et al. |
| 6,004,310 A | 12/1999 | Bardsley et al. |
| 6,004,328 A | 12/1999 | Solar |
| 6,004,347 A | 12/1999 | McNamara et al. |
| 6,019,778 A | 2/2000 | Wilson et al. |
| 6,024,763 A | 2/2000 | Lenker et al. |
| 6,039,749 A | 3/2000 | Marin et al. |
| 6,039,758 A | 3/2000 | Quiachon et al. |
| 6,039,759 A | 3/2000 | Carpentier et al. |
| 6,045,557 A | 4/2000 | White et al. |
| 6,051,020 A | 4/2000 | Goicoechea et al. |
| 6,053,943 A | 4/2000 | Edwin et al. |
| 6,063,112 A | 5/2000 | Sgro |
| 6,071,307 A | 6/2000 | Rhee et al. |
| 6,077,297 A | 6/2000 | Robinson et al. |
| 6,099,548 A | 8/2000 | Taheri |

(56) References Cited

U.S. PATENT DOCUMENTS

| | | |
|---|---|---|
| 6,099,558 A | 8/2000 | White et al. |
| 6,099,559 A | 8/2000 | Nolting |
| 6,110,191 A | 8/2000 | Dehdashtian et al. |
| 6,110,198 A | 8/2000 | Fogarty et al. |
| 6,117,167 A | 9/2000 | Goicoechea et al. |
| 6,120,480 A | 9/2000 | Zhang et al. |
| 6,123,723 A | 9/2000 | Konya et al. |
| 6,139,572 A | 10/2000 | Campbell et al. |
| 6,152,944 A | 11/2000 | Holman et al. |
| 6,165,163 A | 12/2000 | Chien et al. |
| 6,165,213 A | 12/2000 | Goicoechea et al. |
| 6,168,616 B1 | 1/2001 | Brown, III |
| 6,168,623 B1 | 1/2001 | Fogarty et al. |
| 6,171,334 B1 | 1/2001 | Cox |
| 6,183,481 B1 | 2/2001 | Lee et al. |
| 6,183,505 B1 | 2/2001 | Mohn, Jr. et al. |
| 6,183,506 B1 | 2/2001 | Penn et al. |
| 6,193,705 B1 | 2/2001 | Mortier et al. |
| 6,200,336 B1 | 3/2001 | Pavcnik et al. |
| 6,200,339 B1 | 3/2001 | Leschinsky et al. |
| 6,203,550 B1 | 3/2001 | Olson |
| 6,203,568 B1 | 3/2001 | Lombardi et al. |
| 6,210,435 B1 | 4/2001 | Piplani et al. |
| 6,212,422 B1 | 4/2001 | Berg et al. |
| 6,213,976 B1 | 4/2001 | Trerotola |
| 6,214,038 B1 | 4/2001 | Piplani et al. |
| 6,221,079 B1 | 4/2001 | Magovern et al. |
| 6,221,102 B1 | 4/2001 | Baker et al. |
| 6,224,609 B1 | 5/2001 | Ressemann et al. |
| 6,228,063 B1 | 5/2001 | Aboul-Hosn |
| 6,231,601 B1 | 5/2001 | Myers et al. |
| 6,238,430 B1 | 5/2001 | Klumb et al. |
| 6,245,052 B1 | 6/2001 | Orth et al. |
| 6,248,112 B1 | 6/2001 | Gambale et al. |
| 6,248,116 B1 | 6/2001 | Chevillon et al. |
| 6,251,132 B1 | 6/2001 | Ravenscroft et al. |
| 6,254,609 B1 | 7/2001 | Vrba et al. |
| 6,267,775 B1 | 7/2001 | Clerc et al. |
| 6,270,521 B1 | 8/2001 | Fischell et al. |
| 6,273,909 B1 | 8/2001 | Kugler et al. |
| 6,280,464 B1 | 8/2001 | Hayashi |
| 6,280,466 B1 | 8/2001 | Kugler et al. |
| 6,280,467 B1 | 8/2001 | Leonhardt |
| 6,285,903 B1 | 9/2001 | Rosenthal et al. |
| 6,287,315 B1 | 9/2001 | Wijeratne et al. |
| 6,302,906 B1 | 10/2001 | Goicoechea et al. |
| 6,302,907 B1 | 10/2001 | Hijlkema |
| 6,306,141 B1 | 10/2001 | Jervis |
| 6,312,458 B1 | 11/2001 | Golds |
| 6,319,275 B1 | 11/2001 | Lashinski et al. |
| 6,319,278 B1 | 11/2001 | Quinn |
| 6,322,585 B1 | 11/2001 | Khosravi et al. |
| 6,334,869 B1 | 1/2002 | Leonhardt et al. |
| 6,338,709 B1 | 1/2002 | Geoffrion et al. |
| 6,342,066 B1 | 1/2002 | Toro et al. |
| 6,344,044 B1 | 2/2002 | Fulkerson et al. |
| 6,344,052 B1 | 2/2002 | Greenan et al. |
| 6,346,118 B1 | 2/2002 | Baker et al. |
| 6,350,277 B1 | 2/2002 | Kocur |
| 6,355,056 B1 | 3/2002 | Pinheiro |
| 6,355,060 B1 | 3/2002 | Lenker et al. |
| 6,368,345 B1 | 4/2002 | Dehdashtian et al. |
| 6,375,675 B2 | 4/2002 | Dehdashtian et al. |
| 6,375,676 B1 | 4/2002 | Cox |
| 6,379,372 B1 | 4/2002 | Dehdashtian et al. |
| 6,389,946 B1 | 5/2002 | Frid |
| 6,395,017 B1 | 5/2002 | Dwyer et al. |
| 6,395,022 B1 | 5/2002 | Piplani et al. |
| 6,398,802 B1 | 6/2002 | Yee |
| 6,402,781 B1 | 6/2002 | Langberg et al. |
| 6,416,542 B1 | 7/2002 | Marcade et al. |
| 6,419,686 B1 | 7/2002 | McLeod et al. |
| 6,425,898 B1 | 7/2002 | Wilson et al. |
| 6,443,979 B1 | 9/2002 | Stalker et al. |
| 6,443,980 B1 | 9/2002 | Wang et al. |
| 6,450,988 B1 | 9/2002 | Bradshaw |
| 6,451,053 B1 | 9/2002 | Dehdashtian et al. |
| 6,454,796 B1 | 9/2002 | Barkman et al. |
| 6,458,867 B1 | 10/2002 | Wang et al. |
| 6,464,684 B1 | 10/2002 | Galdonik |
| 6,464,719 B2 | 10/2002 | Jayaraman |
| 6,464,721 B1 | 10/2002 | Marcade et al. |
| 6,478,818 B1 | 11/2002 | Taheri |
| 6,488,700 B2 | 12/2002 | Klumb et al. |
| 6,503,274 B1 | 1/2003 | Howanec, Jr. et al. |
| 6,505,066 B1 | 1/2003 | Berg et al. |
| 6,514,282 B1 | 2/2003 | Inoue |
| 6,517,571 B1 | 2/2003 | Brauker et al. |
| 6,517,572 B2 | 2/2003 | Kugler et al. |
| 6,517,573 B1 | 2/2003 | Pollock et al. |
| 6,520,951 B1 | 2/2003 | Carrillo, Jr. et al. |
| 6,520,986 B2 | 2/2003 | Martin et al. |
| 6,524,335 B1 | 2/2003 | Hartley et al. |
| 6,524,336 B1 | 2/2003 | Papazolgou et al. |
| 6,533,753 B1 | 3/2003 | Haarstad et al. |
| 6,540,698 B1 | 4/2003 | Ishii |
| 6,540,778 B1 | 4/2003 | Quiachon et al. |
| 6,551,350 B1 | 4/2003 | Thornton et al. |
| 6,562,022 B2 | 5/2003 | Hoste et al. |
| 6,565,596 B1 | 5/2003 | White et al. |
| 6,565,597 B1 | 5/2003 | Fearnot et al. |
| 6,575,994 B1 | 6/2003 | Marin et al. |
| 6,576,007 B2 | 6/2003 | Dehdashtian et al. |
| 6,582,458 B1 | 6/2003 | White et al. |
| 6,582,460 B1 | 6/2003 | Cryer |
| 6,592,526 B1 | 7/2003 | Lenker |
| 6,613,073 B1 | 9/2003 | White et al. |
| 6,616,626 B2 | 9/2003 | Crank et al. |
| 6,620,126 B2 | 9/2003 | Unsworth et al. |
| 6,641,606 B2 | 11/2003 | Ouriel et al. |
| 6,645,242 B1 | 11/2003 | Quinn |
| 6,652,571 B1 | 11/2003 | White et al. |
| 6,652,572 B2 | 11/2003 | Kugler et al. |
| 6,660,033 B1 | 12/2003 | Marcade et al. |
| 6,676,666 B2 | 1/2004 | Vrba et al. |
| 6,682,536 B2 | 1/2004 | Vardi et al. |
| 6,682,537 B2 | 1/2004 | Ouriel et al. |
| 6,682,557 B1 | 1/2004 | Quiachon et al. |
| 6,685,736 B1 | 2/2004 | White et al. |
| 6,689,152 B2 | 2/2004 | Balceta et al. |
| 6,689,158 B1 | 2/2004 | White et al. |
| 6,692,458 B2 | 2/2004 | Forman et al. |
| 6,692,483 B2 | 2/2004 | Vardi et al. |
| 6,692,512 B2 | 2/2004 | Jang |
| 6,695,875 B2 | 2/2004 | Stelter et al. |
| 6,706,033 B1 | 3/2004 | Martinez et al. |
| 6,726,712 B1 | 4/2004 | Raeder-Devens et al. |
| 6,733,519 B2 | 5/2004 | Lashinski et al. |
| 6,733,523 B2 | 5/2004 | Shaolian et al. |
| 6,755,856 B2 | 6/2004 | Fierens et al. |
| 6,761,731 B2 | 7/2004 | Majercak |
| 6,790,222 B2 | 9/2004 | Kugler et al. |
| 6,802,860 B2 | 10/2004 | Cosgrove et al. |
| 6,808,529 B2 | 10/2004 | Fulkerson |
| 6,811,559 B2 | 11/2004 | Thornton |
| 6,814,748 B1 | 11/2004 | Baker et al. |
| 6,821,291 B2 | 11/2004 | Bolea et al. |
| 6,827,710 B1 | 12/2004 | Mooney et al. |
| 6,827,711 B2 | 12/2004 | Sunseri |
| 6,830,575 B2 | 12/2004 | Stenzel et al. |
| 6,843,803 B2 | 1/2005 | Ryan et al. |
| 6,849,084 B2 | 2/2005 | Rabkin et al. |
| 6,849,088 B2 | 2/2005 | Dehdashtian et al. |
| 6,858,034 B1 | 2/2005 | Hijlkema et al. |
| 6,859,986 B2 | 3/2005 | Jackson et al. |
| 6,860,901 B1 | 3/2005 | Baker et al. |
| 6,863,668 B2 | 3/2005 | Gillespie et al. |
| 6,866,660 B2 | 3/2005 | Garabedian et al. |
| 6,871,085 B2 | 3/2005 | Sommer |
| 6,884,260 B2 | 4/2005 | Kugler et al. |
| 6,890,348 B2 | 5/2005 | Sydney et al. |
| 6,911,039 B2 | 6/2005 | Shiu et al. |
| 6,916,335 B2 | 7/2005 | Kanji |
| 6,918,925 B2 | 7/2005 | Tehrani |

(56) References Cited

U.S. PATENT DOCUMENTS

| | | |
|---|---|---|
| 6,932,829 B2 | 8/2005 | Majercak |
| 6,938,646 B2 | 9/2005 | Litton |
| 6,939,371 B2 | 9/2005 | Kugler et al. |
| 6,942,691 B1 | 9/2005 | Chuter |
| 6,945,989 B1 | 9/2005 | Betelia et al. |
| 6,945,990 B2 | 9/2005 | Greenan |
| 6,964,679 B1 | 11/2005 | Marcade et al. |
| 6,974,471 B2 | 12/2005 | Van Schie et al. |
| 6,989,024 B2 | 1/2006 | Hebert et al. |
| 6,994,722 B2 | 2/2006 | DiCarlo |
| 7,001,420 B2 | 2/2006 | Speck et al. |
| 7,011,647 B2 | 3/2006 | Purdy et al. |
| 7,014,653 B2 | 3/2006 | Ouriel et al. |
| 7,025,773 B2 | 4/2006 | Gittings et al. |
| 7,052,511 B2 | 5/2006 | Weldon et al. |
| 7,070,582 B2 | 7/2006 | Freyman et al. |
| 7,105,016 B2 | 9/2006 | Shiu et al. |
| 7,112,217 B1 | 9/2006 | Kugler et al. |
| 7,115,134 B2 | 10/2006 | Chambers |
| 7,125,419 B2 | 10/2006 | Sequin et al. |
| 7,147,657 B2 | 12/2006 | Chiang et al. |
| 7,147,660 B2 | 12/2006 | Chobotov et al. |
| 7,160,318 B2 | 1/2007 | Greenberg et al. |
| 7,163,552 B2 | 1/2007 | Diaz |
| 7,166,125 B1 | 1/2007 | Baker et al. |
| 7,169,170 B2 | 1/2007 | Widenhouse |
| 7,195,639 B2 | 3/2007 | Quiachon et al. |
| 7,225,518 B2 | 6/2007 | Eidenschink et al. |
| 7,238,197 B2 | 7/2007 | Sequin et al. |
| 7,264,632 B2 | 9/2007 | Wright et al. |
| 7,294,147 B2 | 11/2007 | Hartley |
| 7,326,241 B2 | 2/2008 | Jang |
| 7,351,256 B2 | 4/2008 | Hojeibane et al. |
| 7,435,253 B1 | 10/2008 | Hartley et al. |
| 7,451,765 B2 | 11/2008 | Adler |
| 7,530,995 B2 | 5/2009 | Quijano et al. |
| 7,691,090 B2 | 4/2010 | Belley et al. |
| 7,708,771 B2 | 5/2010 | Chuter et al. |
| 7,717,950 B2 | 5/2010 | Greenan |
| 7,722,663 B1 | 5/2010 | Austin |
| 7,763,063 B2 | 7/2010 | Arbefeuille et al. |
| 7,766,962 B1 | 8/2010 | Quinn |
| 7,780,716 B2 | 8/2010 | Pappas et al. |
| 7,794,489 B2 | 9/2010 | Shumer et al. |
| 7,799,065 B2 | 9/2010 | Pappas |
| 7,837,724 B2 | 11/2010 | Keeble et al. |
| 8,007,605 B2 | 8/2011 | Arbefeuille et al. |
| 8,043,354 B2 | 10/2011 | Greenberg et al. |
| 8,062,345 B2 | 11/2011 | Ouellette et al. |
| 8,062,349 B2 | 11/2011 | Moore et al. |
| 8,070,790 B2 | 12/2011 | Berra et al. |
| 8,137,321 B2 | 3/2012 | Argentine |
| 8,206,427 B1 | 6/2012 | Ryan et al. |
| 8,241,346 B2 | 8/2012 | Chobotov |
| 8,292,943 B2 | 10/2012 | Berra et al. |
| 8,333,797 B2 | 12/2012 | Goodson, IV et al. |
| 8,348,988 B2 | 1/2013 | Lad et al. |
| 8,500,792 B2 | 8/2013 | Berra |
| 8,579,963 B2 | 11/2013 | Tabor |
| 8,636,788 B2 | 1/2014 | Arbefeuille et al. |
| 8,641,749 B2 | 2/2014 | Barthold et al. |
| 8,672,992 B2 | 3/2014 | Orr |
| 8,702,787 B2 | 4/2014 | Arbefeuille |
| 8,734,501 B2 | 5/2014 | Hartley et al. |
| 8,740,963 B2 | 6/2014 | Arbefeuille et al. |
| 8,998,970 B2 | 4/2015 | Arbefeuille et al. |
| 9,101,506 B2 | 8/2015 | Arbefeuille et al. |
| 9,198,786 B2 | 12/2015 | Moore et al. |
| 9,220,617 B2 | 12/2015 | Berra |
| 9,237,960 B2 | 1/2016 | Rasmussen et al. |
| 9,364,314 B2 | 6/2016 | Berra et al. |
| 9,408,734 B2 | 8/2016 | Arbefeuille et al. |
| 9,408,735 B2 | 8/2016 | Arbefeuille et al. |
| 9,554,929 B2 * | 1/2017 | Arbefeuille ............ A61F 2/966 |
| 9,592,112 B2 | 3/2017 | Arbefeuille et al. |
| 9,827,123 B2 | 11/2017 | Arbefeuille et al. |
| 9,861,503 B2 | 1/2018 | Barthold et al. |
| 9,877,857 B2 | 1/2018 | Arbefeuille et al. |
| 9,913,743 B2 | 3/2018 | Arbefeuille et al. |
| 9,925,080 B2 | 3/2018 | Arbefeuille et al. |
| 10,292,850 B2 | 5/2019 | Vad et al. |
| 10,299,951 B2 * | 5/2019 | Arbefeuille ............... A61F 2/95 |
| 10,646,365 B2 | 5/2020 | Berra et al. |
| 10,864,097 B2 | 12/2020 | Berra et al. |
| 10,918,509 B2 | 2/2021 | Moore et al. |
| 10,945,827 B2 | 3/2021 | Berra et al. |
| 11,259,945 B2 | 3/2022 | Berra |
| 11,351,049 B2 | 6/2022 | Arbefeuille et al. |
| 11,382,779 B2 | 7/2022 | Berra et al. |
| 11,413,173 B2 | 8/2022 | Arbefeuille et al. |
| 11,596,537 B2 | 3/2023 | Berra et al. |
| 11,666,467 B2 | 6/2023 | White et al. |
| 11,998,469 B2 * | 6/2024 | Arbefeuille ............ A61F 2/966 |
| 2001/0000801 A1 | 5/2001 | Miller et al. |
| 2001/0001833 A1 | 5/2001 | Ravenscroft et al. |
| 2001/0034549 A1 | 10/2001 | Bartholf et al. |
| 2001/0037142 A1 | 11/2001 | Stelter et al. |
| 2001/0049547 A1 | 12/2001 | Moore |
| 2001/0053930 A1 | 12/2001 | Kugler et al. |
| 2002/0007193 A1 | 1/2002 | Tanner et al. |
| 2002/0013617 A1 | 1/2002 | Matsutani et al. |
| 2002/0016597 A1 | 2/2002 | Dwyer et al. |
| 2002/0016627 A1 | 2/2002 | Golds |
| 2002/0035394 A1 | 3/2002 | Fierens et al. |
| 2002/0045929 A1 | 4/2002 | Diaz |
| 2002/0052643 A1 | 5/2002 | Wholey et al. |
| 2002/0052660 A1 | 5/2002 | Greenhalgh |
| 2002/0062133 A1 | 5/2002 | Gilson et al. |
| 2002/0072755 A1 | 6/2002 | Bigus et al. |
| 2002/0082523 A1 | 6/2002 | Kinsella et al. |
| 2002/0082674 A1 | 6/2002 | Anson et al. |
| 2002/0091439 A1 | 7/2002 | Baker et al. |
| 2002/0095140 A1 | 7/2002 | Lootz et al. |
| 2002/0107561 A1 | 8/2002 | Pinheiro |
| 2002/0108621 A1 | 8/2002 | Berg et al. |
| 2002/0111671 A1 | 8/2002 | Stenzel |
| 2002/0138133 A1 | 9/2002 | Lenz et al. |
| 2002/0156518 A1 | 10/2002 | Tehrani |
| 2002/0156522 A1 | 10/2002 | Ivancev et al. |
| 2002/0161424 A1 | 10/2002 | Rapacki et al. |
| 2002/0165554 A1 | 11/2002 | Dworschak et al. |
| 2002/0188344 A1 | 12/2002 | Bolea et al. |
| 2002/0198587 A1 | 12/2002 | Greenberg et al. |
| 2003/0028237 A1 | 2/2003 | Sullivan et al. |
| 2003/0074049 A1 | 4/2003 | Hoganson et al. |
| 2003/0083734 A1 | 5/2003 | Friedrich et al. |
| 2003/0114910 A1 | 6/2003 | Juhani Laakso et al. |
| 2003/0120263 A1 | 6/2003 | Ouriel et al. |
| 2003/0120333 A1 | 6/2003 | Ouriel et al. |
| 2003/0125797 A1 | 7/2003 | Chobotov et al. |
| 2003/0135259 A1 | 7/2003 | Simso |
| 2003/0135269 A1 | 7/2003 | Swanstrom |
| 2003/0139803 A1 | 7/2003 | Sequin et al. |
| 2003/0163193 A1 | 8/2003 | Widenhouse |
| 2003/0176911 A1 | 9/2003 | Iancea et al. |
| 2003/0176912 A1 | 9/2003 | Chuter et al. |
| 2003/0191516 A1 | 10/2003 | Weldon et al. |
| 2003/0195607 A1 | 10/2003 | Trout et al. |
| 2003/0195614 A1 | 10/2003 | Ryan et al. |
| 2003/0199966 A1 | 10/2003 | Shiu et al. |
| 2003/0199967 A1 | 10/2003 | Hartley et al. |
| 2003/0212431 A1 | 11/2003 | Brady et al. |
| 2003/0220682 A1 | 11/2003 | Kujawski |
| 2003/0225445 A1 | 12/2003 | Derus et al. |
| 2003/0233140 A1 | 12/2003 | Hartley et al. |
| 2003/0236564 A1 | 12/2003 | Majercak |
| 2003/0236565 A1 | 12/2003 | DiMatteo et al. |
| 2004/0073284 A1 | 4/2004 | Bates et al. |
| 2004/0073289 A1 | 4/2004 | Hartley |
| 2004/0093063 A1 | 5/2004 | Wright et al. |
| 2004/0098084 A1 | 5/2004 | Hartley et al. |
| 2004/0106974 A1 | 6/2004 | Greenberg et al. |
| 2004/0117003 A1 | 6/2004 | Ouriel et al. |
| 2004/0148007 A1 | 7/2004 | Jackson et al. |

(56) References Cited

U.S. PATENT DOCUMENTS

| | | |
|---|---|---|
| 2004/0148009 A1 | 7/2004 | Buzzard et al. |
| 2004/0193141 A1 | 9/2004 | Leopold et al. |
| 2004/0193244 A1 | 9/2004 | Hartley et al. |
| 2004/0193245 A1 | 9/2004 | Deem et al. |
| 2004/0193252 A1 | 9/2004 | Perez et al. |
| 2004/0199240 A1 | 10/2004 | Dorn |
| 2004/0210194 A1 | 10/2004 | Bonnette et al. |
| 2004/0230284 A1 | 11/2004 | Headley et al. |
| 2004/0230286 A1 | 11/2004 | Moore et al. |
| 2004/0236403 A1 | 11/2004 | Leonhardt et al. |
| 2004/0236407 A1 | 11/2004 | Fierens et al. |
| 2004/0267281 A1 | 12/2004 | Harari et al. |
| 2005/0021125 A1 | 1/2005 | Stack et al. |
| 2005/0027305 A1 | 2/2005 | Shiu et al. |
| 2005/0033406 A1 | 2/2005 | Barnhart et al. |
| 2005/0038495 A1 | 2/2005 | Greenan |
| 2005/0049674 A1 | 3/2005 | Berra et al. |
| 2005/0060016 A1 | 3/2005 | Wu et al. |
| 2005/0080476 A1 | 4/2005 | Gunderson et al. |
| 2005/0080477 A1 | 4/2005 | Sydney et al. |
| 2005/0085789 A1 | 4/2005 | Khan et al. |
| 2005/0096726 A1 | 5/2005 | Sequin et al. |
| 2005/0107862 A1 | 5/2005 | Ohlenschlaeger |
| 2005/0131523 A1 | 6/2005 | Bashiri et al. |
| 2005/0149166 A1 | 7/2005 | Schaeffer et al. |
| 2005/0159804 A1 | 7/2005 | Lad et al. |
| 2005/0171597 A1 | 8/2005 | Boatman et al. |
| 2005/0171598 A1 | 8/2005 | Schaeffer |
| 2005/0177222 A1 | 8/2005 | Mead |
| 2005/0183259 A1 | 8/2005 | Eidenschink et al. |
| 2005/0192659 A1 | 9/2005 | Dahl et al. |
| 2005/0222668 A1 | 10/2005 | Schaeffer et al. |
| 2005/0228484 A1 | 10/2005 | Stephens et al. |
| 2005/0283223 A1 | 12/2005 | Greenan |
| 2005/0288764 A1 | 12/2005 | Snow et al. |
| 2005/0288766 A1 | 12/2005 | Plain et al. |
| 2006/0004433 A1 | 1/2006 | Greenberg et al. |
| 2006/0020320 A1 | 1/2006 | Shaolian et al. |
| 2006/0058864 A1 | 3/2006 | Schaeffer et al. |
| 2006/0127439 A1 | 6/2006 | Mattes et al. |
| 2006/0129169 A1 | 6/2006 | Fogarty et al. |
| 2006/0129224 A1 | 6/2006 | Arbefeuille et al. |
| 2006/0135961 A1 | 6/2006 | Rosenman et al. |
| 2006/0155358 A1 | 7/2006 | LaDuca et al. |
| 2006/0155366 A1 | 7/2006 | LaDuca et al. |
| 2006/0178726 A1 | 8/2006 | Douglas |
| 2006/0195172 A1 | 8/2006 | Luo et al. |
| 2006/0200110 A1 | 9/2006 | Lentz et al. |
| 2006/0212105 A1 | 9/2006 | Dorn et al. |
| 2006/0265047 A1 | 11/2006 | Dorn |
| 2006/0276872 A1 | 12/2006 | Arbefeuille et al. |
| 2006/0282150 A1 | 12/2006 | Olson et al. |
| 2007/0021822 A1 | 1/2007 | Boatman |
| 2007/0048348 A1 | 3/2007 | Atanasoska et al. |
| 2007/0053952 A1 | 3/2007 | Chen et al. |
| 2007/0055240 A1 | 3/2007 | Matthis et al. |
| 2007/0055338 A1 | 3/2007 | Dorn |
| 2007/0055340 A1 | 3/2007 | Pryor |
| 2007/0055341 A1 | 3/2007 | Edoga et al. |
| 2007/0055345 A1 | 3/2007 | Arbefeuille |
| 2007/0055347 A1 | 3/2007 | Arbefeuille |
| 2007/0083252 A1 | 4/2007 | McDonald |
| 2007/0100425 A1 | 5/2007 | Sequin et al. |
| 2007/0123972 A1 | 5/2007 | Greenberg et al. |
| 2007/0135818 A1 | 6/2007 | Moore et al. |
| 2007/0135889 A1 | 6/2007 | Moore et al. |
| 2007/0142894 A1 | 6/2007 | Moore et al. |
| 2007/0156228 A1 | 7/2007 | Majercak et al. |
| 2007/0162109 A1 | 7/2007 | Davila et al. |
| 2007/0163668 A1 | 7/2007 | Arbefeuille et al. |
| 2007/0168014 A1 | 7/2007 | Jimenez et al. |
| 2007/0179592 A1 | 8/2007 | Schaeffer |
| 2007/0179593 A1 | 8/2007 | Fierens et al. |
| 2007/0179601 A1 | 8/2007 | Fierens et al. |
| 2007/0203566 A1 | 8/2007 | Arbefeuille et al. |
| 2007/0207186 A1 | 9/2007 | Scanlon et al. |
| 2007/0213800 A1 | 9/2007 | Fierens et al. |
| 2007/0219620 A1 | 9/2007 | Eells et al. |
| 2007/0244545 A1 | 10/2007 | Birdsall et al. |
| 2007/0255385 A1 | 11/2007 | Tenne et al. |
| 2008/0021538 A1 | 1/2008 | Wright et al. |
| 2008/0027528 A1 | 1/2008 | Jagger et al. |
| 2008/0046065 A1 | 2/2008 | Hartley et al. |
| 2008/0065011 A1 | 3/2008 | Marchand et al. |
| 2008/0071343 A1 | 3/2008 | Mayberry et al. |
| 2008/0082158 A1 | 4/2008 | Tseng et al. |
| 2008/0091260 A1 | 4/2008 | Pomeranz et al. |
| 2008/0114441 A1 | 5/2008 | Rust et al. |
| 2008/0132996 A1 | 6/2008 | Drasler et al. |
| 2008/0172122 A1 | 7/2008 | Mayberry et al. |
| 2008/0195191 A1 | 8/2008 | Luo et al. |
| 2008/0208175 A1 | 8/2008 | Beckman et al. |
| 2008/0262590 A1 | 10/2008 | Murray |
| 2008/0264102 A1 | 10/2008 | Berra |
| 2008/0269865 A1 | 10/2008 | Snow et al. |
| 2009/0163951 A1 | 6/2009 | Simmons et al. |
| 2009/0254165 A1 | 10/2009 | Tabor et al. |
| 2009/0306761 A1 | 12/2009 | Hebert et al. |
| 2010/0030318 A1 | 2/2010 | Berra |
| 2010/0049313 A1 | 2/2010 | Alon et al. |
| 2010/0234932 A1 | 9/2010 | Arbefeuille et al. |
| 2010/0274340 A1 | 10/2010 | Hartley et al. |
| 2011/0071614 A1 | 3/2011 | Majercak et al. |
| 2011/0208288 A1 | 8/2011 | Arbefeuille et al. |
| 2011/0251664 A1 | 10/2011 | Acosta De Acevedo |
| 2011/0307049 A1 | 12/2011 | Kao |
| 2012/0123528 A1 | 5/2012 | Knippel et al. |
| 2012/0130354 A1 | 5/2012 | Valaie |
| 2012/0245672 A1 | 9/2012 | Arbefeuille et al. |
| 2012/0271408 A1 | 10/2012 | Colgan et al. |
| 2012/0296413 A1 | 11/2012 | Arbefeuille et al. |
| 2013/0274856 A1 | 10/2013 | Arbefeuille et al. |
| 2013/0289693 A1 | 10/2013 | Maggard et al. |
| 2013/0325099 A1 | 12/2013 | Berra |
| 2014/0039597 A9 | 2/2014 | Arbefeuille et al. |
| 2014/0135890 A9 | 5/2014 | Berra |
| 2014/0135892 A1 | 5/2014 | Arbefeuille et al. |
| 2014/0135896 A1 | 5/2014 | Arbefeuille et al. |
| 2014/0243952 A1 | 8/2014 | Parodi |
| 2014/0288627 A1 | 9/2014 | Ouellette et al. |
| 2014/0316510 A1 | 10/2014 | Berra |
| 2015/0173922 A1 | 6/2015 | Arbefeuille et al. |
| 2015/0202068 A1 | 7/2015 | Arbefeuille et al. |
| 2015/0272755 A1 | 10/2015 | Arbefeuille et al. |
| 2016/0045350 A1 | 2/2016 | Berra |
| 2016/0081787 A1 | 3/2016 | Parodi et al. |
| 2016/0310301 A1 | 10/2016 | Moore et al. |
| 2017/0100271 A1 | 4/2017 | Arbefeuille et al. |
| 2017/0135807 A1 | 5/2017 | Arbefeuille et al. |
| 2017/0151076 A9 | 6/2017 | Arbefeuille et al. |
| 2017/0165090 A1 | 6/2017 | Arbefeuille et al. |
| 2017/0165091 A1 | 6/2017 | Arbefeuille et al. |
| 2017/0281332 A1 | 10/2017 | Lostetter |
| 2017/0281382 A1 | 10/2017 | Lostetter et al. |
| 2017/0340462 A1 | 11/2017 | Lostetter |
| 2018/0014954 A1 | 1/2018 | Bradway |
| 2018/0049892 A1 | 2/2018 | Henkes et al. |
| 2018/0071123 A1 | 3/2018 | Arbefeuille et al. |
| 2018/0140448 A1 | 5/2018 | Arbefeuille et al. |
| 2018/0206972 A1 | 7/2018 | Arbefeuille et al. |
| 2021/0100669 A1 | 4/2021 | Arbefeuille et al. |
| 2021/0346146 A1 | 11/2021 | Arbefeuille et al. |
| 2022/0257398 A1 | 8/2022 | Arbefeuille et al. |
| 2022/0401241 A1 | 12/2022 | Arbefeuille et al. |
| 2023/0147309 A1 | 5/2023 | Berra et al. |

FOREIGN PATENT DOCUMENTS

| | | |
|---|---|---|
| CN | 101316621 A | 12/2008 |
| CN | 101390743 A | 3/2009 |
| DE | 19753123 A1 | 8/1999 |
| DE | 102006053748 B3 | 4/2008 |
| EP | 0510851 A1 | 10/1992 |
| EP | 0873733 A1 | 10/1998 |

(56) References Cited

FOREIGN PATENT DOCUMENTS

| | | |
|---|---|---|
| EP | 0960607 A1 | 12/1999 |
| EP | 0696447 B1 | 1/2000 |
| EP | 0990426 A1 | 4/2000 |
| EP | 1177779 A2 | 2/2002 |
| EP | 1302178 A2 | 4/2003 |
| EP | 1358903 A2 | 11/2003 |
| EP | 1522277 A2 | 4/2005 |
| EP | 1772120 A2 | 4/2007 |
| EP | 1923024 A2 | 5/2008 |
| EP | 1929979 A2 | 6/2008 |
| EP | 1982677 A2 | 10/2008 |
| EP | 1508313 B1 | 12/2008 |
| FR | 2714816 A1 | 7/1995 |
| FR | 2722678 A1 | 1/1996 |
| FR | 2779939 A1 | 12/1999 |
| JP | 2001/010619 A | 1/2001 |
| JP | 2005/530550 A | 10/2005 |
| WO | WO-91/12838 A1 | 9/1991 |
| WO | WO-94/01149 A1 | 1/1994 |
| WO | WO-95/23008 A1 | 8/1995 |
| WO | WO-96/09013 A1 | 3/1996 |
| WO | WO-96/23455 A1 | 8/1996 |
| WO | WO-96/31174 A1 | 10/1996 |
| WO | WO-96/38101 A1 | 12/1996 |
| WO | WO-97/33532 A2 | 9/1997 |
| WO | WO-98/20811 A1 | 5/1998 |
| WO | WO-98/23242 A2 | 6/1998 |
| WO | WO-98/42276 A1 | 10/1998 |
| WO | WO-99/25273 A1 | 5/1999 |
| WO | WO-99/37242 A1 | 7/1999 |
| WO | WO-99/65420 A1 | 12/1999 |
| WO | WO-00/02615 A1 | 1/2000 |
| WO | WO-00/30562 A1 | 6/2000 |
| WO | WO-01/17602 A1 | 3/2001 |
| WO | WO-01/21102 A1 | 3/2001 |
| WO | WO-02/28316 A2 | 4/2002 |
| WO | WO-03/015662 A1 | 2/2003 |
| WO | WO-2004/000169 A1 | 12/2003 |
| WO | WO-2004/002370 A1 | 1/2004 |
| WO | WO-2004/071352 A1 | 8/2004 |
| WO | WO-2004091452 A1 | 10/2004 |
| WO | WO-2005/023149 A2 | 3/2005 |
| WO | WO-2005/034808 A1 | 4/2005 |
| WO | WO-2005/058409 A1 | 6/2005 |
| WO | WO-2005/067819 A1 | 7/2005 |
| WO | WO-2005/081936 A2 | 9/2005 |
| WO | WO-2005/112821 A2 | 12/2005 |
| WO | WO-2006/088638 A1 | 8/2006 |
| WO | WO-2006/125382 A1 | 11/2006 |
| WO | WO-2007/008533 A1 | 1/2007 |
| WO | WO-2007/028086 A2 | 3/2007 |
| WO | WO-2007/123956 A2 | 11/2007 |
| WO | WO-2008/031103 A2 | 3/2008 |
| WO | WO-2008/098252 A2 | 8/2008 |
| WO | WO-2009/023221 A1 | 2/2009 |
| WO | WO-2009/124124 A1 | 10/2009 |
| WO | WO-2010/042950 A2 | 4/2010 |
| WO | WO-2010/105195 A2 | 9/2010 |
| WO | WO-2013/154749 A1 | 10/2013 |
| WO | WO-2014/149022 A1 | 9/2014 |
| WO | WO-2017/176674 A1 | 10/2017 |
| WO | WO-2021/262264 A1 | 12/2021 |

OTHER PUBLICATIONS

Criado, "EVAR at 20: The Unfolding of a Revolutionary New Technique that Changed Everything," J Endovasc Ther, 17:789-796 (2010).

Parodi et al., "Transfermoral Intraluminal Graft Implantation for Abdominal Aortic Aneurysms," Ann Vasc Surg, 5:491-499 (1991).

International Search Report and Written Opinion for International Application No. PCT/US2021/022134 dated Jul. 5, 2021.

\* cited by examiner

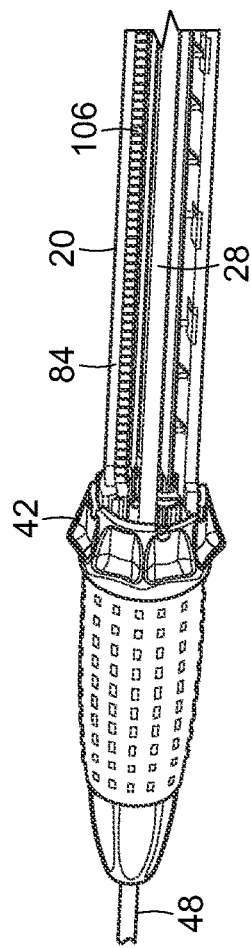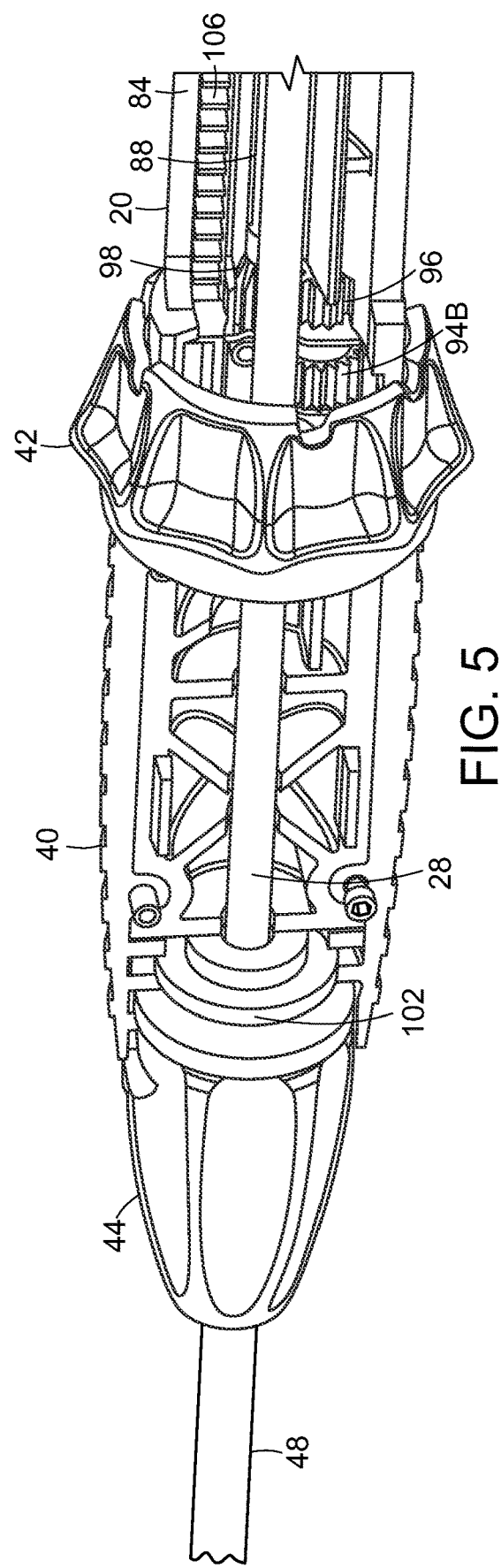

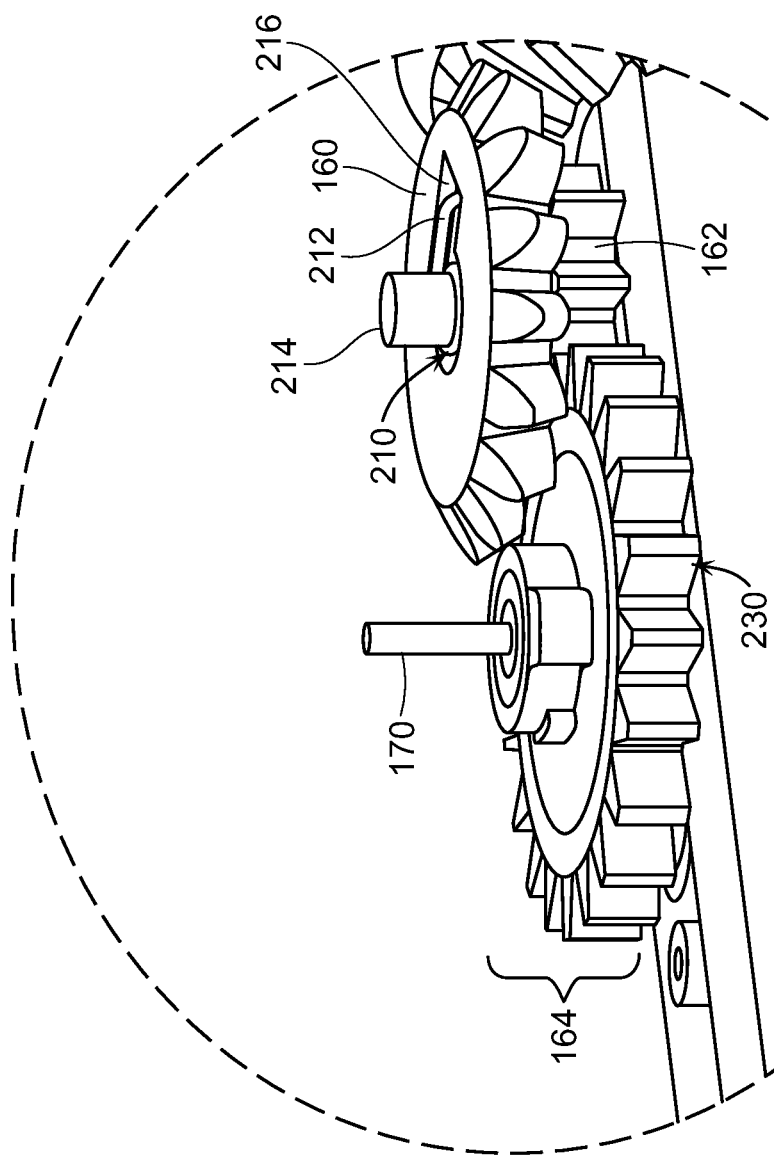

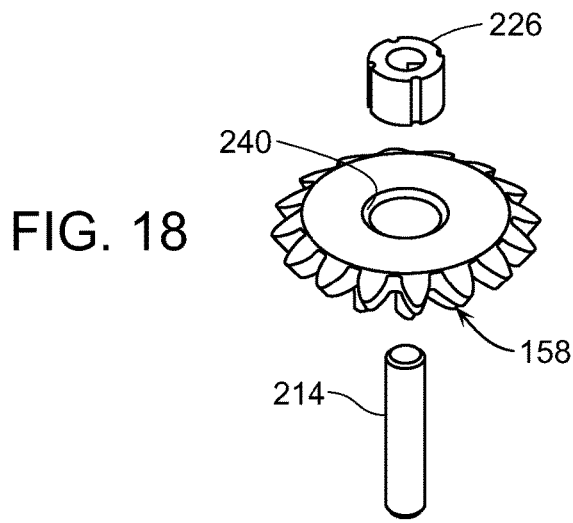
FIG. 18
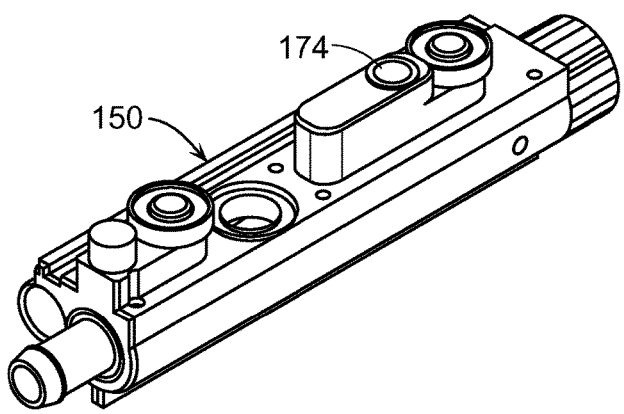
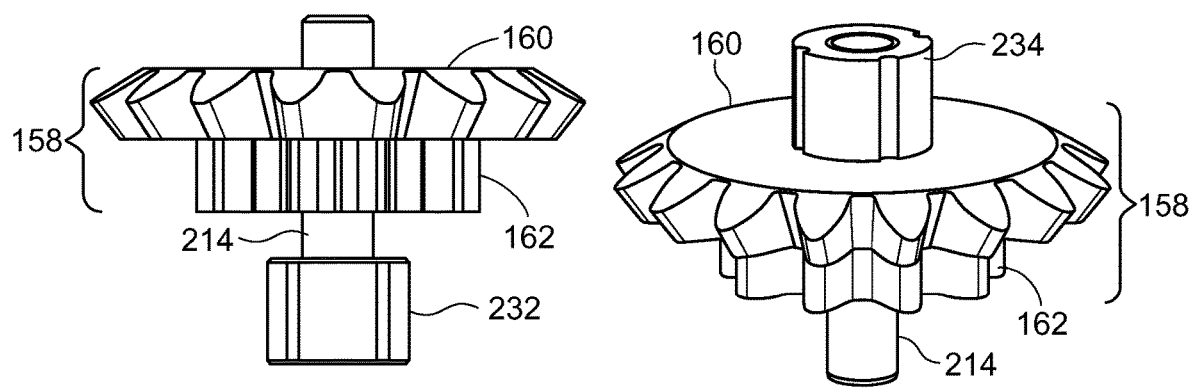
FIG. 19                FIG. 20

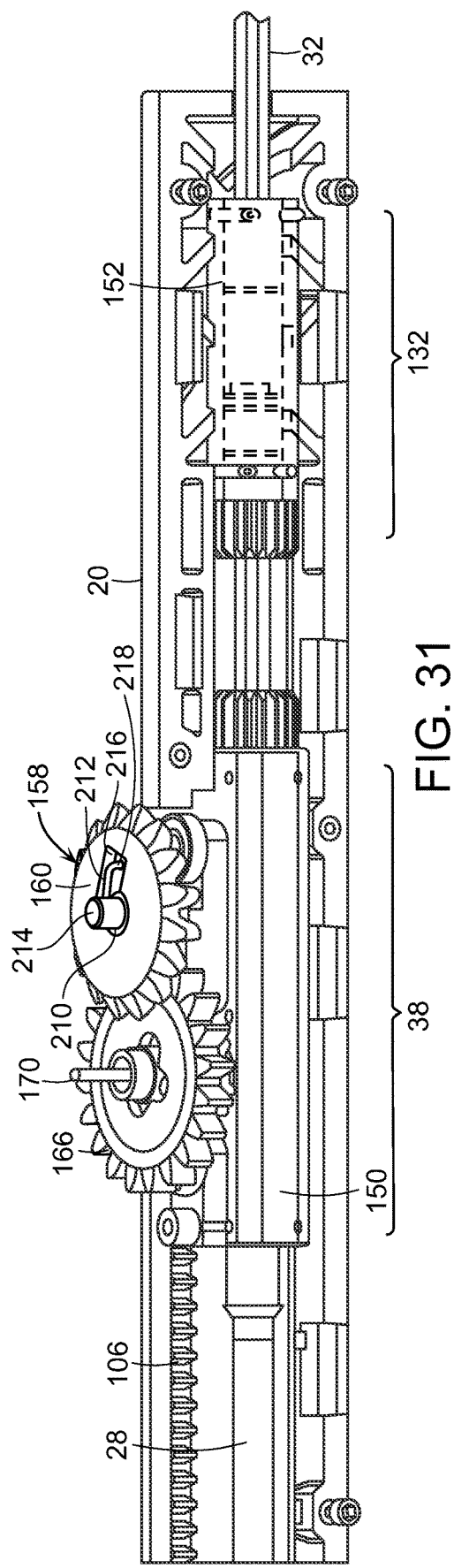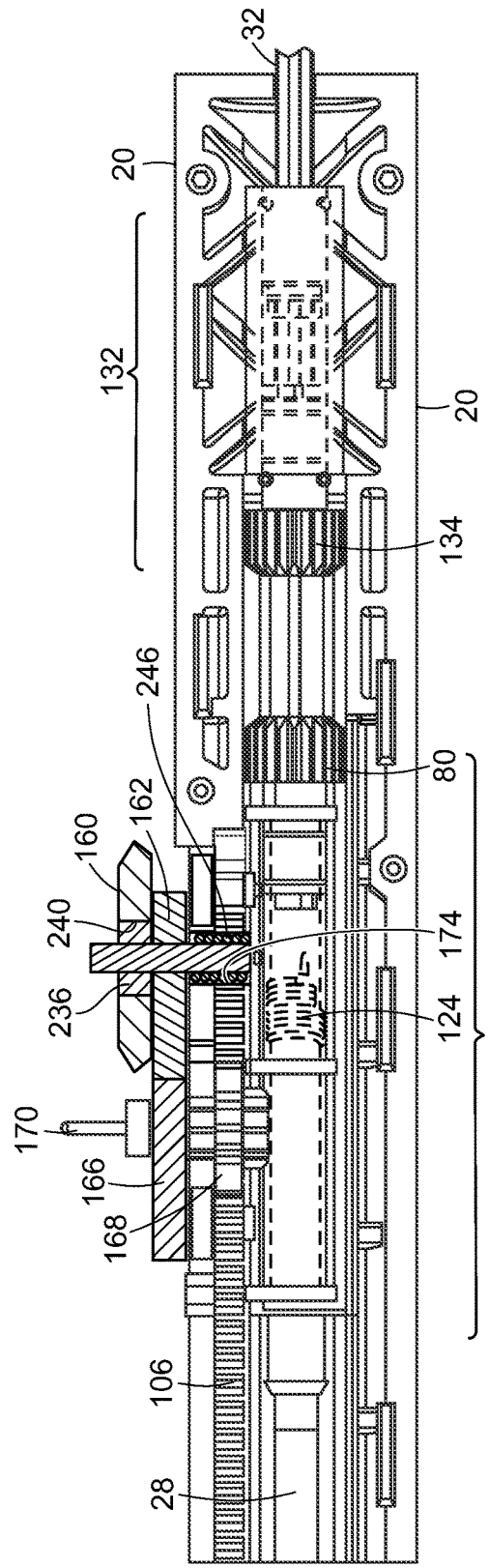

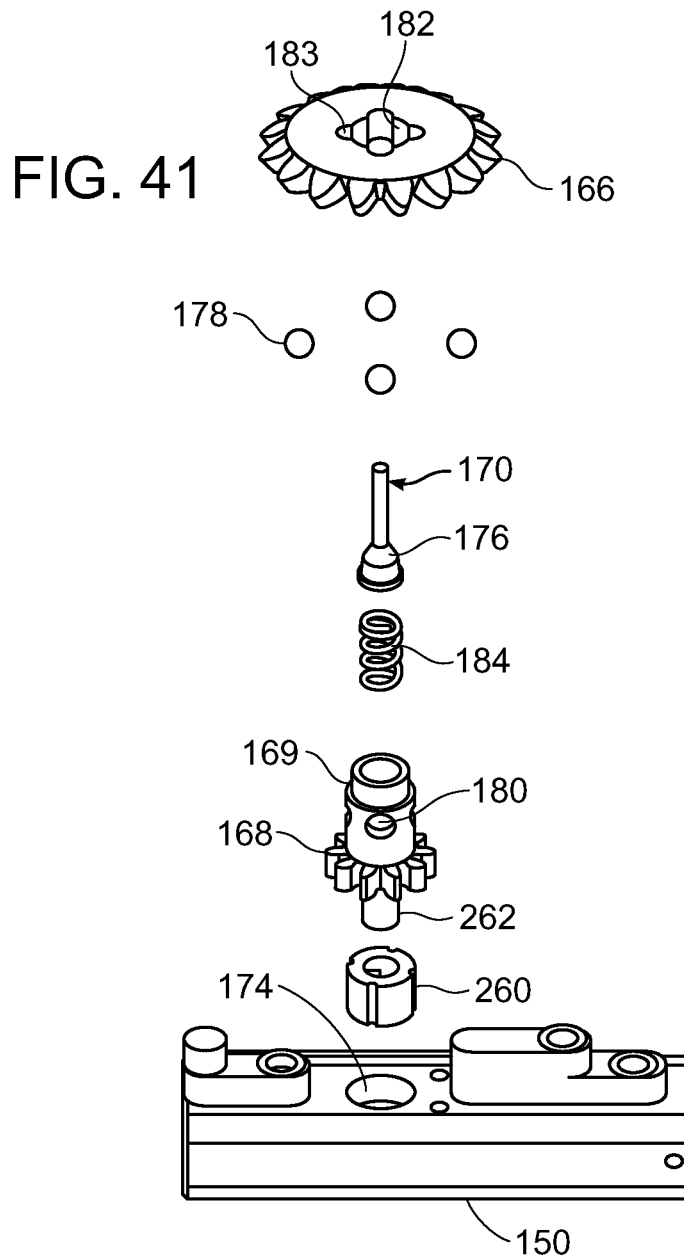

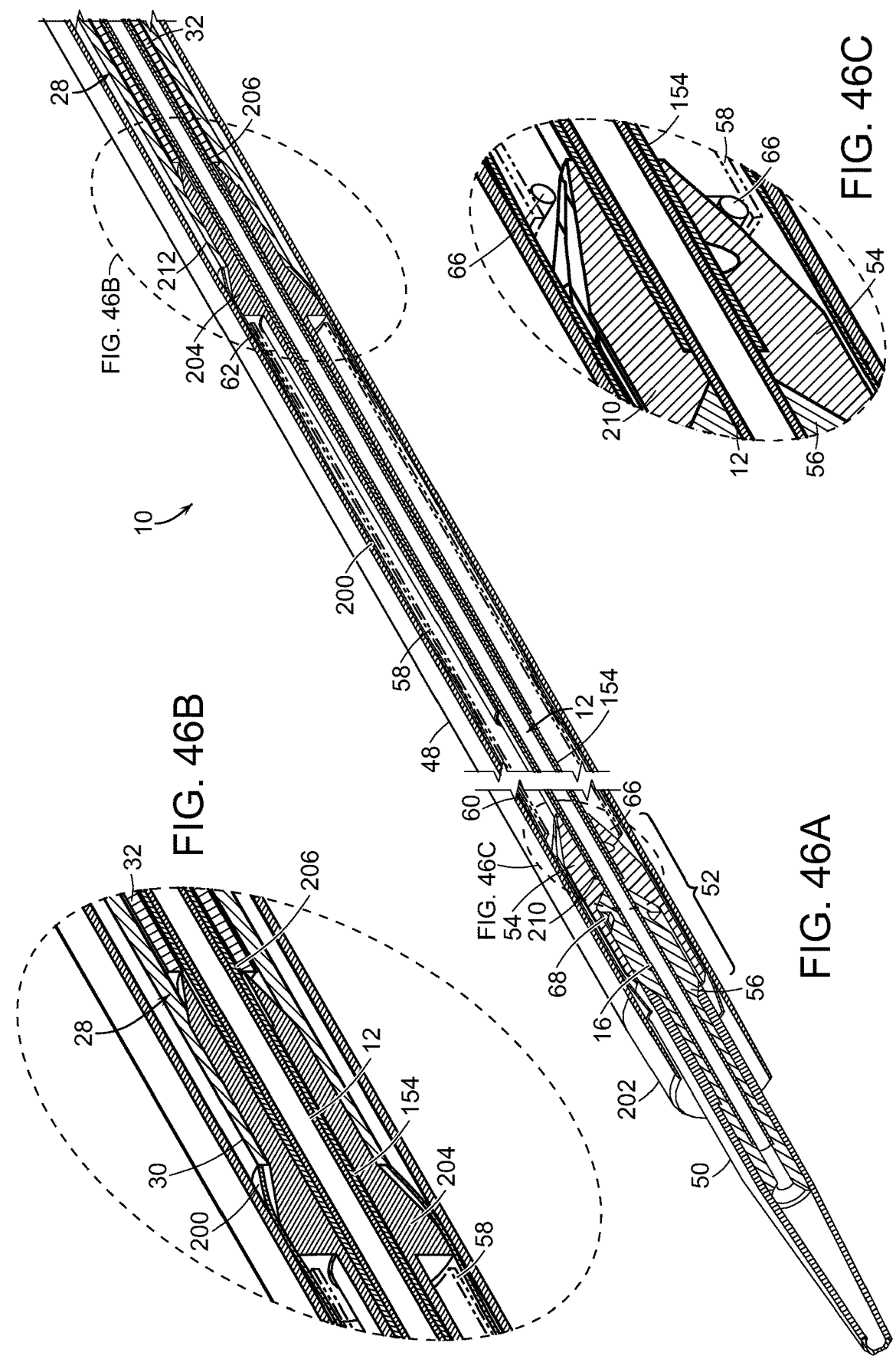

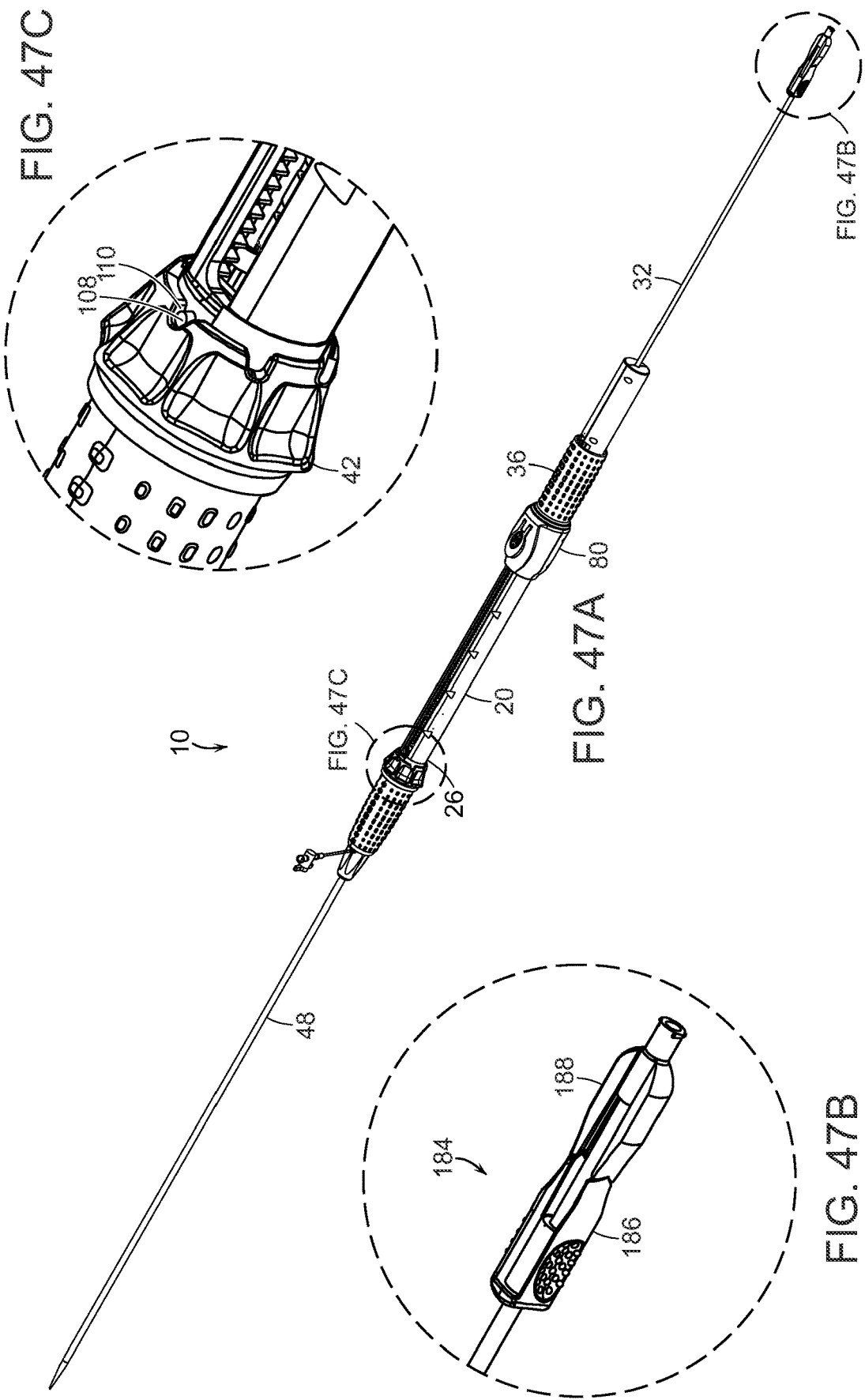

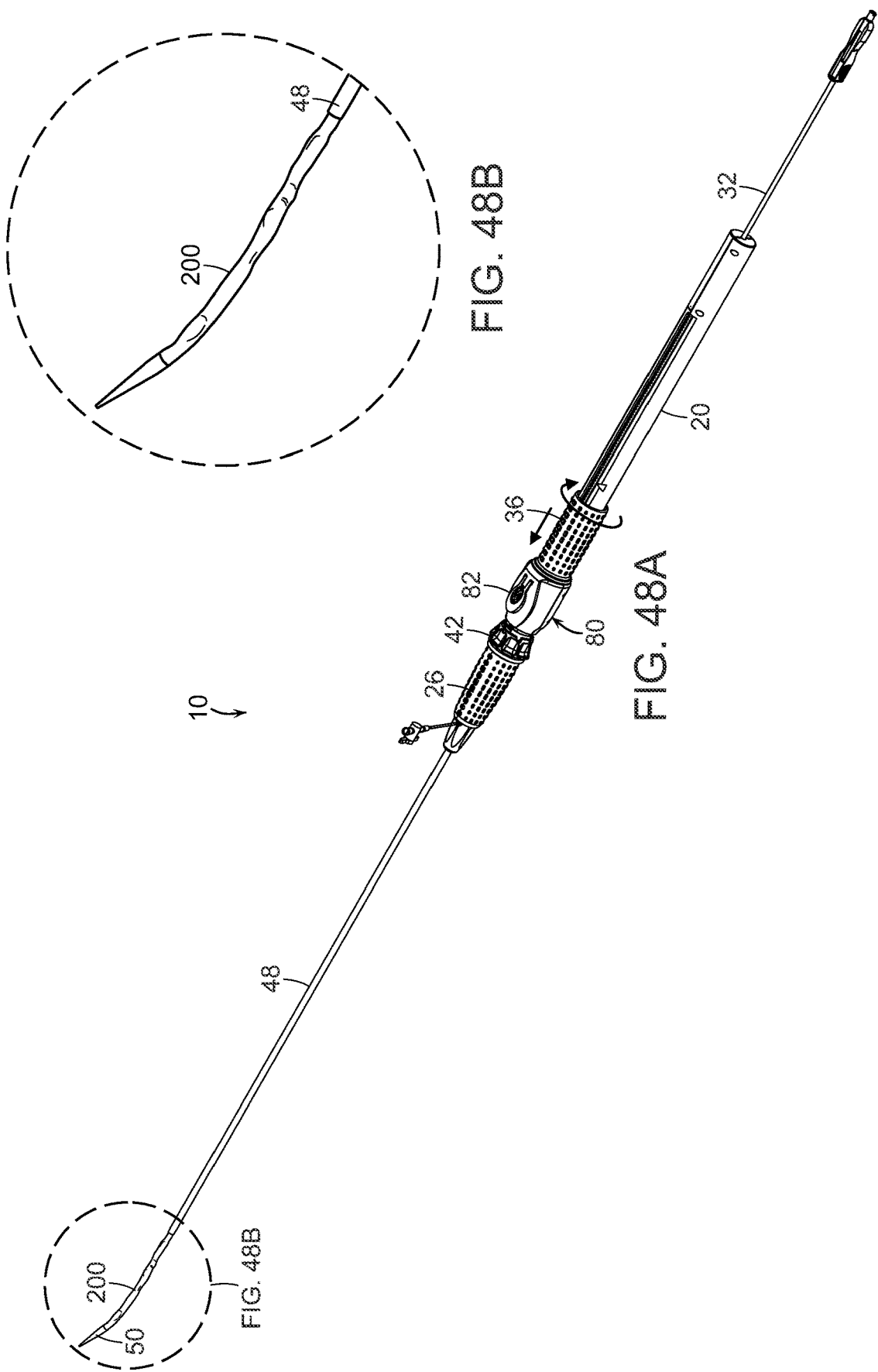

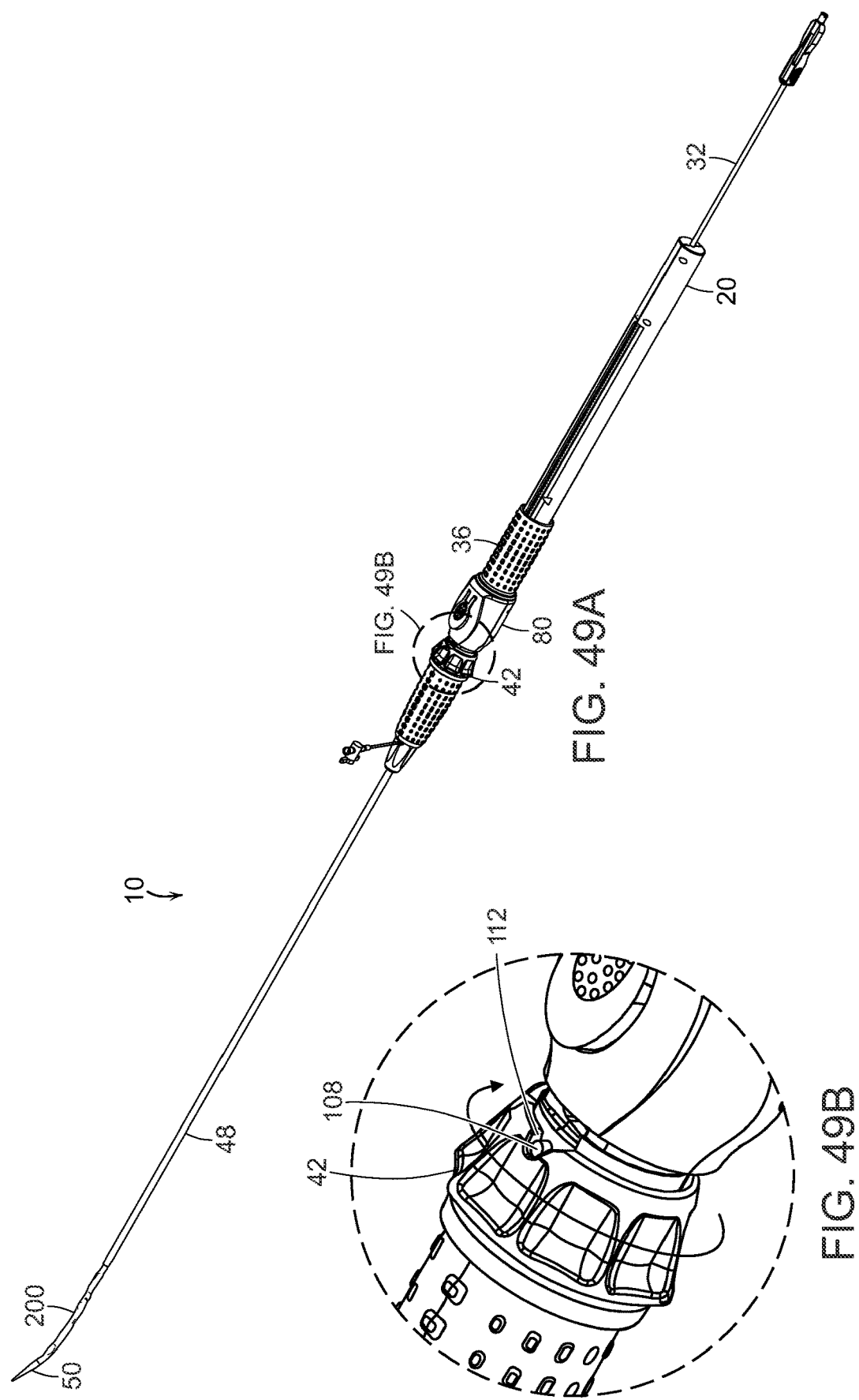

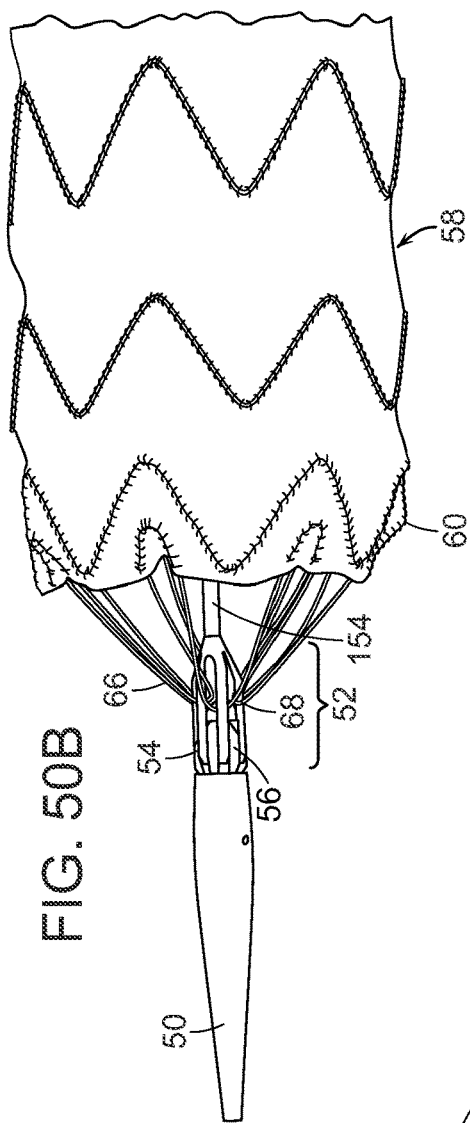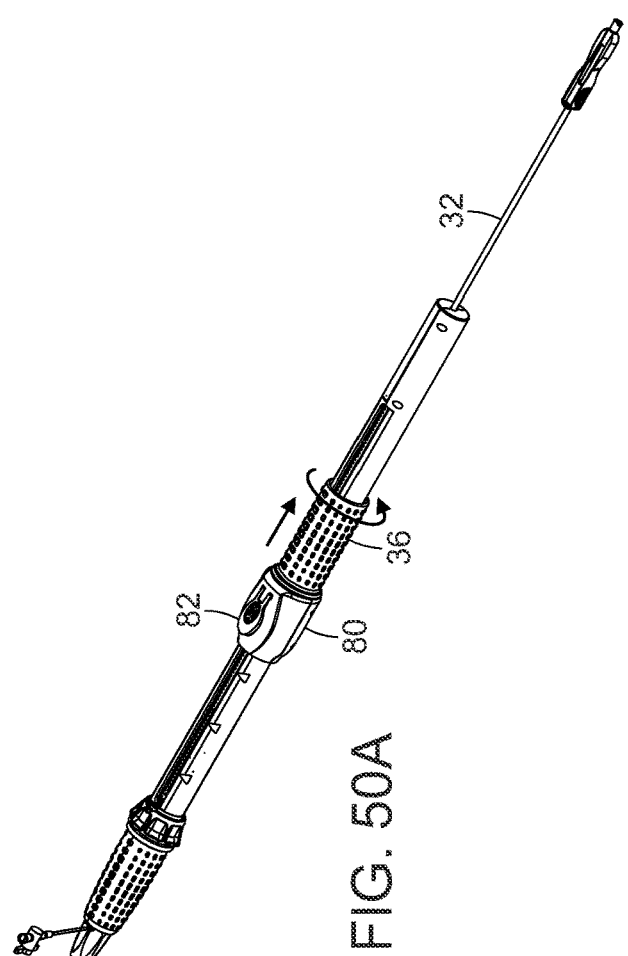

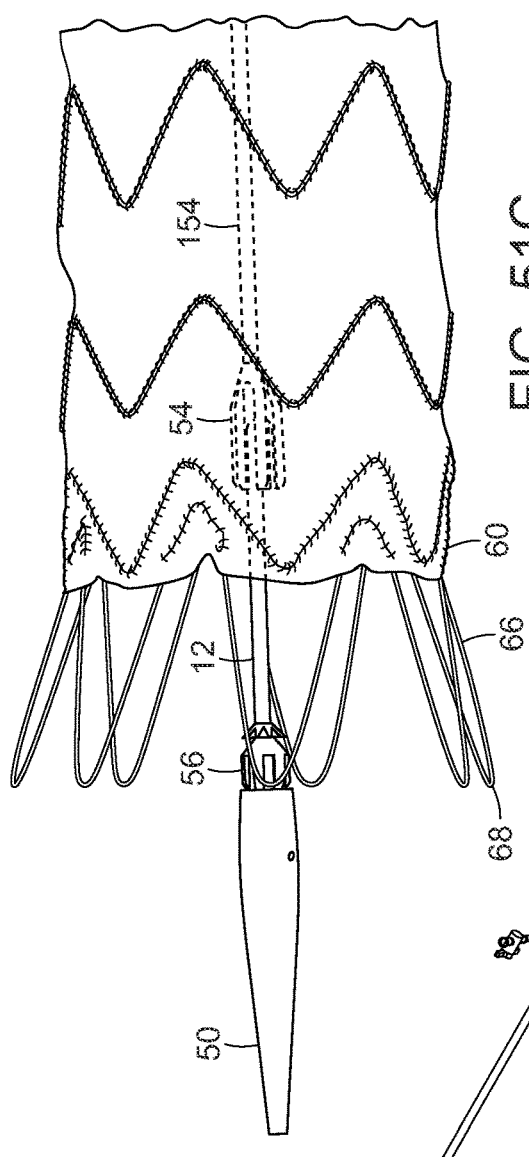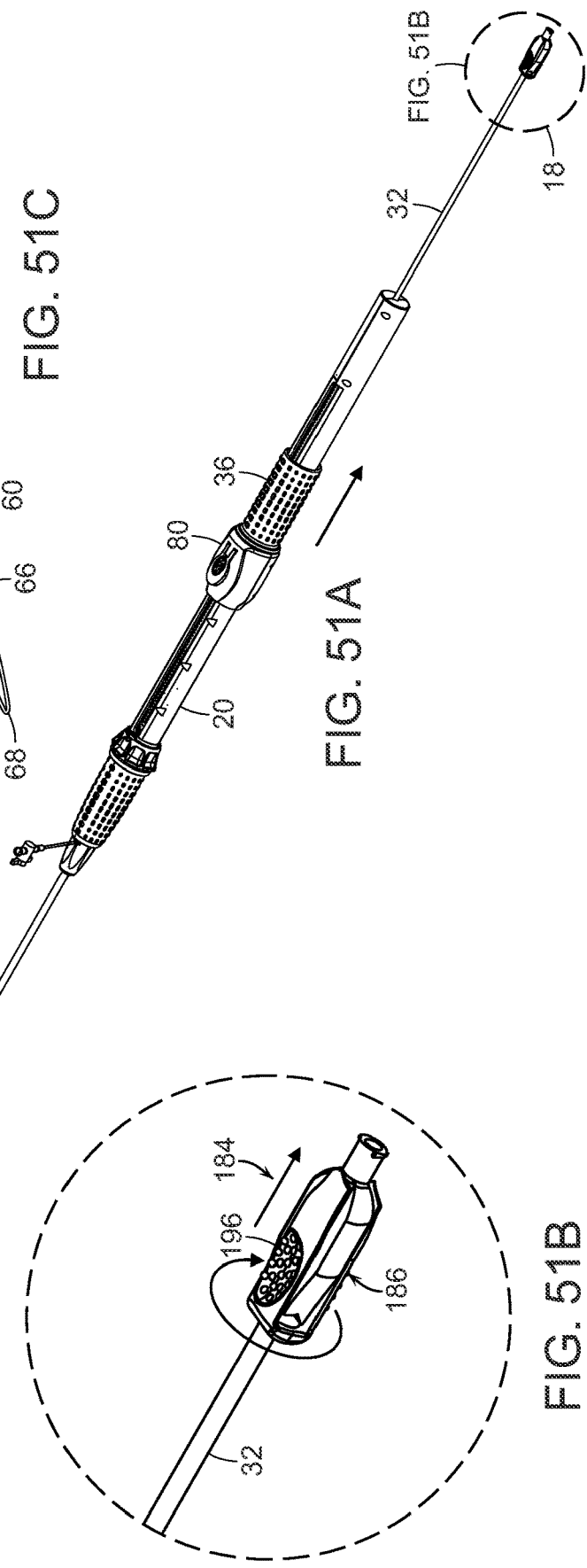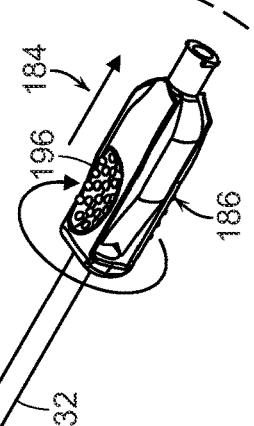

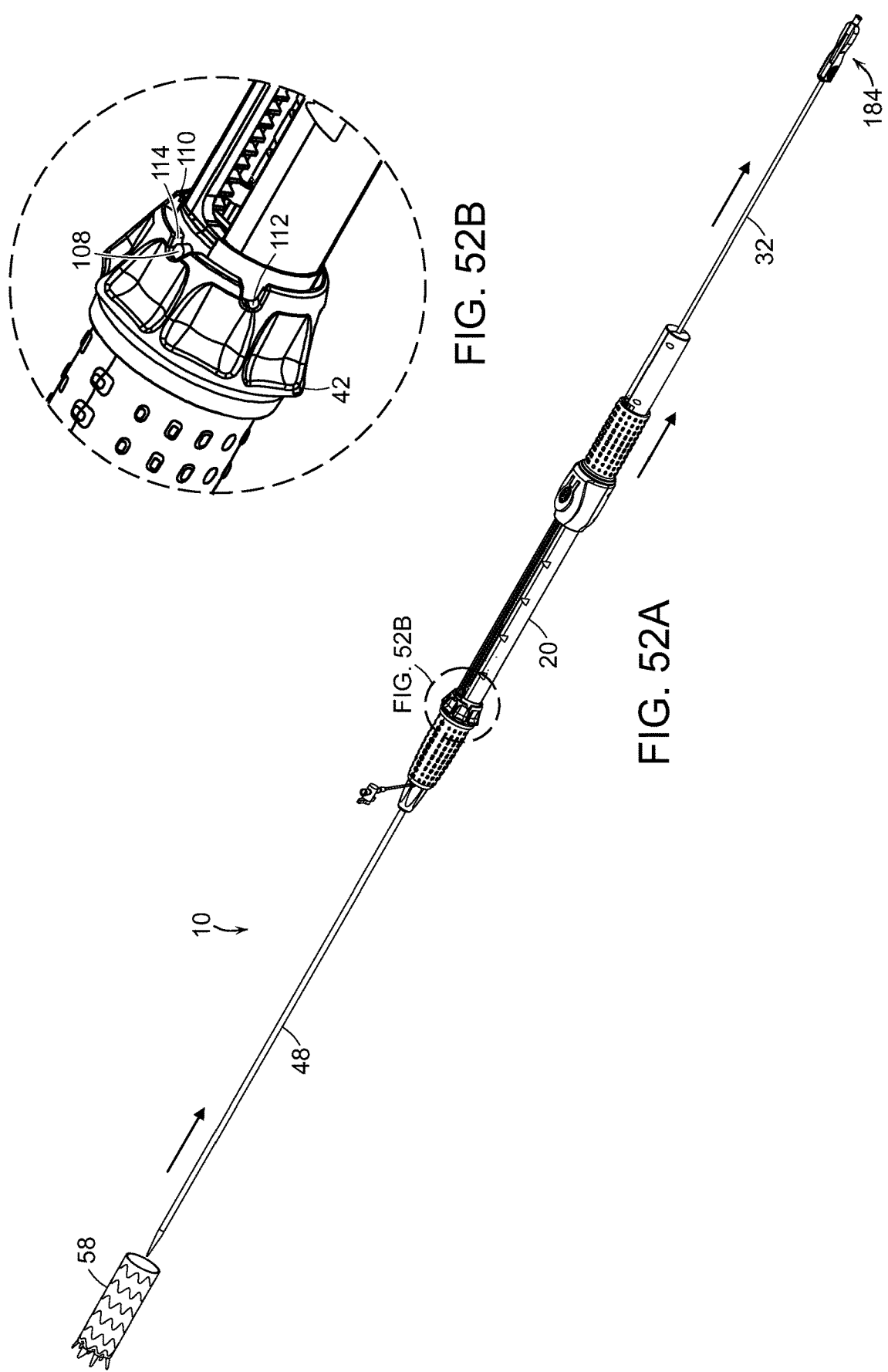

ANTI-BACKSPIN COMPONENT FOR VASCULAR PROSTHESIS DELIVERY DEVICE

RELATED APPLICATION

This application claims the benefit of priority to U.S. Provisional Patent Application No. 63/043,197, filed Jun. 24, 2020, the entire teachings of which are hereby incorporated by reference in their entirety.

BACKGROUND OF THE INVENTION

An aortic aneurysm is an enlargement or bulge in a section of the aorta, which can be life-threatening. Treatment of aortic aneurysms remain a challenge. Endovascular repair has become a viable alternative to open repair of an aortic aneurysm. An endovascular approach results in insertion of an endovascular graft to exclude the aneurysm sac from blood flow. Once in place, the endovascular graft is expanded to create a new path for blood flow. The endovascular graft remains inside the aorta permanently through the use of a metal stent creating a tight fit and seal against the wall of the aorta. Currently, endovascular delivery devices have limitations on the precise control that the physician has in placement of the graft at the site of the aneurysm.

More specifically, endovascular implantation typically relies on delivery devices that employ different combinations of translational forces and mechanical advantage to negotiate vasculature and then to precisely target and deploy endovascular prostheses at a surgical site. During the course of delivery and deployment, endovascular prostheses are exposed to various physical forces that often distort the position of the prostheses within the delivery device. Typically, a primary force that affects disposition of a prosthesis within an endovascular delivery device is longitudinal compression consequent to advancement of the prosthesis from a sheath that radially confines the prostheses until the prosthesis reaches the surgical site where it is to be deployed. Often, advancement is obtained by rotation of a handle by the surgeon about a body of the delivery device. The rotation is translated to longitudinal force along the body of the delivery device by gearing which advances the prosthesis within vasculature of the patient to the surgical site. Once the force advancing the prosthesis stops, the prosthesis will have a tendency to resume its original longitudinal dimension as an opposing force in a direction opposite to that of advancement of the prosthesis (i.e., in a proximal direction back toward the physician). This opposing force will be translated back through the gearing of the delivery device to cause the handle to "backspin" in a direction of rotation opposite to that the surgeon employed to advance the prosthesis when holding the handle. This can present at least three problems for the physician during implantation of the prosthesis. The first is an inability to precisely know the position of the prosthesis at the surgical site. Despite fluoroscopic imagery, if the prosthesis changes position as a consequence of even a momentary release of a handle employed by the surgeon to advance the prosthesis to the surgical site, the surgeon will be uncertain as to how much he needs to advance the handle to continue advancement of the prosthesis, because the prosthesis will reacquire its longitudinally compressed position before advancement of the prosthesis as a whole continues. The second problem is related to the first, and consists of a lack of sensitivity in overall control of the prosthesis during delivery and, most importantly, when landing the prosthesis during deployment and release of the prosthesis from the delivery device, which are portions of the procedure that, generally, are irreversible. The third is the possibility, during advancement of the prosthesis by rotation of the handle, that teeth of gears in the gearing assembly that translates rotation of the handle to longitudinal force can become jammed, freezing the delivery device until the surgeon can momentarily loosen the mesh between the gears, such as by some method that is not part of the method of delivery of the prosthesis. Jamming of the delivery device, and methods, sometimes ad hoc methods, such as shaking the delivery device during implantation of an arterial prosthesis, can be a distraction to the surgeon and the patient, who often is conscious during the procedure, and can endanger the success of the implantation of the prosthesis and the life of the patient.

As a consequence, there is a need to develop new and improved delivery devices to treat aortic aneurysms.

SUMMARY OF THE INVENTION

The invention is generally directed to a delivery device for implanting a vascular prosthesis that effectively prevents backspin of prostheses under longitudinal compression within the delivery device caused by advancement of the prosthesis to a surgical site.

In one embodiment, a delivery device of the invention includes a handle body having a longitudinal axis, a proximal end, and a distal end. A gear rack extends within the handle body and a proximal handle extends about the gear rack and defines teeth. The proximal handle is rotatable about the handle body and the gear rack. A distal handle extends around handle body at the distal end of the handle body, and a guidewire catheter having a proximal end and a distal end extends through the handle body, the proximal handle, and the distal handle along the longitudinal axis of the handle body. A delivery catheter is axially fixed to the proximal handle and has a distal end extending from within the distal end of the handle body and about the guidewire catheter. An outer catheter extends distally from the distal handle and about the delivery catheter when the delivery catheter is in a first, retracted position. A gear assembly links the teeth of the proximal handle to the gear rack, whereby rotation of the proximal handle about the longitudinal axis moves the proximal handle and the delivery catheter along the longitudinal axis relative to the gear rack. A clutch at the gear assembly engages the gear assembly with the proximal handle and thereby biases longitudinal movement of the gear assembly and associated rotation of the proximal handle about the longitudinal axis.

In one particular embodiment, the gear assembly of the delivery device includes a pinion gear assembly that includes an upper pinion gear engaged with the proximal handle, wherein the upper pinion gear defines a non-circular pinion gear orifice that is rotatable about the pinion gear axis. A lower pinion gear in this embodiment is axially aligned with the upper pinion gear and defines a lower pinion gear orifice. The lower pinion gear is engaged with the gear rack and is selectively engaged with the upper pinion gear, wherein the clutch engages lower pinion gear when the gear assembly is directed in a proximal direction. In one particular example of this embodiment, the lower pinion gear includes a lower portion extending toward the longitudinal axis of the handle body, a gear portion engaged with the gear rack, and a pinion gear extension that extends within the upper pinion gear orifice wherein the pinion gear extension defines a lower pinion gear extension orifice. The pinion gear extension further defines a side opening. The side opening and the upper pinion gear orifice together define an interference opening that, when occupied, prevents rotation of the upper pinion gear and the lower pinion gear relative to each other. This embodiment also includes a ball bearing in at least one of each side opening, wherein the ball bearing has a diameter greater than a thickness of a wall defining the side opening. A center pin is movable along the pinion gear axis and within the lower pinion gear orifice. The center pin within the lower pinion gear orifice that includes a frustoconical portion between a base portion having a first diameter and a second diameter that is less than the first diameter, and located in the upper pinion gear orifice, whereby movement of the frustoconical portion of the center pin causes radially outward displacement of the ball bearing into the interference opening, thereby causing an interfering relation between rotation of the upper pinion gear relative to the lower pinion gear. A spring at the lower pinion gear provides bias to the center pin radially outward from the longitudinal axis of handle body, whereby the ball bearing is directed radially outward through the side opening into the interference opening, thereby causing the interfering relation of rotation of the upper pinion gear relative to the lower pinion gear, whereby depressing the center pin removes outward displacement of the ball bearing and eliminates the interfering relation between rotation of the upper pinion gear and a lower pinion gear to cause rotation of the proximal handle to be independent of longitudinal movement of the delivery catheter relative to the handle body along the longitudinal axis.

In another embodiment, the delivery device of the invention includes a handle body having longitudinal axis, a proximal end, and a distal end. A gear rack extends within the handle body, and a proximal handle extends about the gear rack and defines teeth, wherein the proximal handle is rotatable about the handle body and the gear rack. A distal handle extends around handle body at the distal end of the handle body. A guidewire catheter having a proximal end and a distal end extends through the handle body, the proximal handle, the distal handle, and along the longitudinal axis. A delivery catheter is axially fixed to the proximal handle and has a distal end extending from within the distal end of the handle body and about the guide wire catheter. An outer catheter extends distally from the distal handle and about the delivery catheter in a first, retracted position. A gear assembly links teeth of the proximal handle to the gear rack, whereby rotation of the proximal handle about the longitudinal axis moves the proximal handle and the delivery catheter along the longitudinal axis relative to the gear rack. The gear assembly includes a pinion gear assembly engaging the gear rack, and a linking gear assembly that includes an upper linking gear engaging the teeth of the proximal handle and a lower linking gear fixed to the upper linking gear and between the upper linking gear and the longitudinal axis of the handle body, and having teeth engaging the pinion gear assembly. The upper linking gear and the lower linking gear have a common axis of rotation that is normal to the longitudinal axis of the handle body, wherein the upper linking gear in the lower linking gear each define a central opening along the common axis of rotation. A push rod extends about the guide wire catheter and within the delivery catheter, and is fixed to the guidewire catheter at the proximal end and to the guidewire catheter proximal to the handle body, and is selectively fixed to the proximal handle. A locking mechanism assembly extends about the push rod and includes a first locking mechanism that locks the delivery catheter to the push rod when the locking mechanism is in a first locking position, wherein the first locking mechanism defines a first socket and the housing defines a second socket, and wherein the opposite ends of the pin are seated in the first socket and the second socket. A second locking mechanism is fixed to the proximal end of the handle body that locks the push rod to the handle body when the locking mechanism assembly is in a second locking position, wherein the locking function of the first locking position in the second locking position are mutually exclusive. An actuator includes the gear assembly and further includes a housing extending about the handle body, the housing having a proximal end defining a proximal opening and a distal end defining a distal opening, the housing further defining an aperture between the proximal opening and the distal opening. A center pin extends through the central opening of the upper linking gear and the lower linking gear. The pin includes opposite ends that are at the locking mechanism assembly and housing. A clutch engages the gear assembly with the proximal handle and thereby biases longitudinal movement of the gear assembly and associated rotation of the proximal handle about the longitudinal axis, wherein rotation of the proximal handle about the longitudinal axis when the clutch is engaged is resisted by friction between the clutch and at least one of the gear assembly and a portion of the remainder of the delivery device, wherein the clutch engages the pin with the linking gear assembly when the gear assembly is directed in a proximal direction, and wherein rotation of the proximal handle that directs the gear assembly in a proximal direction is resisted by an interfering relationship between the pin and at least one of the first and the second sockets.

In yet another embodiment, the delivery device of the invention includes a handle body having a longitudinal axis, a proximal end, and a distal end, and a gear rack extending within the handle body. A proximal handle extends about the gear rack and defines teeth. The proximal handle is rotatable about the handle body and the gear rack. A distal handle extends around the handle body at the distal end of the handle body and a guidewire catheter has a proximal end and a distal end. The guide wire extends through the handle body, the proximal handle, the distal handle, and along the longitudinal axis. A delivery catheter is axially fixed to the proximal handle and has a distal end extending from within the distal end of the handle body and about the guidewire catheter. An outer catheter extends distally from the distal handle and about the delivery catheter in a first, retracted position. A gear assembly links teeth of the proximal handle to the gear rack, whereby rotation of the proximal handle about the longitudinal axis moves the proximal handle and a delivery catheter along the longitudinal axis relative to the gear rack. The gear assembly includes a pinion gear assembly engaging the gear rack, and a linking gear assembly including an upper linking gear engaging the teeth of the proximal handle and a lower linking gear fixed to the upper linking gear and between the upper linking gear and the longitudinal axis of the handle body, and has teeth engaging the pinion gear assembly. The upper linking gear and the lower linking gear have a common axis of rotation that is normal to the longitudinal axis of the handle body, wherein the upper linking gear in the lower linking gear each define a central opening along the common axis of rotation. A push rod extends about the guidewire catheter and within the delivery catheter, and is fixed to the guidewire catheter at the proximal end of the guidewire catheter proximal to the handle body. The push rod is selectively fixed to the proximal handle. A locking mechanism assembly extends about the push rod and includes a first locking mechanism that locks the delivery catheter to the push rod when the locking mechanism is in a first locking position, and a second locking mechanism fixed to the proximal end of the handle body that locks the push rod to the handle body when the locking mechanism assembly is in a second locking position, wherein the locking function of the first locking position and the second locking position are mutually exclusive. An actuator includes the gear assembly and further includes a housing extending about handle body and has a proximal end defining a proximal opening and a distal end defining a distal opening. The housing further defines an aperture between the proximal opening and the distal opening. A center pin of the actuator extends through the central openings of the upper linking gear and the lower linking gear and includes opposite ends that are at the locking mechanism and the housing. A clutch engages the gear assembly with the proximal handle and thereby biases longitudinal movement of the gear assembly and associated rotation of the proximal handle about the longitudinal axis, wherein rotation of the proximal handle about the longitudinal axis when the clutch is engaged is resisted by friction between the clutch and at least one of the gear assembly and a portion of the remainder of the delivery device, wherein the clutch selectively engages the pin with the linking gear assembly when the gear assembly is directed in a proximal direction. A second clutch engages the linking gear assembly with the pin when the pinion gear assembly is directed distally along the gear rack during engagement of the linking gear assembly with the pinion gear assembly. The second clutch is a coil spring that is fixed at one end to the first locking mechanism and the pin extends through the coil spring, wherein the coil spring is engaged with the pin when the pinion gear assembly is directed distally along the gear rack during engagement of the linking gear assembly with the pinion gear assembly.

In still another embodiment of the invention, a delivery device includes a handle body having a longitudinal axis, a proximal end, and a distal end. A gear rack extends within the handle body and a proximal handle extends about the gear rack and defines teeth. The proximal handle is rotatable about the handle body and the gear rack. A distal handle extends around handle body at the distal end of the handle body. A guidewire catheter has a proximal end and a distal end, and extends through the handle body, the proximal handle, the distal handle, and along the longitudinal axis. A delivery catheter is axially fixed to the proximal handle and has a distal end extending from within the distal end of the handle body and about the guidewire catheter. An outer catheter extends distally from the distal handle and about the delivery catheter in a first, retracted position. A gear assembly links the teeth of the proximal handle to the gear rack, whereby rotation of the proximal handle about the longitudinal axis moves the proximal handle and the delivery catheter along the longitudinal axis relative to the gear rack. The gear assembly includes a pinion gear assembly engaging the gear rack, and a linking gear assembly that includes an upper linking gear engaging the teeth of the proximal handle, and a lower linking gear that is fixed to the upper linking gear and between the upper linking gear and the longitudinal axis of the handle body. The lower linking gear includes teeth engaging the pinion gear assembly. The upper linking gear and the lower linking gear have a common axis of rotation that is normal to the longitudinal axis of the handle body, wherein the upper linking gear and the lower linking gear each define a central opening along the common axis of rotation. A push rod extends about the guidewire catheter and within the delivery catheter, and is fixed into the guidewire catheter at the proximal end of the guidewire catheter proximal to the handle body, and is selectively fixed to the proximal handle. A locking mechanism extends about the push rod and includes a first locking mechanism that locks the delivery catheter to the push rod when the locking mechanism is in a first locking position, and a second locking mechanism fixed to the proximal end of the handle body that locks the push rod to the handle body when the locking mechanism assembly is in a second locking position, wherein the locking function of the first locking position and the second locking position are mutually exclusive. An actuator that includes the gear assembly further includes a housing extending about the handle body. The housing having a proximal end defining a proximal opening and a distal end defining a distal opening, the housing further defining an aperture between the proximal opening in the distal opening. A center pin of the actuator extends through the central openings of the upper linking gear and the lower linking gear, the pin including opposite ends that are at the locking mechanism and the housing. A clutch at the gear assembly engages the gear assembly with the proximal handle and thereby biases longitudinal movement of the gear assembly and associated rotation of the proximal handle about the longitudinal axis, wherein rotation of the proximal handle about the longitudinal axis when the clutch is engaged is resisted by friction between the clutch and at least one of the gear assembly and a portion of the remainder of the delivery device, and wherein the clutch selectively engages the pin with the linking gear assembly when the gear assembly is directed in a proximal direction. A second clutch that engages in linking gear assembly with the pin when the pinion gear assembly is directed distally along the gear rack during engagement of the linking gear assembly with the pinion gear assembly, wherein the second clutch is a coil spring that is fixed at one end into the housing and the pin extends through the coil spring, wherein the coil spring is engaged with the pin when the pinion gear assembly is directed distally along the gear rack during engagement of the linking gear assembly with the pinion gear assembly.

The delivery device and method of its use of the invention have many advantages. For example, longitudinal expansion of a prosthesis after removal of force that advances a prosthesis from a sheath, such as can occur upon release of a handle rotated about a delivery device to control delivery to a surgical site, is minimized or eliminated by a clutch. The clutch engages only when a gear assembly that translates rotational force of a handle and provides mechanical advantage for a surgeon to advance to the prosthesis along a longitudinal axis of the delivery device. The resistance to proximal movement, or longitudinal expansion of the prosthesis, can be overcome, again by mechanical advantage, applied by rotation of the proximal handle by the surgeon in the opposite direction to that of advancement. The resistance can be overcome by, for example, static friction between the clutch and at least one of a pin about which the clutch extends and an interference fit between the clutch or the pin and another component of the delivery device that does not rotate with rotation of the handle or longitudinal advancement of the prosthesis to the delivery site. Selective engagement of the clutch and static friction can thereby provide greater control to the surgeon during advancement of the prosthesis to a surgical site and while targeting landing of the prosthesis at the surgical site prior to deployment and release from the delivery device. The clutch and selective employment of static friction, either separately or in combination, can also reduce the likelihood of interference and jamming of the gears that would otherwise cause the delivery device to seize and interrupt or prevent delivery of the prosthesis altogether.

BRIEF DESCRIPTION OF THE DRAWINGS

FIG. 4 is a perspective view of a shifting knob, distal handle, distal handle nose, and a cross-sectional view, in part, of a handle body and delivery catheter of another embodiment of the invention.

FIG. 5 is a partial cutaway section of the portion of the embodiment of the delivery device of the invention shown in FIG. 4.

FIG. 14A pis an enlarged view, in perspective, of a linking gear assembly associated with the actuator of FIG. 14.

FIG. 18 is an exploded view, in perspective, of a first locking mechanism, a one-way needle roller bearing clutch and pin of another embodiment of a delivery device of the invention.

FIG. 19 is a side view of a linking gear assembly, a pin and a one-way needle roller bearing clutch at a base of a pin, as assembled in another embodiment of the delivery device of the invention.

FIG. 20 is a side view of a linking gear assembly, a pin and a one-way needle roller bearing clutch at a top portion of a pin, as assembled in still another embodiment of the delivery device of the invention.

FIG. 31 is a perspective view of the first locking component housing and the second locking component housing within a cutaway view of the handle body, along with a perspective view of the linking gear assembly and the pinion gear assembly of the actuator.

FIG. 32 is a side view of the representation of the invention, as shown in FIG. 16.

FIG. 41 is an exploded view, in perspective of the pinion gear assembly of FIG. 40, in alignment with a first locking mechanism defining a socket into which the one-way needle roller bearing clutch is seated, such as by a press-fit of the one-way needle roller bearing clutch into the socket.

FIGS. 46A-46C are perspective sectional views of the distal end of the delivery device shown in FIG. 1.

FIG. 47A is a perspective view of the shifting knob in the first position, wherein the push rod is fixed to the proximal handle and the prosthesis is undeployed.

FIG. 47B is a detailed perspective view of proximal clasp assembly in a first position, whereby the apex clasp assembly is unopened.

FIG. 47C is a detailed perspective view of the shifting knob in the first position.

FIG. 48A is a perspective view of the delivery device of FIGS. 47A through 47C showing advancement of the delivery sheath containing the prosthesis when the shifting knob is in a second position, wherein the push rod is fixed to the handle body.

FIG. 48B is a detailed perspective view of advancement of the delivery sheath of FIG. 48A.

FIG. 49A is a perspective view of the delivery device of FIGS. 48A, 48B showing advancement of the delivery sheath.

FIG. 49B is a detailed perspective view of the shifting knob of FIG. 49A in a second position.

FIG. 50A is a perspective view of the delivery device of FIGS. 49A, 49B, wherein the delivery sheath has been partially retracted from the prosthesis.

FIG. 50B is a representation of an apex clasp assembly of one embodiment of the invention in a closed position.

FIG. 51A is a perspective view of the delivery device of FIG. 50A, wherein the apex clasp assembly is opened by actuation of the proximal clasp assembly to thereby release the apices of the proximal stent of the prosthesis shown in FIG. 51C.

FIG. 51B is a representation of the proximal clasp assembly of FIGS. 44, 45, whereby an apex clasp assembly, not shown, has been opened.

FIG. 51C is a representation of the apex clasp assembly of one embodiment of the invention, in an open position.

FIG. 52A is a perspective view of the delivery device of FIG. 51A, wherein the shifting knob has been moved to the third position, whereby the push rod has been released from the proximal handle and the handle body and, wherein the push rod has been retracted from the fully deployed prosthesis.

FIG. 52B is a perspective view of the shifting knob in the third position as shown in FIG. 52A.

DETAILED DESCRIPTION OF THE INVENTION

While this invention has been particularly shown and described with references to example embodiments thereof, it will be understood by those skilled in the art that various changes in form and details may be made therein without departing from the scope of the invention encompassed by the appended claims.

Figure 1:
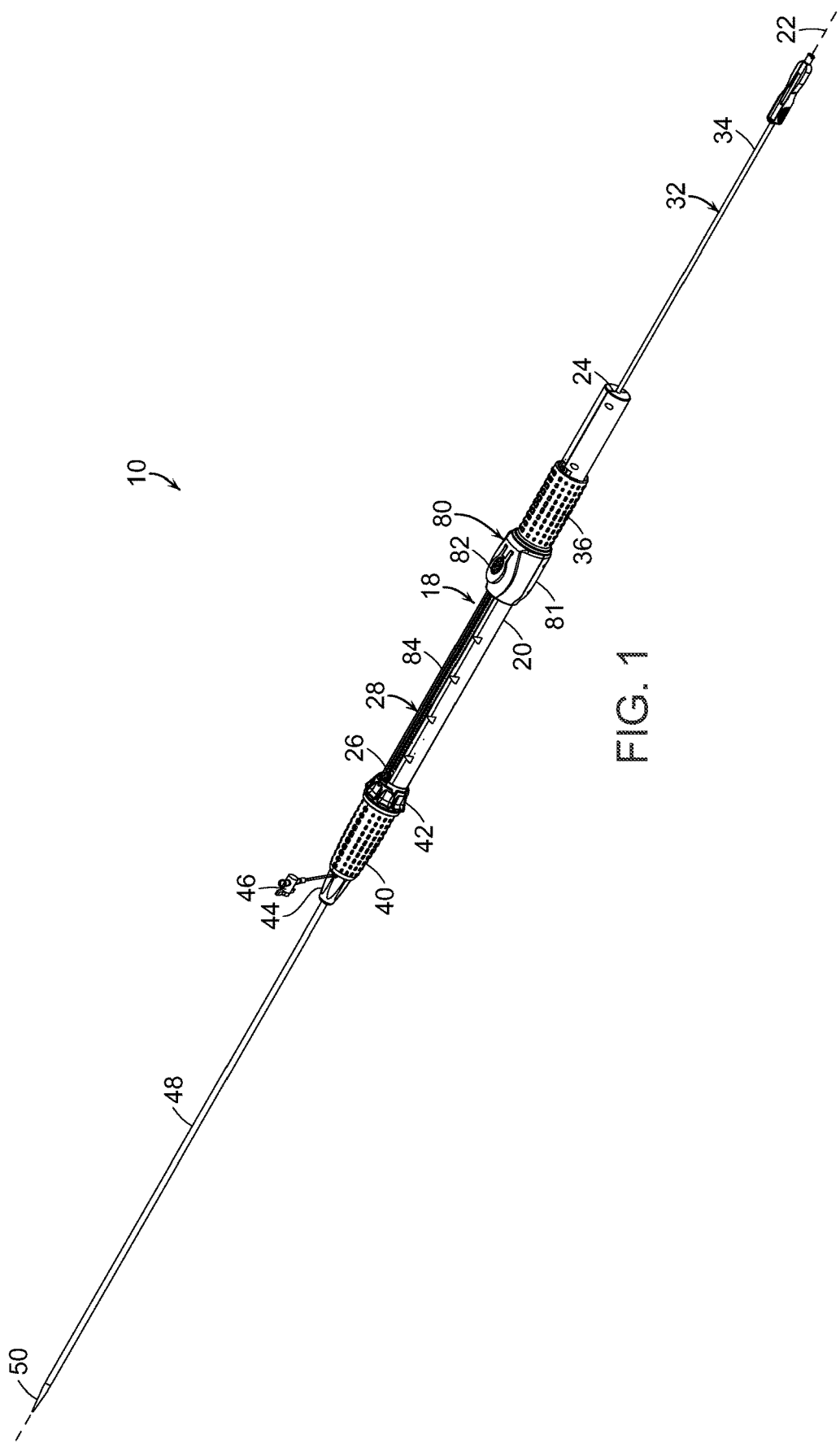
FIG. 1 is a perspective view of one embodiment of the delivery device of the invention.

One embodiment, of the delivery device 10 of the invention is shown in FIG. 1. Delivery device 10 includes guidewire catheter 12 (FIGS. 10, 11) having a proximal end 14 and a distal end 16. "Proximal," as a term employed herein with reference to the delivery device and its components, means relatively close to the surgeon operating the delivery device. "Distal," as a term employed herein with reference to the delivery device and its components, means relatively distal from the surgeon operating the delivery device. "Proximal," as a term employed herein with reference to the prosthesis, stent-graft and components, means relatively close to the heart of the patient. "Distal," as a term employed herein with reference to the prosthesis, stent-graft and components, means relatively distal from the heart of the patient. Returning to FIG. 1, delivery device 10 includes delivery assembly 18 that extends about the guidewire catheter (not shown). Delivery assembly 18 includes handle body 20 having major longitudinal axis 22, proximal end 24 and distal end 26. Delivery catheter 28 (FIG. 9) has distal end 30 (FIG. 27B) extending from within distal end 26 of handle body 20 (FIG. 1) and about the guidewire catheter (not shown).

Figure 10:
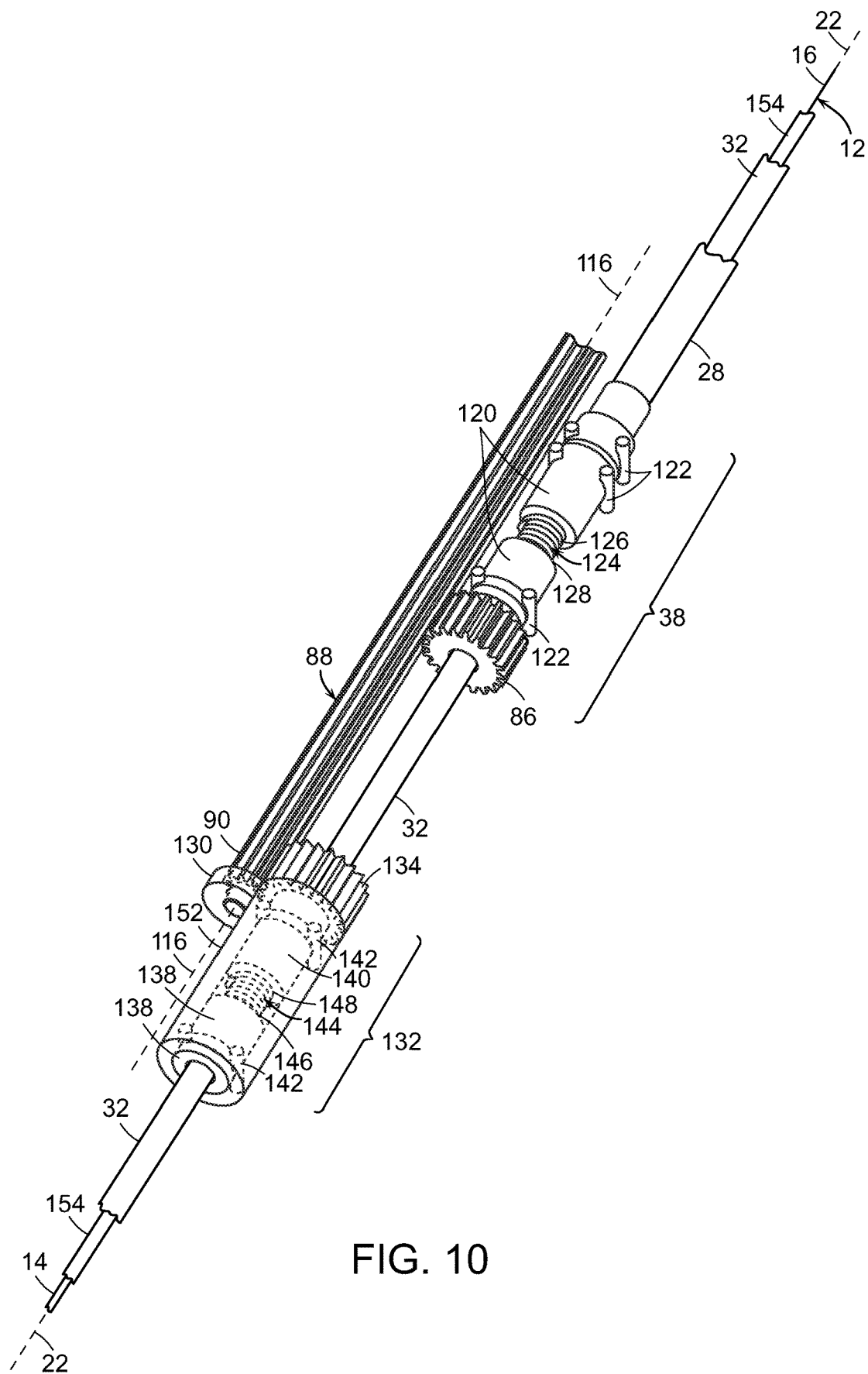
FIG. 10 is a perspective view of first locking component, and second locking component, and their relation to the drive shaft of the embodiment shown in FIG. 1.
Figure 11:
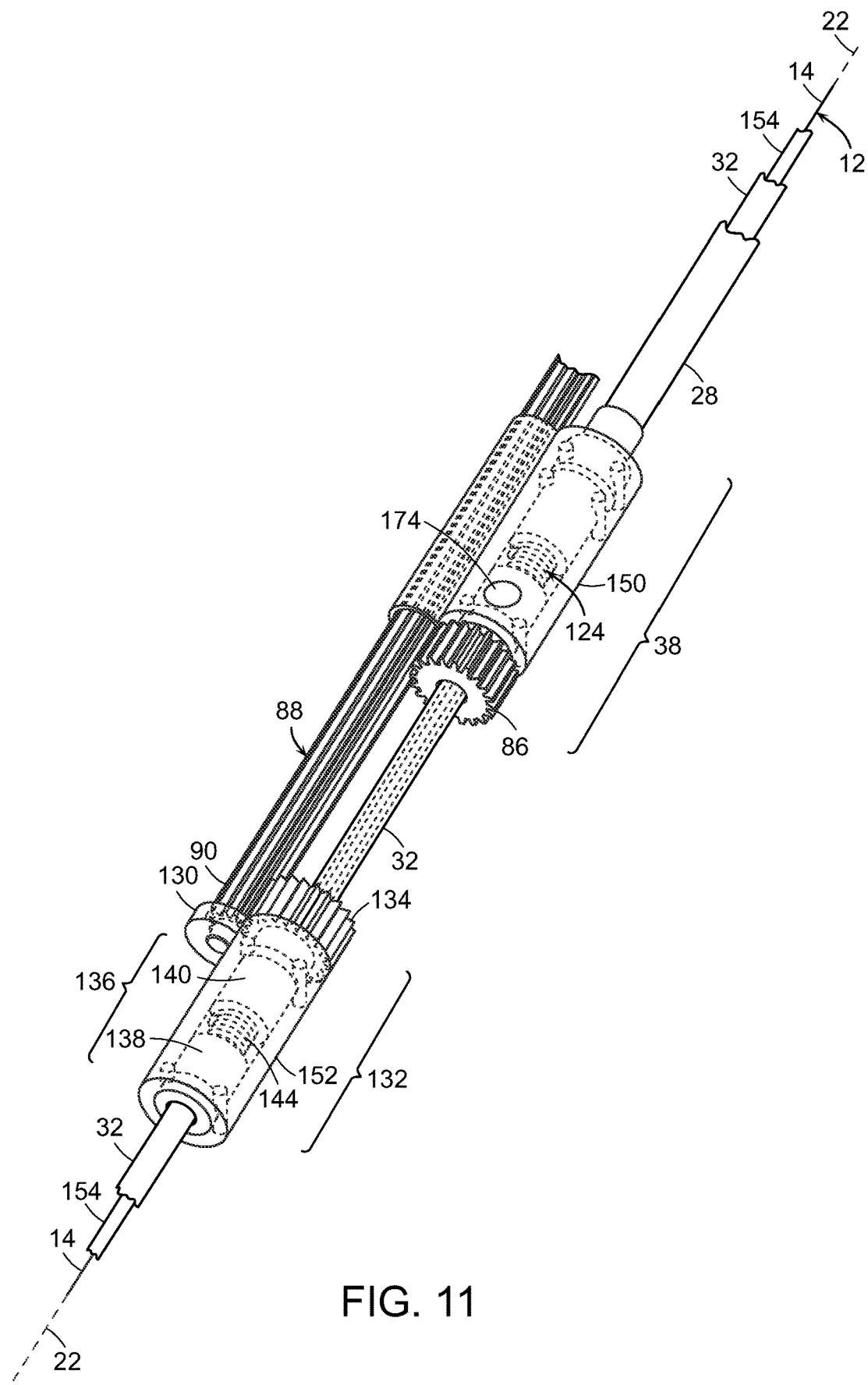
FIG. 11 is another representation of a first locking component and a second locking component, and a first locking component housing and a second locking component housing stabilizing the spatial relation between the first locking component and the second locking component, respectively, relative to the drive shaft of the embodiment of FIG. 1.

In one embodiment, push rod 32 extends about guidewire catheter 12 and within delivery catheter 28 (FIGS. 10, 11).

Figure 25:
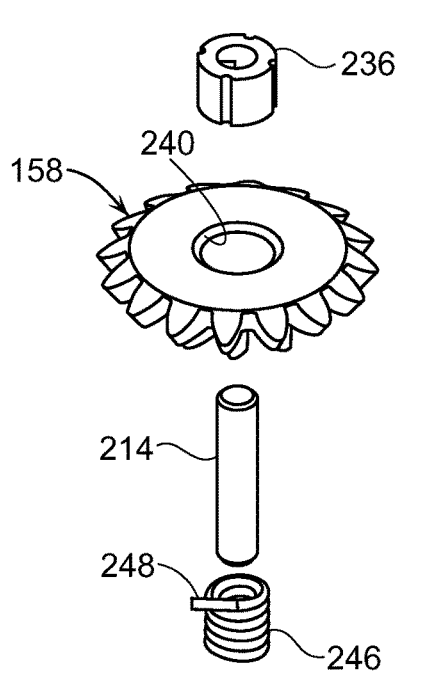
FIG. 25 is an exploded view of a linking gear assembly of the invention that includes a first clutch that is a one-way needle roller bearing clutch and a second clutch that is a coil spring.

Push rod 32 is fixed to guidewire catheter 12 at proximal end 34 of push rod 32 proximal to the handle body at pin 192 (FIG. 25). Referring back to FIG. 1, proximal handle 36 extends about handle body 20 and is axially fixed to delivery catheter 28. Proximal handle 36 is selectively fixed to push rod 32, wherein proximal handle 36 is rotatable about handle body 20 and rotation of proximal handle 36 about handle body 20 translates to longitudinal movement of delivery catheter 28 along longitudinal axis 22 and, selectively, of push rod 32 relative to handle body 20, as can be seen by comparing FIG. 12A with FIG. 12B. First locking mechanism 38 (FIG. 15) at handle body 20 selectively engages proximal handle 36 (FIGS. 12A and 12B) with push rod 32.

Figure 15:
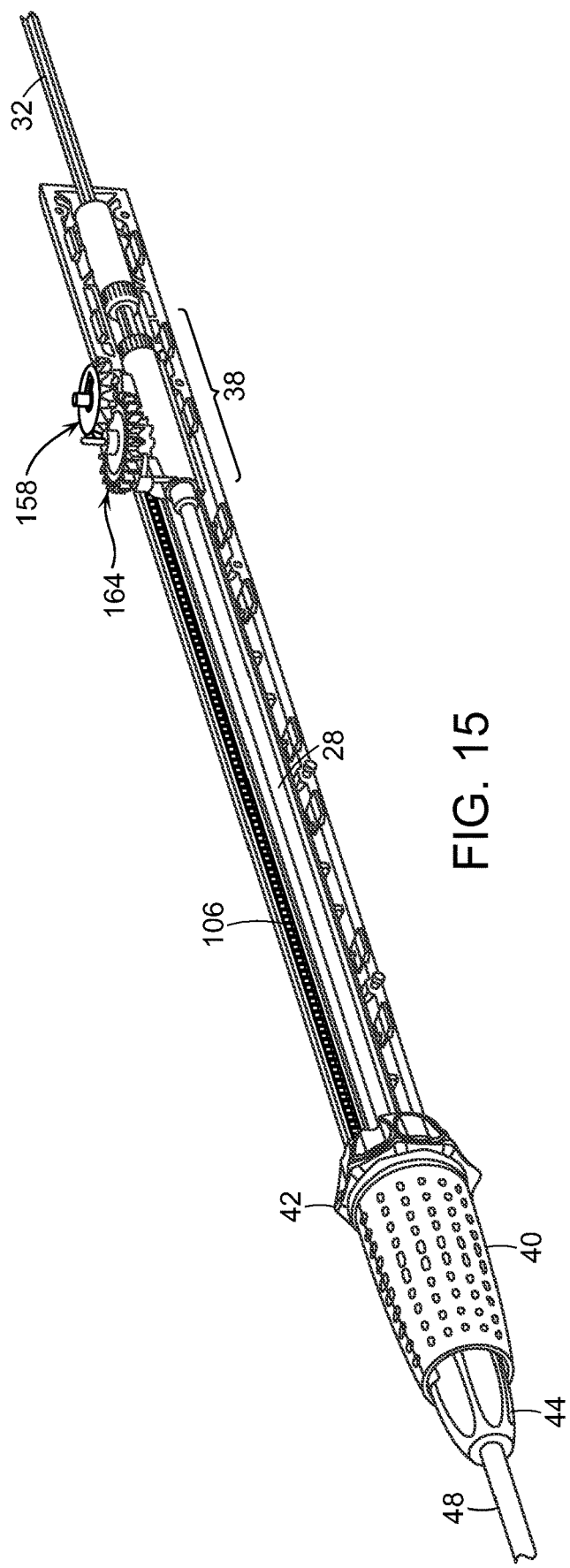
FIG. 15 is a partial cutaway of the embodiment of FIG. 1 showing the relation of the pinion and the linking gear assemblies relative to the first locking component housing and the relationship of the first locking component housing to the delivery catheter within the housing.

Distal handle 40 extends about handle body 20 at distal end 26 of handle body 20 and is distal to shifting knob 42 of locking mechanism 37, that includes first locking mechanism 38 and second locking mechanism 132 (FIG. 15). Distal handle nose 44 (FIG. 1) extends distally from distal handle 40 and includes flush port 46 for providing fluid communication between a solution source (not shown) and interior components of delivery device 10, as necessary, to hydrate contact between components of delivery device 10 and a vascular prosthesis (not shown) within a subject before implantation of the vascular prosthesis in a subject. Outer catheter 48 extends from distal handle nose 44 (FIG. 1).

Actuator 80 is linked to proximal handle 36, whereby proximal handle 36 can rotate about handle body 20 while push-button 82 at housing 81 of actuator 80 remains aligned with slot 84 defined by handle body 20. Depression of push-button 82 of actuator 80 selectively disengages rotation of proximal handle 36 from handle body 20, whereby rotation of proximal handle 20 is independent of longitudinal movement of delivery catheter 28 relative to handle body 20 along longitudinal axis 22.

Figure 2:
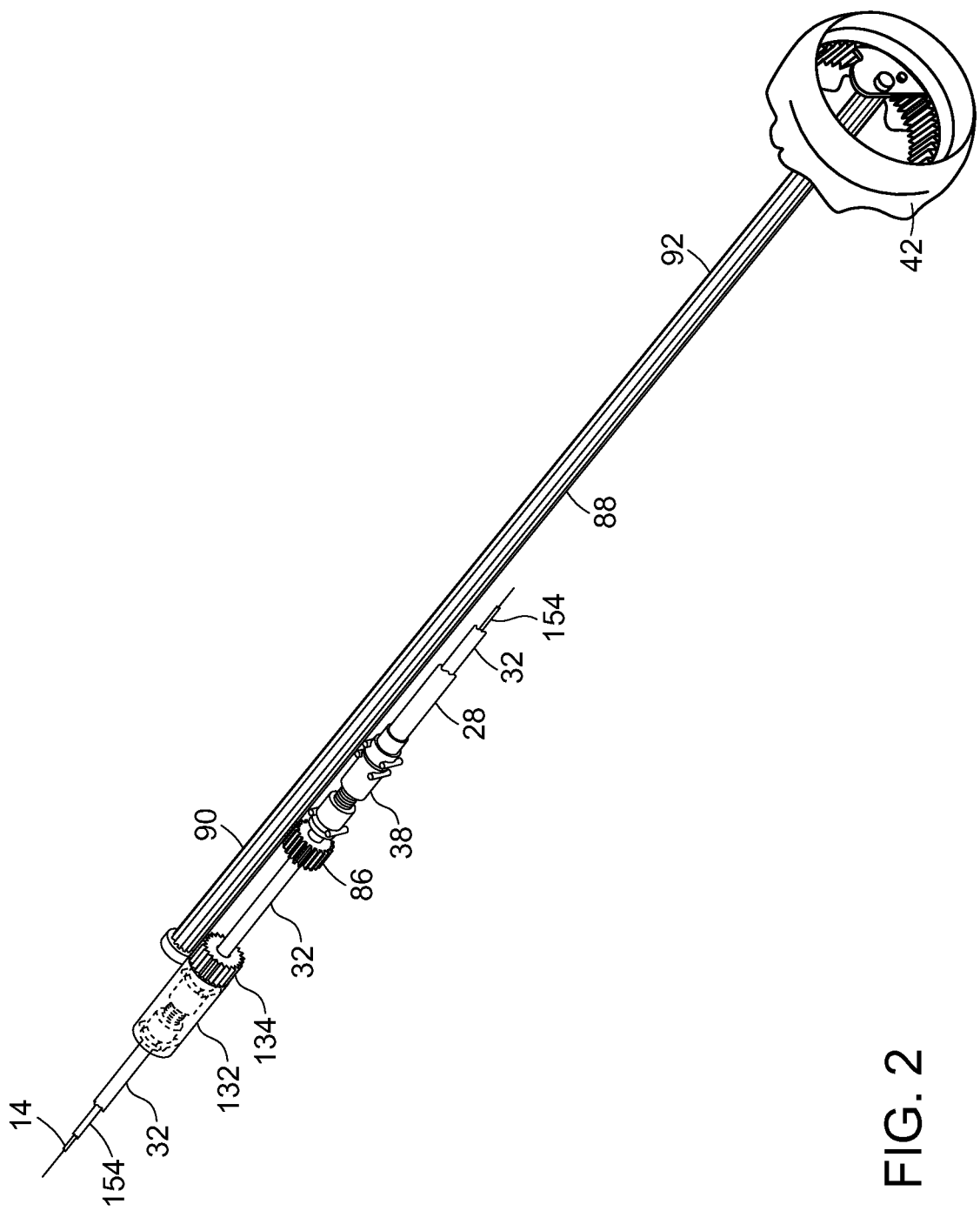
FIG. 2 is a perspective view of one embodiment of a shifting knob, driveshaft and actuator, of the invention.
Figure 3:
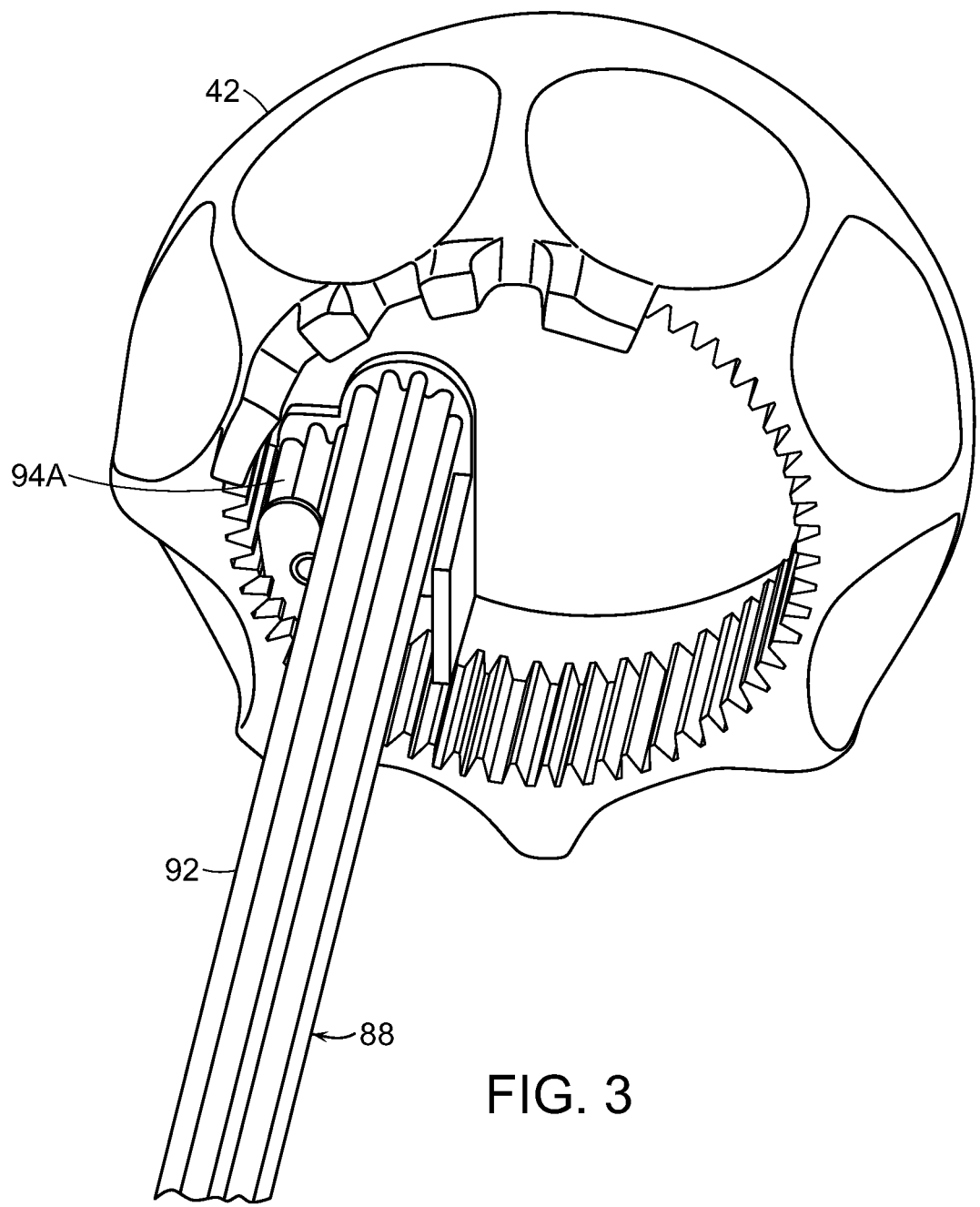
FIG. 3 is a perspective view of the shifting knob and driveshaft of the embodiment shown in FIG. 2.

As can be seen in FIG. 2, shifting knob 42 is linked to drive gear 86 by drive shaft 88. Drive shaft 88 has proximal end 90 and distal end 92, and runs along the interior of the handle body 20 (not shown). As can be seen in FIG. 3, shifting knob 42 is linked to drive shaft 88, in one embodiment, by intermediate gear 94A, whereby rotation of shifting knob 42 about handle body 20 causes rotation of drive shaft 88 by virtue of linkage between shifting knob 42 and drive shaft 88 by intermediate gear 94A. In this embodiment, shifting knob 42 is linked to drive shaft 88 indirectly, as opposed to direct linkage. "Direct linkage" is an optional embodiment, which would be direct contact between shifting knob 42 and drive shaft 88. Shifting knob 42 is rotatably linked to distal handle 40, which is fixed to distal end 26 of handle body 20, as shown in FIG. 1.

Figure 6:
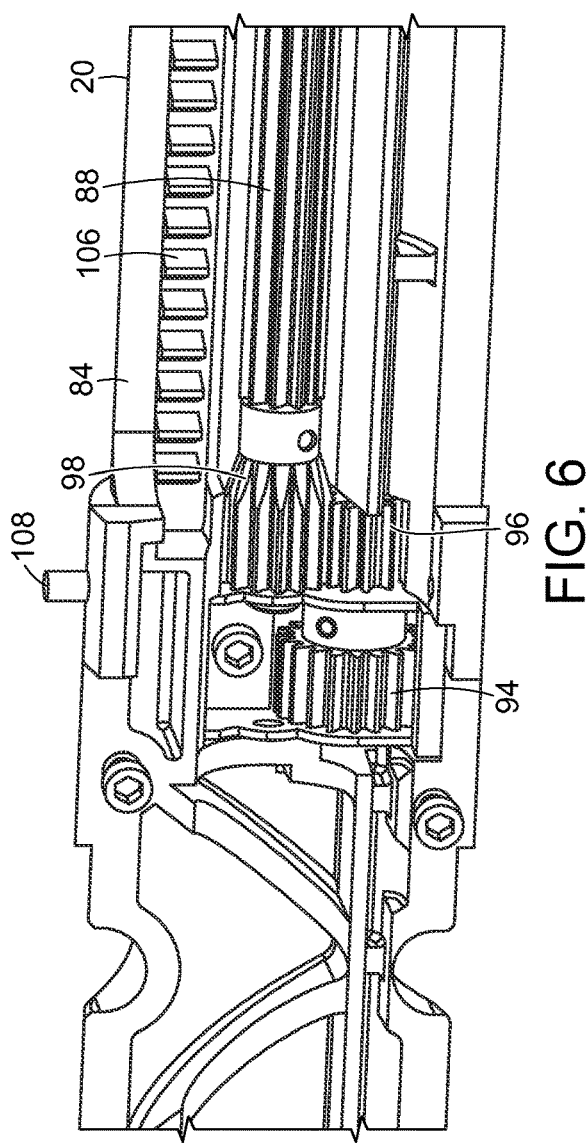
FIG. 6 is a partial cutaway section of a detail of a portion of the handle body, intermediate gear, reduction gear and connecting gear, all of which link the shifting knob with the driveshaft of the embodiment of the invention shown in FIG. 4.
Figure 7:
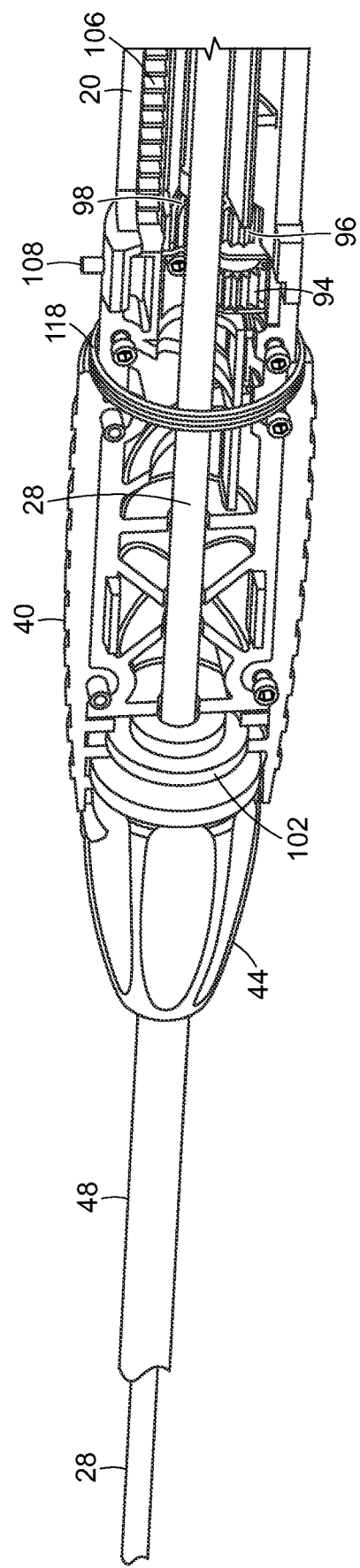
FIG. 7 is a partial cutaway view of the embodiment of FIG. 4, showing a cross-sectional view of the distal handle and a base to which outer catheter is connected at distal handle nose.

In another embodiment, shown in FIGS. 4 and 5, linkage between shifting knob 42 and drive shaft 88 includes a gear reduction at intermediate gear 94B that is linked to coaxial reduction gear 96 which, in turn, is linked to connecting gear 98 that is coaxially linked to drive shaft 88. By virtue of the gear reduction, the rate of rotation of shifting knob 42 relative to drive shaft 88 can be controlled by the relative dimensions of reduction gear 96 and connecting gear 98 (FIGS. 5, 6, 7). Typically, the rotation ratio, or reduction ratio, of shifting knob 42:drive shaft 88 is in a ratio of between about 1:2 and about 1:6. The relationship between reduction gear 96 and connecting gear 98 can be seen in greater detail in FIG. 6.

Figure 8:
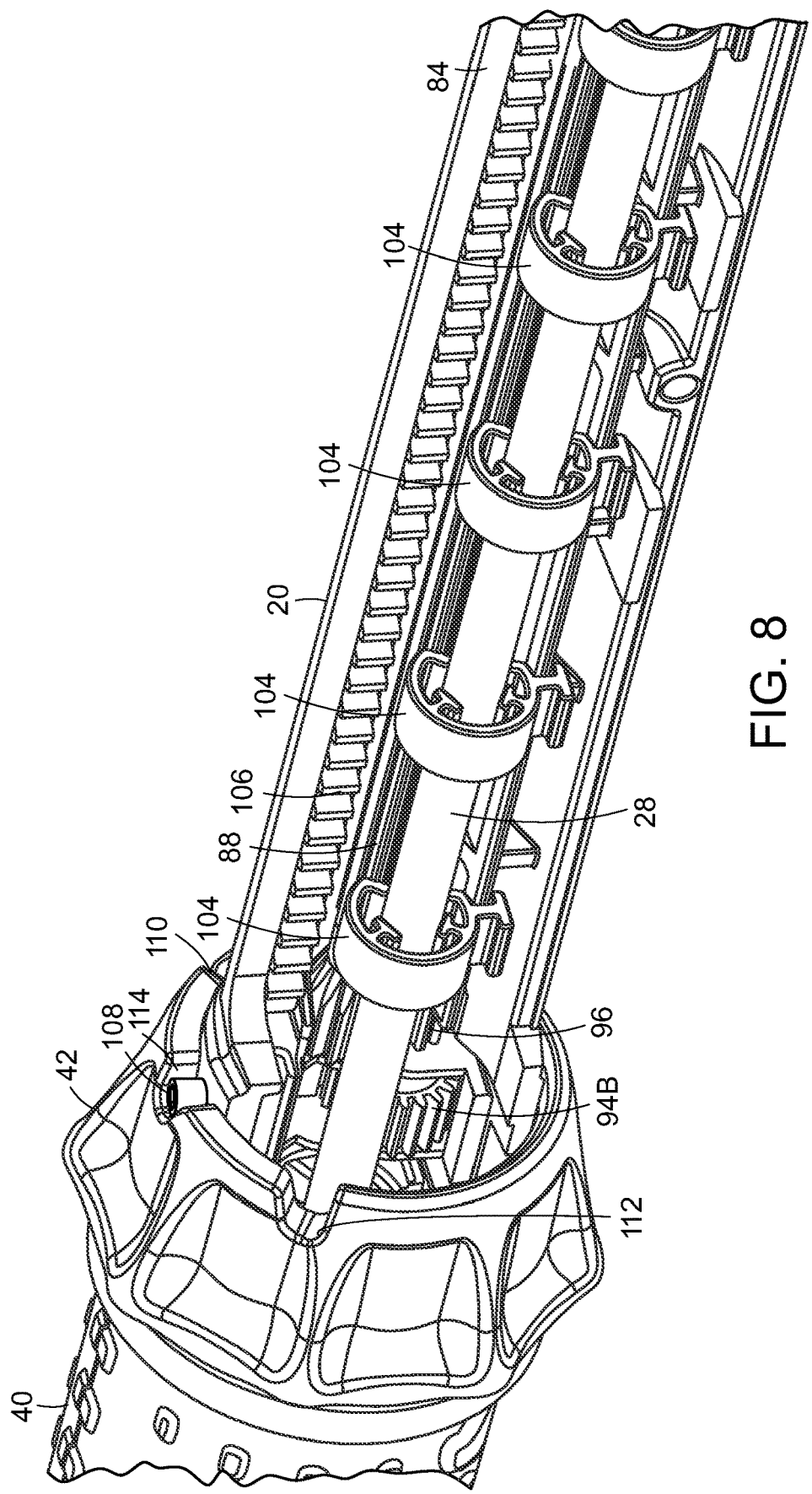
FIG. 8 is a partial cutaway, of the embodiment of FIG. 4 showing constricting rings extending about a delivery catheter.
Figure 9:
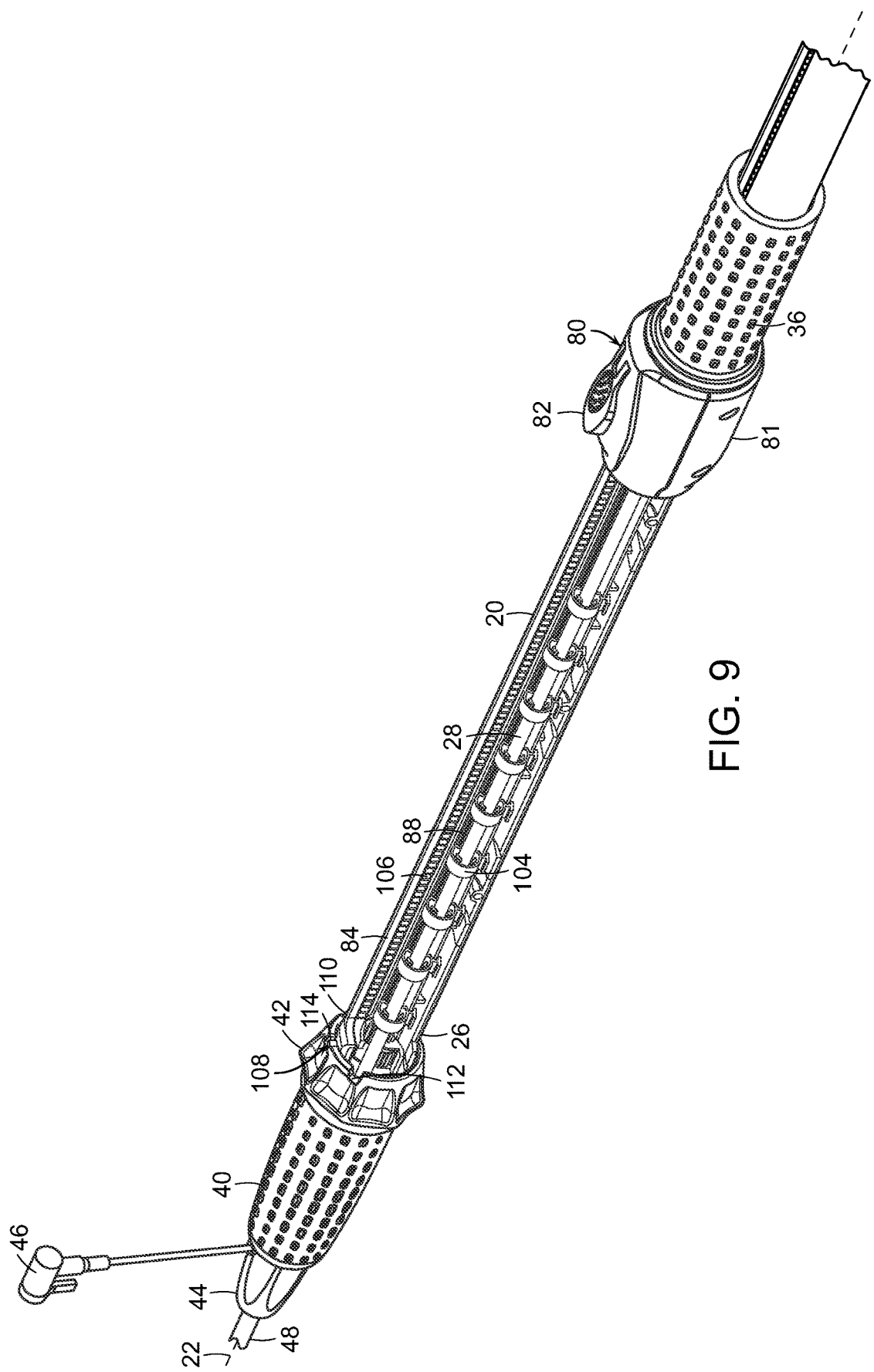
FIG. 9 is another embodiment of a partial cutaway of the delivery device of FIG. 1 showing an actuator and a push button at the proximal end of a slot defined by the handle body.

As can be seen in greater detail in FIG. 7, delivery catheter 28 extends through handle body 20, distal handle 40 and distal handle nose 44. Referring back to FIG. 5, outer catheter 48 is linked to base 102, whereby outer catheter 48 is rotatable independently of handle body 20. As shown in FIG. 8, constricting rings 104 extend along the delivery catheter 28 within handle body 20. As shown in FIGS. 8 and 9, constricting rings 104 have an outside diameter greater than the width of slot 84, whereby constricting rings 104 will prevent application of longitudinal compressive force by proximal handle 36 on delivery catheter 28 from causing delivery catheter 28 to buckle and thereby move through slot 84 and outside of handle body 20. Constricting rings 104 also have an inside diameter slightly less than the outside diameter of delivery catheter 28, whereby constricting rings 104 will have an interference fit with delivery catheter 28, so that constricting rings 104 can move longitudinally along delivery catheter 28 if directed, but otherwise will remain in place relative to delivery catheter 28. Gear rack 106 extends longitudinally within handle body 20. Pin 108 at distal end 26 of handle body 20 extends from distal end 26 of handle body 20 and is selectively slotted within slots 110,112,114 of shifting knob 42. Shifting knob 42 is longitudinally moveable along handle body 20 and is rotatable about handle body 20 sufficient to allow rotation of shifting knob 42 to move placement of pin 108 within any of slots 110,112,114 of shifting knob 42, which thereby causes rotation of intermediate gear 94. As a consequence, drive shaft 88 rotates about longitudinal axis 116 (FIG. 10) of drive shaft 88. Shifting knob 42 is a biased against pin 108 by spring 118 (FIG. 7).

As can be seen in FIG. 9, gear rack 106 and drive shaft 88 extend the length of slot 84. FIG. 10 shows the relation between drive shaft 88, push rod 32 and first locking mechanism 38. Push rod 32 extends through first locking mechanism 38 which, in turn, is engaged with drive shaft 88 at drive gear 86 of first locking mechanism 38. First locking mechanism 38 is fixed relative to proximal handle (not shown) at distal bearings 120 through which push rod 32 extends. Distal bearings 120 are linked to first locking component housing 150 by pins 122. First locking component 124 of first locking mechanism 38 is fixed relative to distal bearings 120 at distal end 126 and linked to drive gear 86 at proximal end 128, whereby rotation of drive shaft 88 and consequent rotation of drive gear 86 will further coil, or reduce coil, of first locking component 124, resulting in engagement or disengagement, respectively, of locking mechanism 38 and, consequently, proximal handle (not shown), with push rod 32. When first locking mechanism 38 is engaged with push rod 32, longitudinal movement of proximal handle (not shown) along drive shaft 88 and, thus, handle body 20, will cause longitudinal movement of push rod 32 along drive shaft 88 and handle body 20, as can be seen by comparing FIGS. 12A and 12B.

Referring back to FIGS. 10, 11, drive shaft 88 is rotatably fixed to handle body 20 (FIG. 9) at driveshaft bearing 130, which is part of second proximal locking component housing 152 at proximal end 90 of drive shaft 88. Second locking mechanism 132 includes translating gear 134 that is engaged with drive shaft 88 at proximal end 90 of the drive shaft 88 and is rotatably engaged with mechanism bearings 136 (FIG. 11), including proximal bearing 138 (FIG. 10) and distal bearing 140 (FIG. 10) which, in turn, are fixed relative to handle body 20 at pins 142. Proximal bearing 138 is radially and axially fixed to handle body 20. Distal bearing 140 is axially fixed to handle body 20. Second locking component 144 of second locking mechanism 132 is engaged with one of proximal bearing 138 at proximal end 146 of second locking component 144, and engaged with translating gear 134 at distal end 148 of second locking component 144, whereby rotation of drive shaft 88 and, consequently, rotation of translating gear 134 will tighten and engage, or loosen and disengage, second locking component 144 with push rod 32. When engaged with push rod 32, second locking component 144 causes push rod 32 to be fixed in location relative to handle body (not shown). When loosened and disengaged from push rod 32, push rod 32 is longitudinally movable relative to handle body (not shown). The orientation of first locking component 124 and second locking component 144 are reversed, whereby rotation of drive shaft 88 in one direction will, simultaneously, cause engagement and disengagement of first locking component 124 and second locking component 144 with push rod 32, respectively. Disengagement of first locking component 124 from push rod 32 is caused by movement of shifting knob 42 from a first position defined by pin 108 at slot 110 of shifting knob 42 to second position 112, defined by pin 108 at second slot 112 of shifting knob 42 (FIG. 9). The same movement from the first to second position of shifting knob 42 will simultaneously cause engagement of second locking component 144 with push rod 32, whereby push rod 32 will be fixed in position relative to handle body 20 at second locking component 144 regardless of movement of proximal handle 36 along longitudinal axis 116 of handle body 20. Referring back to FIGS. 8 and 9, positioning shifting knob 42, so that pin 108 is at intermediate slot 114 between the first slot 110 and second slot 112 of shifting knob 42, will cause both first locking component 124 and second locking component 144 to be disengaged from push rod 32.

As can be seen in FIG. 11, first locking component housing 150 fixes lateral movement of first locking component 124 and drive shaft 88, and second locking component housing 152 fixes the position of second locking component 144 and bearings 138,140 relative to proximal end 90 of drive shaft 88, respectively. Further, as can also be seen in FIG. 11, apex release catheter 154 extends within push rod 32 and guidewire catheter 12 extends within apex release catheter 154.

Figures 12A, 12B:
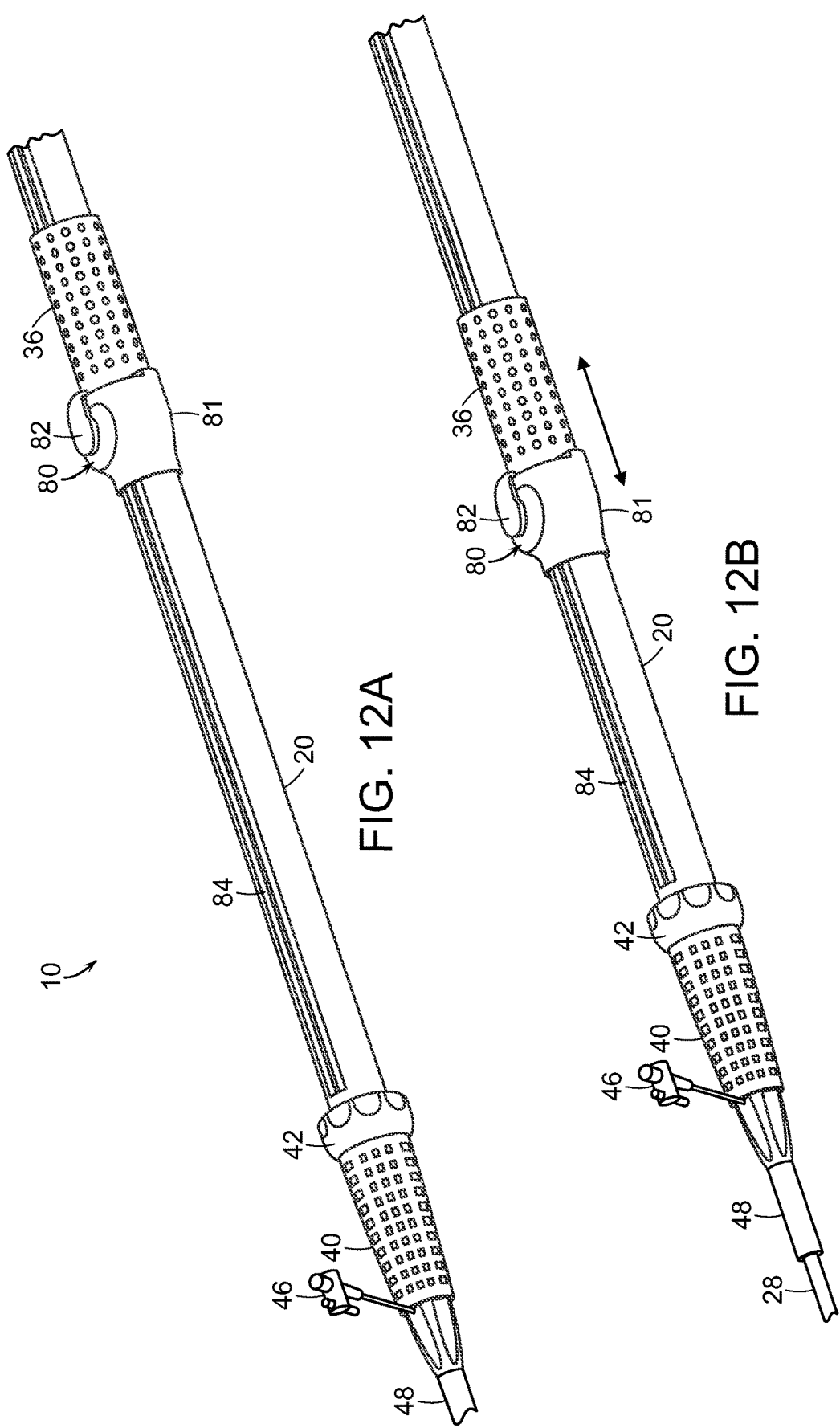
FIG. 12A is another perspective view of the embodiment of FIG. 1, showing displacement of the proximal handle and the actuator along the handle body consequent to rotating of the proximal handle about the handle body or depressing the push button of the actuator to thereby allow longitudinal movement of the actuator and the proximal handle without rotation of the proximal handle.
FIG. 12B is another perspective view of the embodiment of FIG. 1, wherein a proximal handle has been advanced along the handle body of the delivery system.

FIGS. 12A and 12B indicate relative movement of actuator 80 and proximal handle 36 along handle body 20. Rotation of proximal handle 36 about handle body 20, when push button 82 is in a first position, as shown in FIGS. 12A and 12B, will cause longitudinal movement of proximal handle 20 and actuator 80 along handle body 20. Upon depression of push button 82 to a second position essentially flush with actuator housing 81, rotation of proximal handle 36 will not cause longitudinal movement of proximal handle 36 or actuator along handle body 20. Rather, proximal handle 36 and actuator 80 will be movable along handle body 20 without rotation of proximal handle 36 about handle body 20.

Figure 13:
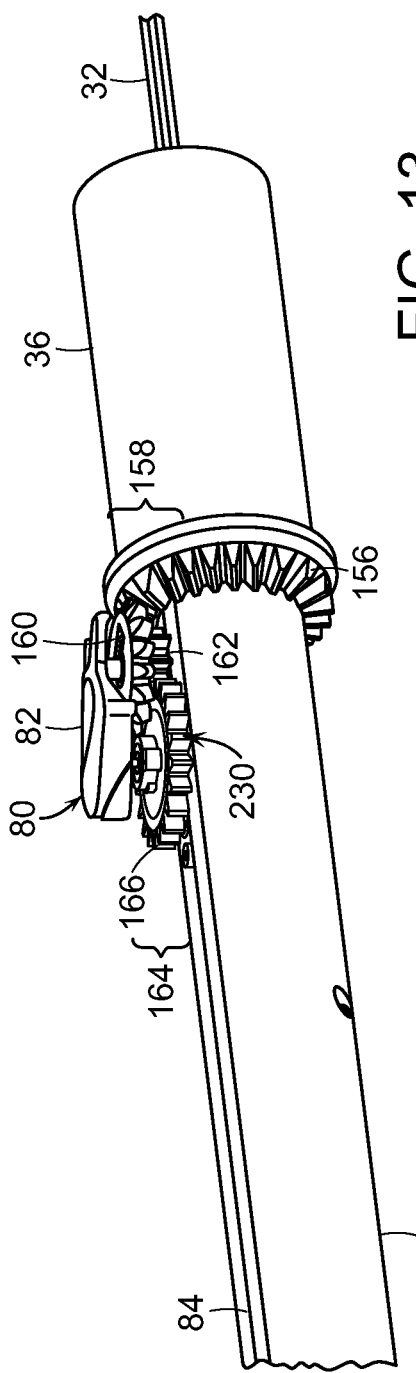
FIG. 13 is a detail of the proximal handle and the actuator at the handle body of the embodiment of the invention shown in FIG. 1, without the actuator housing.
Figure 14:
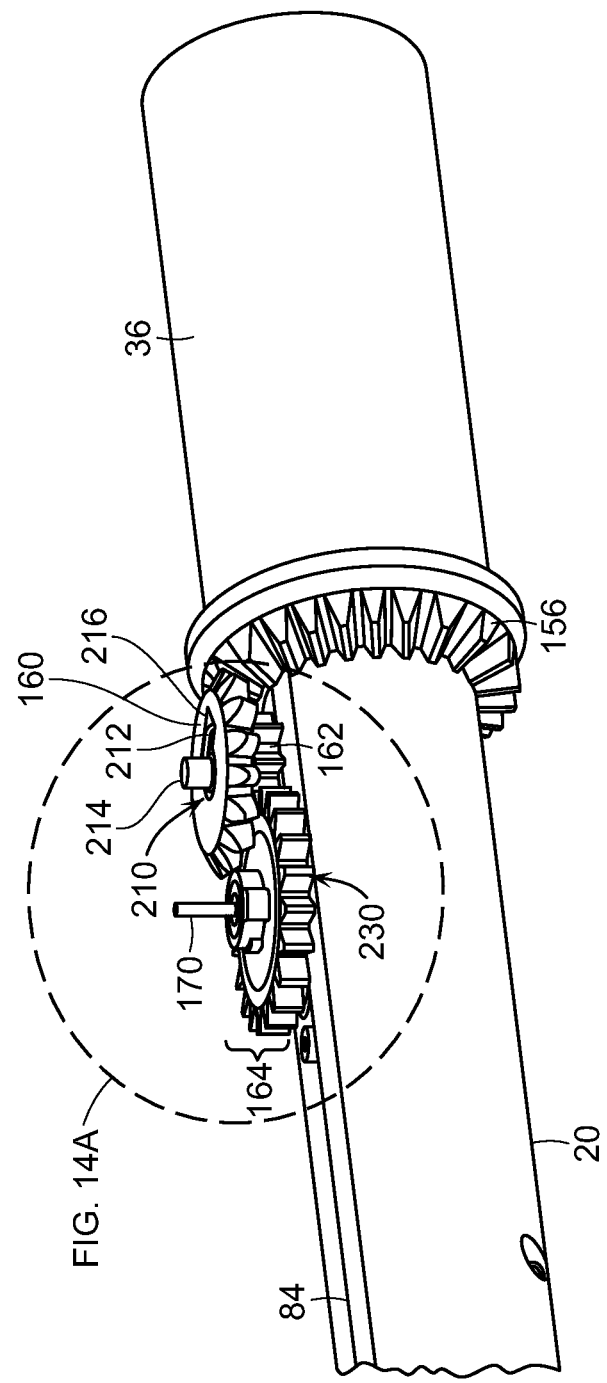
FIG. 14 is a perspective view of the detail of FIG. 13, without the push button of the actuator shown in FIG. 13.

As can be seen in FIGS. 13-15, teeth 156 of proximal handle 36 engage upper linking gear 160 of linking gear assembly 158. Linking gear assembly 158 is engaged with pinion gear assembly 164. Lower linking gear 162 of linking gear assembly 158 engages upper pinion gear 166 of pinion gear assembly 164. Pinion gear assembly 164 is linked to first locking component housing 150 (FIG. 11) through slot 84. Linking gear assembly 158 and pinion gear assembly 164 are components of actuator 80, referenced with respect to FIG. 1. As can be seen in FIGS. 14 and 14A, coil spring 210 is seated about pin 214 and is fixed at end 212 within recess 216 of upper linking gear 160.

Figure 16:
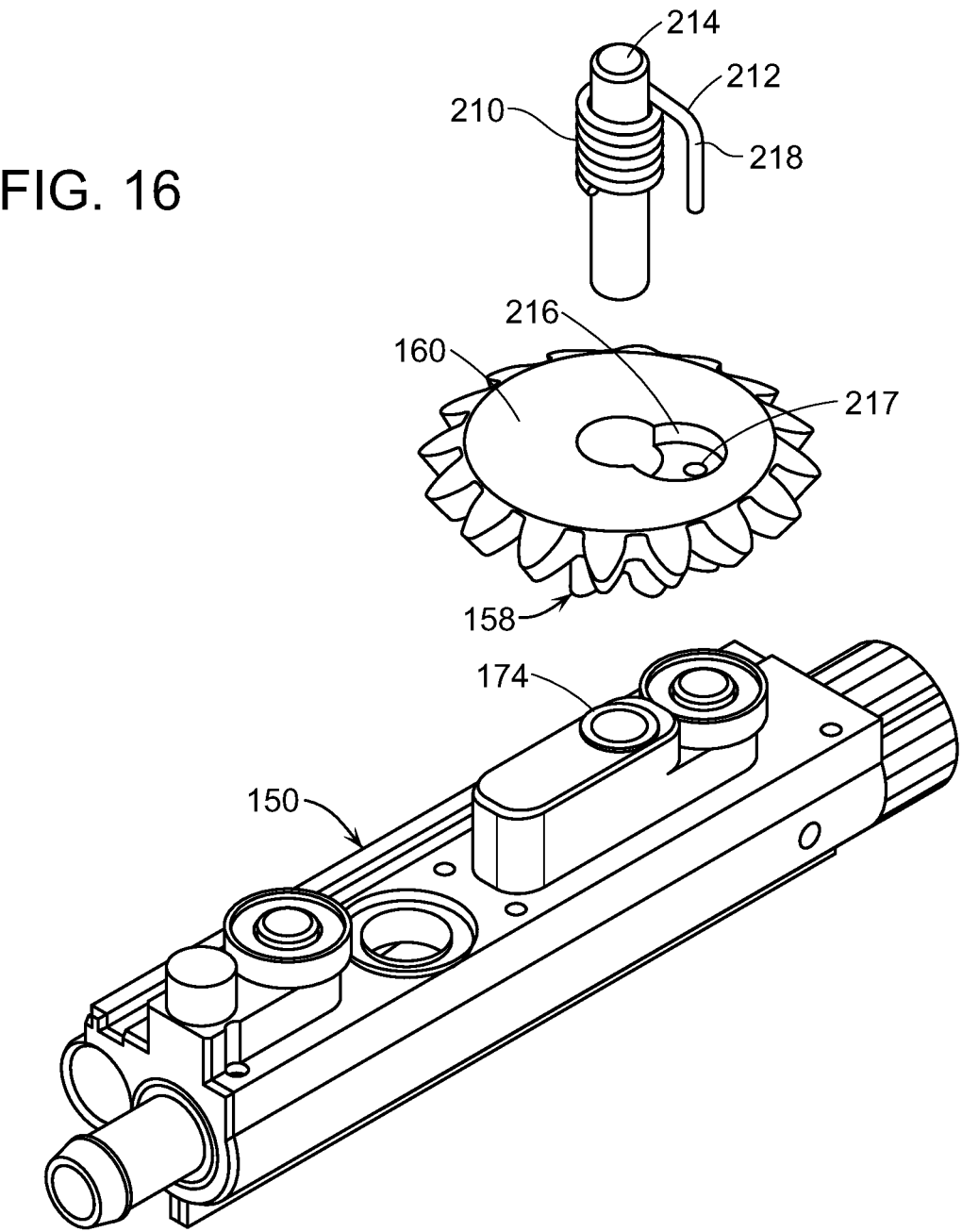
FIG. 16 is an exploded view, in perspective, of a first locking mechanism, a linking gear, a pin, and a coil spring clutch of one embodiment of a delivery device of the invention.

FIG. 16 is an exploded view of first locking component housing 150, pin 214, upper linking gear 160 and coil spring 210, in perspective, showing how coil spring 210 is wrapped about, or around, pin 214, and extension 218 at one end 212 of coil spring 210 is hooked to allow coil spring 210 to be fixed at opening 217 of upper linking gear 160 against rotation about pin 214 when upper linking gear 160 is rotated in a direction that causes spring 210 to tighten about pin 214. In this case, pin 214 is aligned with, and to be seated in socket 174 (FIG. 11) of first locking component housing 150 when assembled. Pin 214 is in sufficient contact with coil spring 210 when assembled to cause rotation of upper liking gear 160 in one direction to tighten coil spring 210 about pin 214, thereby causing the coil spring 210 to act as a clutch, where further rotation of the linking gear assembly 158 will also cause rotation of pin 214. For example, as shown in FIG. 16, rotation of upper linking gear 160 in a clockwise direction about pin 214 will cause coil spring 210 to tighten about pin 214, thereby locking with pin 214 as a clutch mechanism, causing pin 214 to rotate with upper linking gear assembly 158 upon continued clockwise rotation of upper linking gear 160. This clutching mechanism, whereby pin 210 tightens about pin 214 and locks with it, can occur, for example, by direction of first locking mechanism 38 (FIG. 15) in a proximal direction (toward the surgeon) by longitudinal expansion of a vascular prosthesis 58 (FIG. 47A, infra) during implantation prompted by release of proximal handle 36 by the surgeon after having advanced the prosthesis to a surgical site. Conversely, when proximal handle 36 is rotated by the surgeon in a clockwise direction, upper linking gear 160, the teeth of which are engaged with teeth of proximal handle 36, will rotate in counterclockwise direction, thereby causing coil spring 210 to expand in diameter about pin 214 and thereby release pin 214 from rotation of upper linking gear 160.

Figure 17:
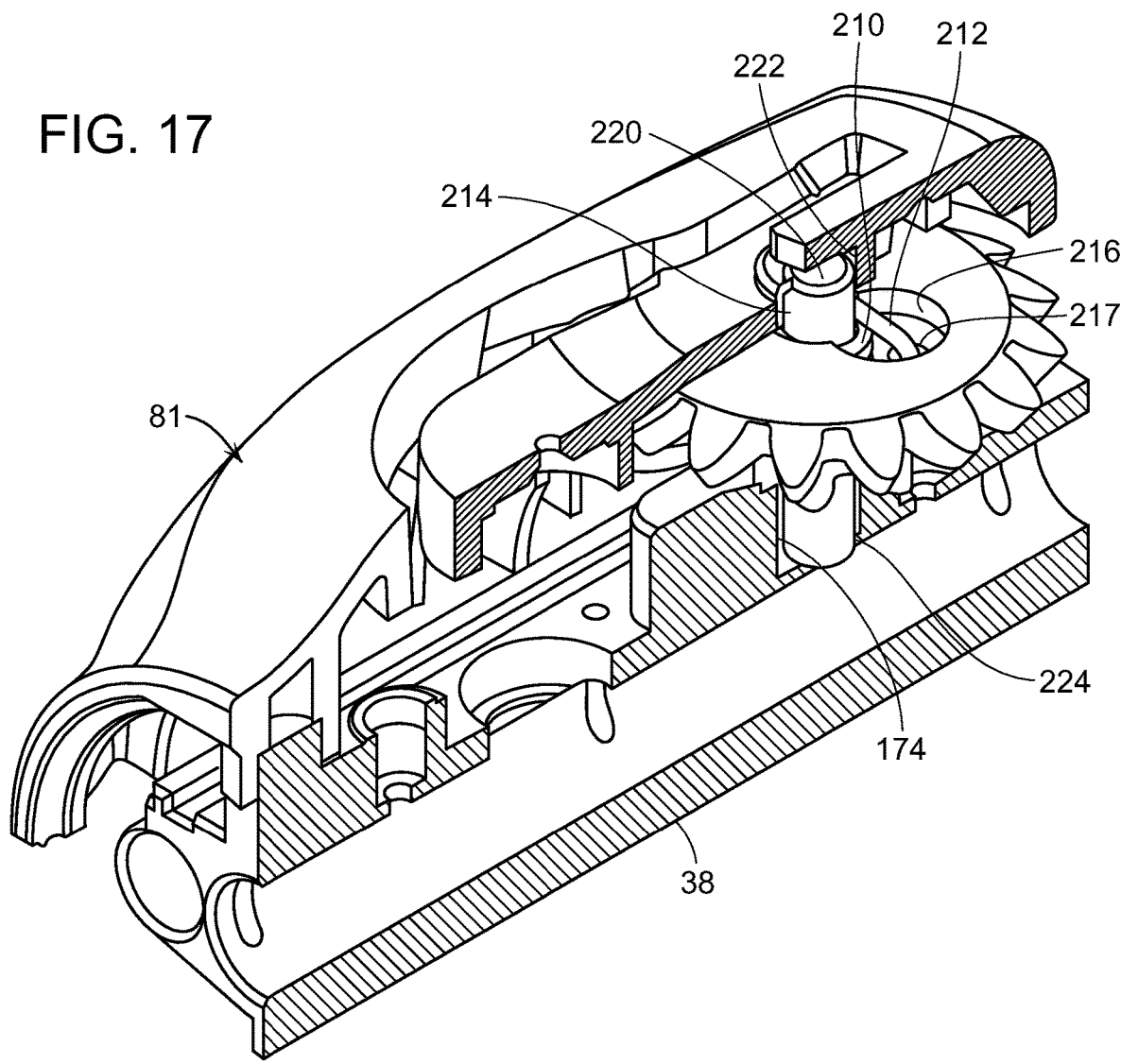
FIG. 17 is a partial cut-away view, in perspective, of a housing, and the first locking mechanism, linking gear, pin, and coil spring of FIG. 16, when assembled.

FIG. 17 is a partial cut-away view, in perspective, of a portion of housing 81 and first locking mechanism 38, in combination with linking gear assembly 158. Pinion gear assembly 164 is not shown for the purpose of clearly showing linking gear assembly 158. As can be seen from the embodiment of the invention shown in FIG. 17, pin 214 extends through linking gear assembly 158 and is secured at one end 220 in socket 222 defined by housing 81 and at opposite end 224 in socket 174 defined by first locking mechanism 38. In this embodiment, pin 214 is seated in at least one of socket 222 and socket 174 with an interference fit, whereby pin 214 will resist rotation about its longitudinal axis. The resistance is sufficient to prevent longitudinal expansion of a stent graft to be delivered along longitudinal axis 22 (FIG. 1) when proximal handle 36 (FIGS. 1, 13, 14) is released by the surgeon after at least partial advancement of a vascular prosthesis, thereby preventing backspin. The resistance to rotation of pin 214 is not so great, however, that it cannot be overridden by the surgeon in the event the vascular prosthesis is to be intentionally moved back toward the surgeon (prior to deployment of the vascular prosthesis) by rotating proximal handle 36 in the opposite direction to that of advancement (such as in a counterclockwise direction, which is opposite to the clockwise direction of rotation of the proximal handle 36 described above). In one embodiment, the amount of force exhibited as resistance to rotation by housing 81 is in a range of between about 2.0 lbf. inch and about 12.0 lbf. inch. In another embodiment, the amount of force exhibited as resistance to rotation by housing 81 is in a range of between about 5.0 lbf. inch and about 7.0 lbf. inch. Preferably, housing 81, or at least the portion of housing 81 defining socket 222, is fabricated of medical grade engineering plastic that is gamma radiation-compatible. Housing 81 preferably is an injection molded engineering plastic. Socket 222 may also be injection molded engineering plastic. Preferably, first locking mechanism 38 defining socket 174 is fabricated of stainless steel, anodized aluminum or medical grade engineering plastic. Preferably, only socket 222 of housing 81 provides resistance to rotation of pin 214. Depending on where resistance to backspin is to be overcome in the delivery device of the invention, at least one of sockets 174, 222, pin 214, or the needles of a one-way needle roller bearing clutch, described below, can be formed of stainless steel in order to control, in part the torque force required to overcome the static friction of the interference fit. In another embodiment, not shown, where a second clutch is employed, such as at socket 174, the second clutch provides resistance to rotation of pin 214.

In another embodiment of the invention, shown in FIG. 18, coil spring 214 of FIGS. 16 and 17 is replaced by one-way needle roller bearing clutch 226, such as is known in the art. A one-way needle roller bearing clutch is a clutch that includes "needles" aligned on the inside surface of a cylinder, where the needles roll freely about a pin that is rotated within the cylinder in one direction, but lock, and thereby provide torque when the pin is directed in an opposite direction of rotation about its axis. FIG. 18 is an exploded view, in perspective, of first locking mechanism 38, pin 214, and linking gear assembly 158, wherein, instead of coil spring 214, one-way needle roller bearing clutch 226 is employed. In this embodiment, when assembled, one-way needle roller bearing clutch 226 will be press fit into orifice 240 defined by upper and lower linking gears of linking gear assembly 158. Like the embodiment shown in FIG. 16, the embodiment of FIG. 18 allows clockwise rotation of proximal handle 36, such as is shown in FIGS. 13 and 14, and consequent counterclockwise rotation of linking gear assembly 158 about pin 214, which is in an interference fit with at least one of socket 222 defined by housing 81, and socket 174 of first locking component housing 150 of first locking mechanism 38, to thereby advance a vascular prosthesis to a surgical site. One-way needle roller bearing clutch 226, however, will lock about pin 214 and resist, by virtue of the interference fit between pin 214 and at least one of socket 222 and socket 174, proximal movement of gearing assembly 230 (FIGS. 13 and 14), consisting of linking gear assembly 158 and pinion gear assembly 164 toward the surgeon, such as would be a consequence a longitudinal expansion of a vascular prosthesis when the surgeon releases proximal handle 36 (FIG. 13 lnd 14) after at least partially advancing the vascular prosthesis toward a surgical site. Like the embodiment shown in FIG. 16, the resistance to rotation of pin 214 provided by the interference between pin 214 and at least one of socket 222 and socket 174, can be overcome by the surgeon by forcefully rotating proximal handle 36 in a counterclockwise direction to thereby retract the vascular prosthesis back toward or within the delivery device. It should be understood that, in alternative embodiments, the component parts of the delivery device can be constructed so that the functions described above can be performed by counterclockwise rotation where clockwise rotation is employed above and by clockwise rotation where counterclockwise rotation is employed. Also, it is to be understood that other arrangements of resistance to rotation of linking gear assembly 158 when one-way needle roller bearing clutch 226 is locked can be employed. For example, in an embodiment where pin 214 is fused with, or locked in place at either housing or first locking mechanism, an interference fit that would resist backspin, but enable a surgeon to retract a vascular prosthesis by rotating proximal handle 36 in a direction about delivery device in a direction opposite to that of advancement could be achieved by, for example, an interference fit between one-way needle roller bearing clutch 226 and linking gear assembly 158, or by overriding friction between pin 214 and component needles within the one-way needle roller bearing clutch 226.

FIGS. 19 and 20 show a side view and a perspective view, respectively, of other embodiments of a linking gear assembly of the invention in combination with a one-way needle roller bearing clutch. In this embodiment, pin 214 is either fused with, or in an interference fit with upper linking gear 160 and lower linking gear 162. In FIG. 19, one-way needle roller bearing clutch 232 is at one end of pin 214 and, while not shown, one-way needle roller bearing clutch 232 will be seated in socket 174 of first locking component housing 150, such as by being press-fit into socket 174. In FIG. 20, one-way needle roller bearing clutch 234 is at the opposite end of pin 214 and, while again not shown, one-way needle roller bearing clutch 234 will be seated in socket 222 of housing, such as by being press-fit into socket 222 of housing 81 (FIG. 17). In either case, resistance to backspin when first locking component housing 150 is urged in a proximal direction (toward the surgeon) (FIGS. 12A and 12B), as a consequence of the surgeon releasing proximal handle 36 after having advanced the vascular prosthesis, can be resisted and caused by any one or a combination of friction between pin 214 and linking gear assembly 158, pin 214 and one-way needle roller bearing clutch 232 or between one-way needle roller bearing clutch 234 and socket 222 (FIGS. 16 and 17), and the one-way needle roller bearing clutch 234 and socket, such as socket 174 or 222, in which it is seated. It is to be understood that the amount of torque applied in resistance to backspin can differ among the components contributing to overall resistance, depending on the application and particular configuration and needs of the delivery device for implantation of a specific vascular prosthesis.

Figure 21:
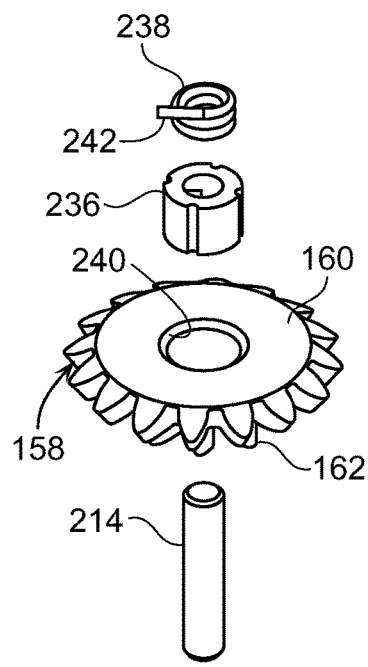
FIG. 21 is an exploded view, in perspective, of a linking gear, a pin, a one-way needle roller bearing clutch as a first clutch, and a coil spring as a second clutch, in still another embodiment of the delivery device of the invention.

FIGS. 21-30 are views of embodiments of the invention wherein the delivery device of the invention includes two clutches 236, 238, each engaging in rotation about pin 214 in an opposite direction to that of engagement of the other about the same pin 214. In each of these embodiments, pin 214 need not be in an interference fit with the socket of either housing 81 or first locking mechanism 38. Instead, while first clutch 236, which can be a one-way roller needle bearing clutch, as shown in FIG. 21, prevents backspin, as described above, second clutch 238, such as a coil spring, extending about pin 214 of the linking gear assembly 158, will engage when the linking gear assembly 158 is engaged with 214 pin and proximal handle 36 (FIGS. 12A and 12B) is being rotated to advance the vascular prosthesis in a distal direction away from the surgeon and toward the surgical site. During engagement of second clutch 238 in this embodiment, pin 214 rotates within second clutch 238 while second clutch 238 is engaged, overcoming static friction between second clutch 238 and pin 214. The torque necessary to overcome resistance to rotation of 214 pin within second clutch 238 while second clutch 238 is engaged can replace that which would result from an interference fit between pin 214 and socket 222 of housing 81 or socket 174 of first locking component housing 150. Second clutch 238 can thereby improve control by the surgeon during surgery by enabling manufacture of a delivery device that is less dependent upon variable factors in the construction of sockets in either housing 81 or first locking locking component housing 150, the specifications for which generally require a very low tolerance in order to function within performance limitations during use. Alternatively, pin 214 and linking gear assembly 158 may not engage during rotation of linking gears 160, 162 that advances the vascular prosthesis. Rather, linking gears 160, 162 rotate freely about pin 214 when linking gears 160, 162 rotate in a direction to advance the vascular prosthesis. Such an arrangement can be a consequence, for example, of first clutch 236, such as one-way needle roller bearing clutch shown in FIGS. 21-24, or a coil spring between the linking gears and the pin, so that first clutch 236 engages linking gears 160, 162 with pin 214 only when first locking mechanism 38 is directed proximally (toward the surgeon) by release of proximal handle 36 (FIGS. 12A and 12B). In this embodiment, second clutch 238 has no function during advancement of the vascular prosthesis by rotation of proximal handle 36, but will provide resistance to rotation of pin 214 (FIG. 21) during any backspin of linking gears 160, 162 and proximal handle 36 caused by direction of first locking mechanism 38 in a proximal direction, or by deliberate rotation of proximal handle 36 by the surgeon to retract the vascular prosthesis. In one embodiment, regardless of whether linking gears 160, 162 rotate freely about pin 214 during advancement of the vascular prosthesis, the force necessary to overcome friction caused by second clutch 238 is less than that caused by first clutch 236.

Figure 22:
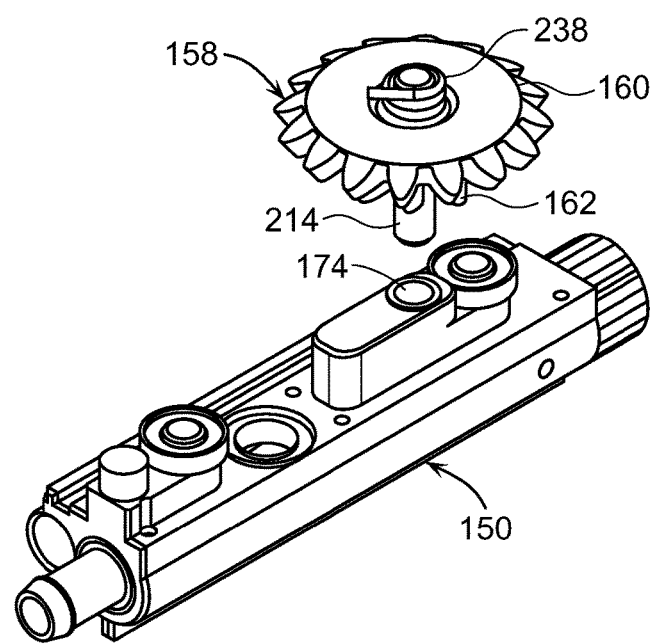
FIG. 22 is a perspective view of the components shown in FIG. 21 in assembled form, wherein the pin is aligned with a socket of a first locking mechanism of a delivery device of the invention.
Figure 23:
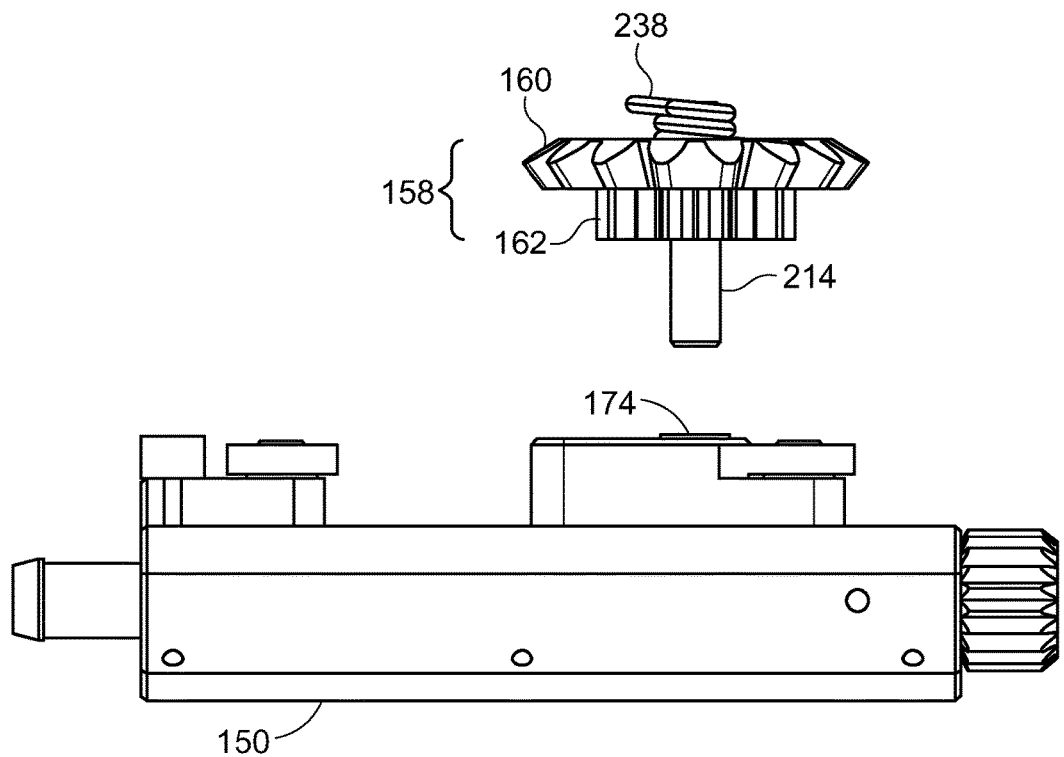
FIG. 23 is a side view of the assemble linking gear, pin, clutches, and aligned first locking mechanism of FIG. 22.
Figure 24:
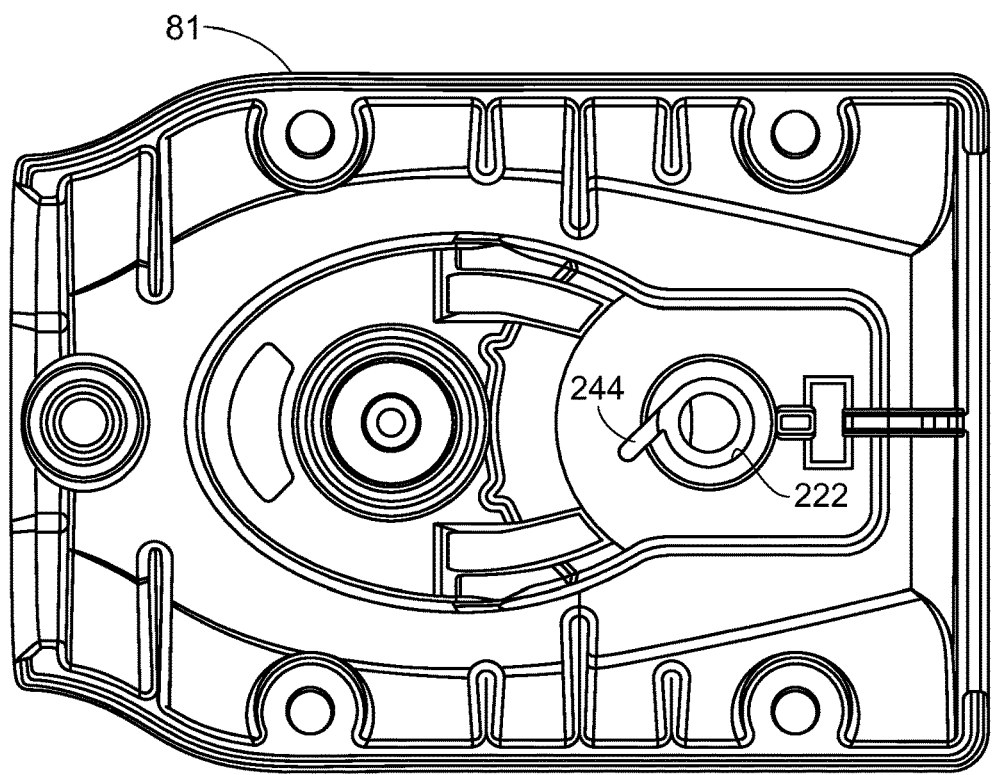
FIG. 24 is a plan view, of the interior portion of a housing component of one embodiment of the delivery device of the invention, indicating the location where an end of the spring coil second clutch would be seated when assembled.

In one specific embodiment of the invention that includes two clutches, FIG. 21 is an exploded of an assembly of the invention that includes a perspective view of pin 214, upper linking gear 160, first clutch 236, which is a one-way needle roller bearing clutch, and second clutch 238, which is a coil spring clutch. When partially assembled, as shown in FIG. 22, first clutch 236 is press-fit into orifice 240 defined by upper linking gear 160 and one end 242 of coil spring 238 is locked to housing 81 a slot 244, shown in FIG. 24. FIG. 23 is a side view of the partial assembly shown in FIG. 22. Pin 214 extends through first clutch 236 and second clutch 238. FIG. 24 is a plan view of housing 81, indicating slot 244 where end 242 of coil spring 238 will be seated upon assembly of linking gear assembly 158, pin 214, coil spring 238 and housing 81. Upon assembly, opposite ends of pin 214 are seated in socket 222 of housing 81 and socket 174 of first locking component housing 150, as described above. During advancement of a vascular prosthesis by clockwise rotation of handle 36, as described above, first clutch 236 will not be engaged, so that upper linking gear 160 and lower linking gear 162 will rotate freely about pin 214. Upon backspin or clockwise rotation of upper linking gear 160, such as by urging of linking gear assembly 158 in a proximal direction by longitudinal expansion of a partially longitudinally-compressed vascular prosthesis, first clutch 236 will lock rotation of pin 214 to that of upper linking gear 160, and rotation of pin 214 within second clutch 238 will loosen clutch about pin 214, while still providing frictional resistance to rotation of pin 214 within second clutch 238. In a preferred embodiment, the force necessary to override the frictional resistance to rotation of pin 214 within first clutch 236 when first clutch 238 is locked is greater than that necessary to overcome the frictional resistance to rotation of pin 214 within second clutch 238 when pin 214 is rotated in the same direction that causes the first clutch 236 to lock.

Figure 26:
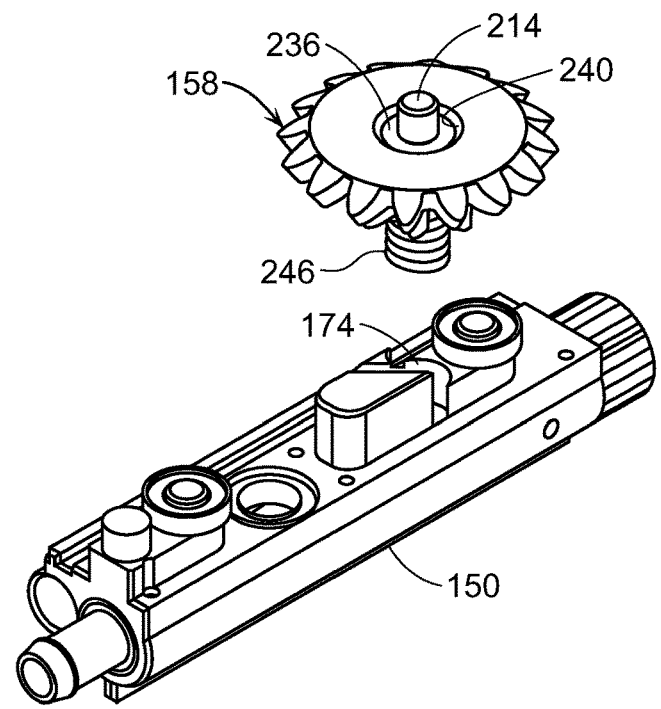
FIG. 26 is perspective view, exploded in part, of the linking gear assembly of FIG. 25 in combination with a first locking component housing of the invention.
Figure 27:
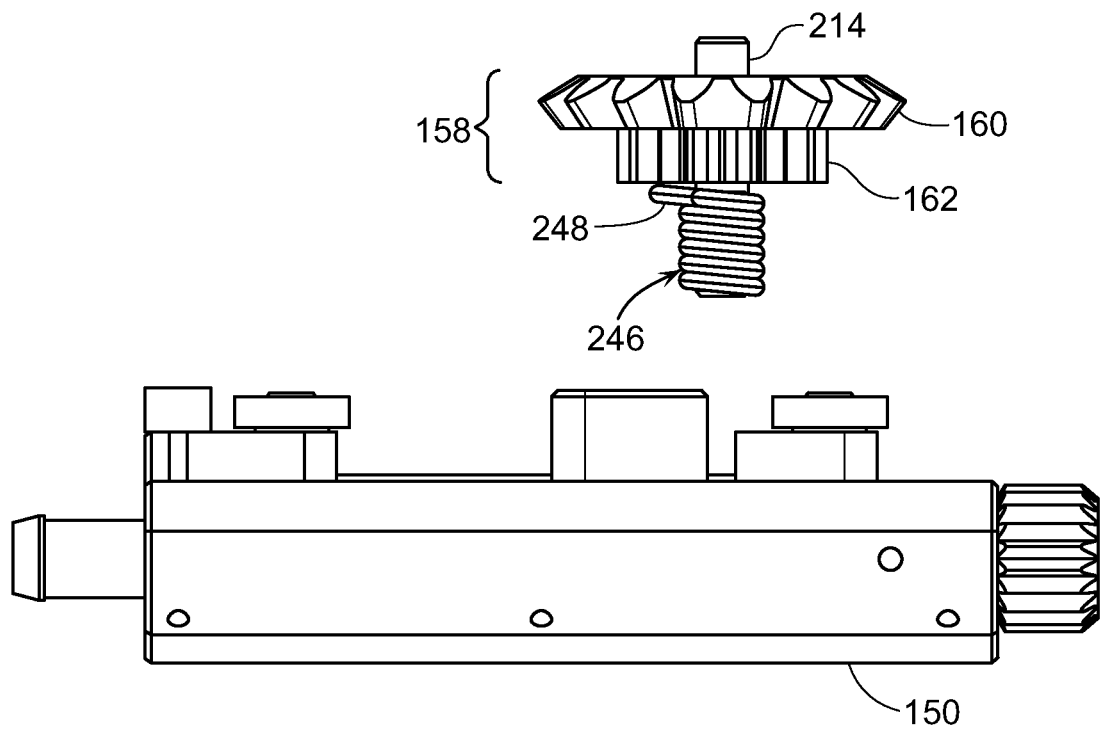
FIG. 27 is a side view of the combination of the linking gear assembly and first locking component housing of FIG. 26.
Figure 28:
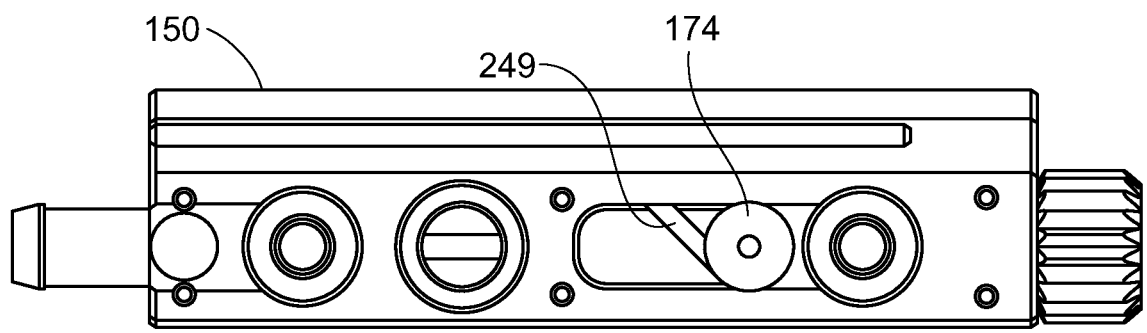
FIG. 28 is a plan view of the first locking component housing of FIG. 27.

In another specific embodiment of the invention that includes two clutches, FIG. 25 is an exploded view of assembly of the invention that includes a perspective view of pin 214, linking gear assembly 158, first clutch 236 that is a one-way needle roller bearing clutch, and second clutch 246 that is a coil spring. When at least partially assembled, first clutch 236 is press-fit into orifice 240 defined by upper linking gear 160, and coil spring 246 extends about one end of pin 214, as shown in FIG. 25. One end 248 of coil spring 246 is locked to first locking component housing 150, as shown in FIG. 26, which is a perspective view of a combination of the partial assembly of FIG. 25 in assembled form. FIG. 27 is a side view of the embodiment shown in FIGS. 25 and 26. FIG. 28, is a plan view of first locking component housing 150, showing socket 174 and slot 247 into which end 248 of coil spring 246 fits. Pin 214 extends through first clutch 236 and second clutch 246, as shown in FIG. 26. FIG. 28 is a side view of the partial assembly of FIG. 26. One end of pin 214 and coil spring 246 can be seated, when fully assemble, in socket 174 of first locking component housing 150. The opposite end of pin 214 is seated in socket 222 of housing 81 (FIG. 17) as described above. During advancement of a vascular prosthesis by clockwise rotation of handle 36, as described above, first clutch 236 will not be engaged, so that linking gear assembly 158 will rotate freely about pin 214. Upon backspin or clockwise rotation of upper linking gear, first clutch 236 will lock rotation of pin 214 to that of upper linking gear 160, and rotation of pin 214 within second clutch 238 will loosen second clutch (a coil spring, as shown in FIGS. 25-28) 238 about pin 214, while still providing frictional resistance to rotation of pin 238. In a preferred embodiment, the force necessary to override the frictional resistance to rotation of pin 214 within first clutch (which is the one-way needle roller bearing clutch) 236 when first clutch 236 is locked is greater than that necessary to overcome the frictional resistance to rotation of pin 214 within the second clutch 238 when the pin 214 is rotated in the same direction that causes the first clutch 236 to lock.

Figure 29:
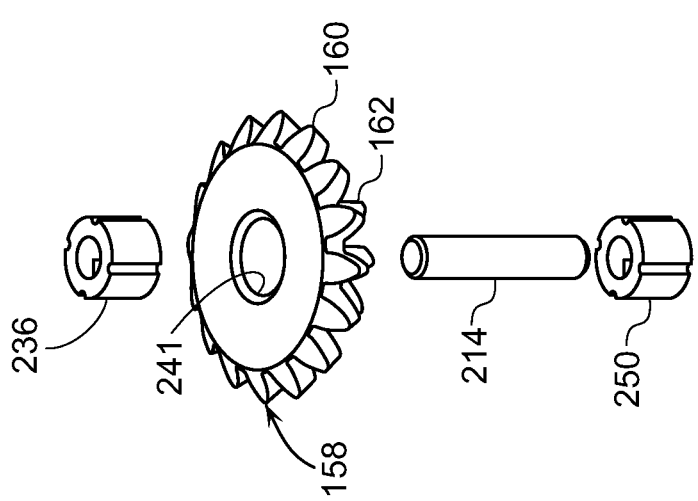
FIG. 29 is an exploded view of another embodiment of a linking gear assembly of the invention including two one-way needle roller needle bearing clutches.

In yet another specific embodiment of the invention that includes two clutches, FIG. 29 is an exploded view of another assembly of the invention that includes a perspective view of pin 214, linking gear assembly 158, first clutch 236, that is a one-way needle roller bearing clutch, and second clutch 250, that is a one-way needle roller bearing clutch. In another embodiment, first clutch 236 and second clutch 250 are both disengaged during distal advancement and engaged when directed in a proximal direction. In this alternative embodiment, the force necessary to override the frictional resistance to rotation of pin 214 within first clutch 236 when first clutch 236 is locked can be greater than that necessary to overcome the frictional resistance to rotation of pin 214 within second clutch 250 when pin 214 is rotated in a direction that causes first clutch 236 to lock.

Figure 30:
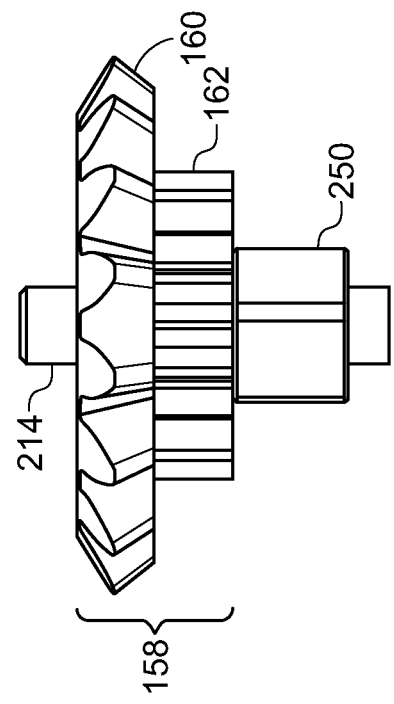
FIG. 30 is a side view of the linking gear assembly of the invention shown in FIG. 29 when assembled.

When assembled, as shown in FIG. 30, first clutch 236 is press-fit into orifice 241 of upper linking gear 160 and second one-way needle roller bearing clutch 250 is press-fit into socket 174 of first locking component housing 150 (FIG. 18). It is to be understood that the positions of the first and second one-way needle roller bearing clutches can be reversed. Pin 214 extends through first clutch and second clutch. Opposite ends of pin 214 are seated in socket 222 of housing 81 (FIG. 17) and second one-way needle roller bearing clutch 250. During advancement of a vascular prosthesis by clockwise rotation of handle 36, as described above, first one-way needle roller bearing clutch 236 will not be engaged, but the torque applied to proximal handle by the surgeon will be sufficient to override the frictional resistance provided to pin 214 by second one-way needle roller bearing clutch 250. The frictional resistance can be a consequence of friction between second one-way needle roller bearing clutch 250 and socket 174 of first locking component housing 150, or between the needles of second one-way needle roller bearing clutch 250 and pin 214. Upon backspin or clockwise rotation of upper linking gear 160 (or linking gear assembly 158), first clutch 236 will lock rotation of pin 214 to that of upper linking gear 160, and rotation of rotation of pin 214 within second clutch 250 will unlock second clutch 250 from pin 214. In one embodiment, the surgeon can rotate proximal handle 36 in a direction to retract a vascular prosthesis by overriding the frictional force provided by first one-way needle roller bearing clutch 236. The frictional force can be, for example, at least one of that between the first one-way needle roller bearing clutch 236 and orifice 241 of linking gear assembly 158 into which it is press-fit, and between the needle rollers of the one-way needle roller clutch 236 and pin 214. In a preferred embodiment, the force necessary to override the frictional resistance to rotation of pin 214 within first clutch 236 when first clutch 236 is locked is greater than that necessary to overcome the frictional resistance to rotation of pin 214 within the second clutch 250 when pin 214 is rotated in the direction that causes the first clutch 236 to lock. The relative torque force required to override the friction between pin 214 and the first one-way needle roller clutch 236 and second one-way needle roller clutch 250 can be manipulated, for example, by employing metal needle rollers in first one-way needle roller bearing clutch 236 and plastic needles in second one-way needle roller bearing clutch 250.

FIG. 31 is a perspective view of actuator 80 of FIG. 1 (without housing 81 or pushbutton 82), of first locking component housing 150 and second locking component housing 152. Coil spring 210, as a clutch that extends about pin 214. End 218 of coil spring 210 is seated within recess of upper linking gear. This embodiment of pin 214, clutch 210, linking gear assembly 158 and first locking component housing 150 is the same as that shown in FIG. 16.

Figure 33:
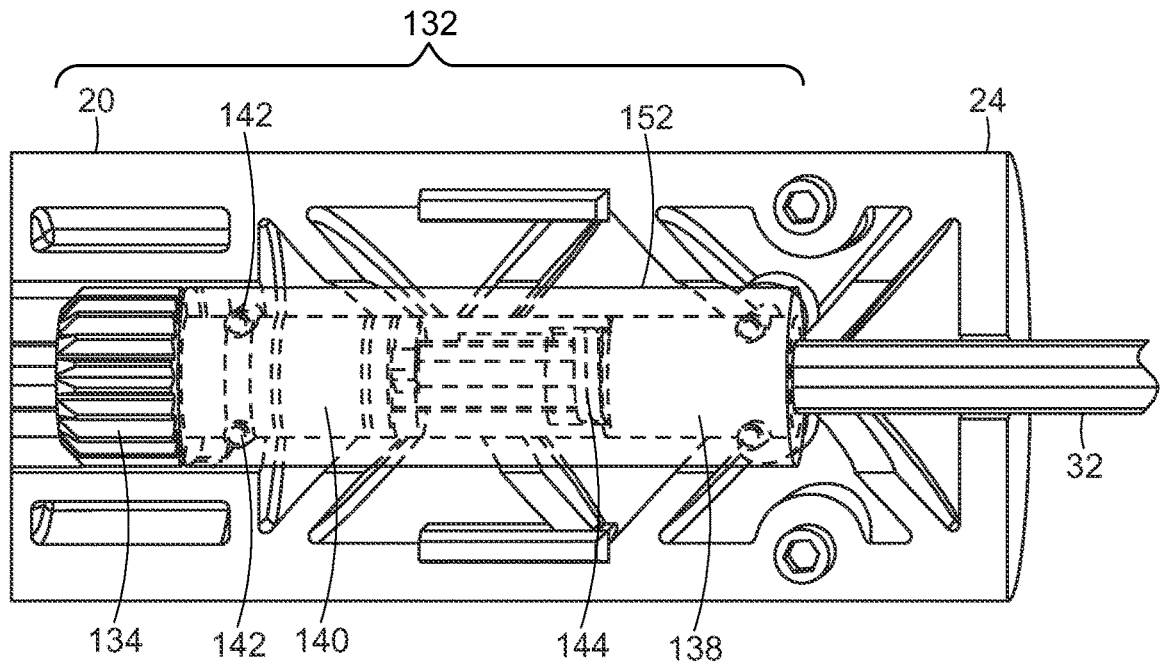
FIG. 33 is a partial cutaway of the distal end of handle body and second locking component shown in FIGS. 31 and 32.
Figure 34:
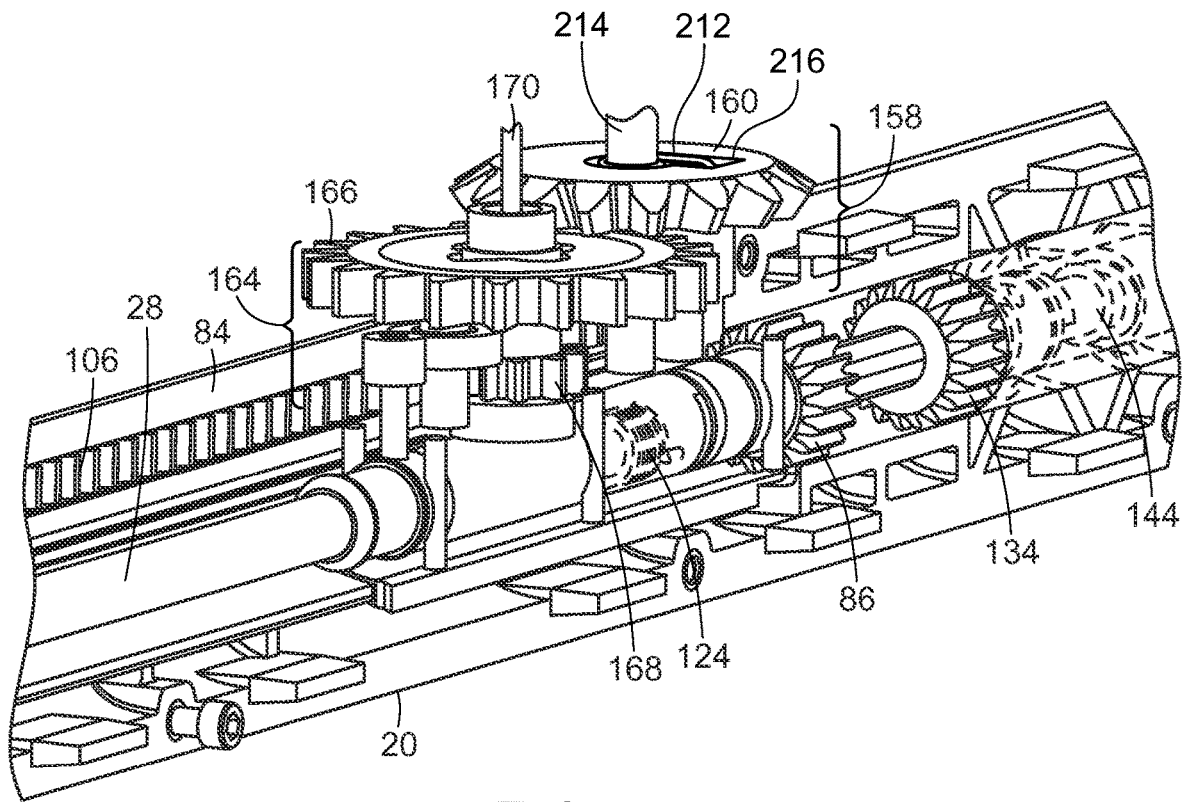
FIG. 34 is a perspective view of a partial cutaway of the actuator shown in FIG. 32.

In another embodiment, shown in FIG. 32, which employs the assembly shown in FIGS. 25-28, upper pinion gear 166 is coaxial with lower pinion gear 168 which, in turn, engages gear rack 106. As shown therein, first clutch is a one-way needle roller bearing clutch 236 that is press-fit into orifice 240 defined by linking gear assembly 158, and second clutch is a coil spring 246 that is seated in socket 174, and through which pin 214 extends. In both embodiments of FIGS. 31 and 32, delivery catheter 28 is linked to first locking component housing 150 and, thus, will move longitudinally along housing 150, with movement of proximal handle 36 and actuator 80, as shown in FIG. 1, regardless of whether first locking component 124 (FIG. 19) is engaged with push rod 32 (FIGS. 33 and 34). Therefore, when upper pinion gear 166 engages lower pinion gear 168, rotation of proximal handle 36 (as shown in FIG. 1) about handle body 20 will cause rotation of linking gear assembly 158 (FIGS. 1 and 34) and, consequently, rotation of pinion gear assembly 164 (FIG. 34) and movement of pinion gear assembly 164 along gear rack 106 (FIGS. 31, 32, and 34), and movement of proximal handle 36 (FIG. 1) and actuator 80 (FIGS. 12A and 12B) along handle body 20. Further, while first locking component 124 (FIGS. 10, 11, 33, and 34) is engaged with push rod 32, rotation of proximal handle 36 will cause longitudinal movement of push rod 32 along handle body 20. In all cases, movement of proximal handle 36 and actuator 80 along handle body 20 will always occur together, and will cause movement of delivery catheter 28 longitudinally along handle body 20.

However, as will be further explained below, depression of center pin 170 disengages upper pinion gear 166 from lower pinion gear 168. When upper pinion gear 166 is disengaged from lower pinion gear 168, rotation of proximal handle 36 about handle body 20 does not cause longitudinal movement of the proximal handle 36 and actuator 80 along handle body 20. Further, longitudinal movement of proximal handle 36 and actuator 80 along handle body 20 can be obtained simply by moving proximal handle 36 and actuator 80 along handle body 20 without rotation of proximal handle 36 about handle body 20 (FIGS. 1, 12A and 12B).

FIG. 34 is another perspective view of linking gear assembly 158 and pinion gear assembly 164 of actuator 80 (FIGS. 1 and 31).

Figure 35:
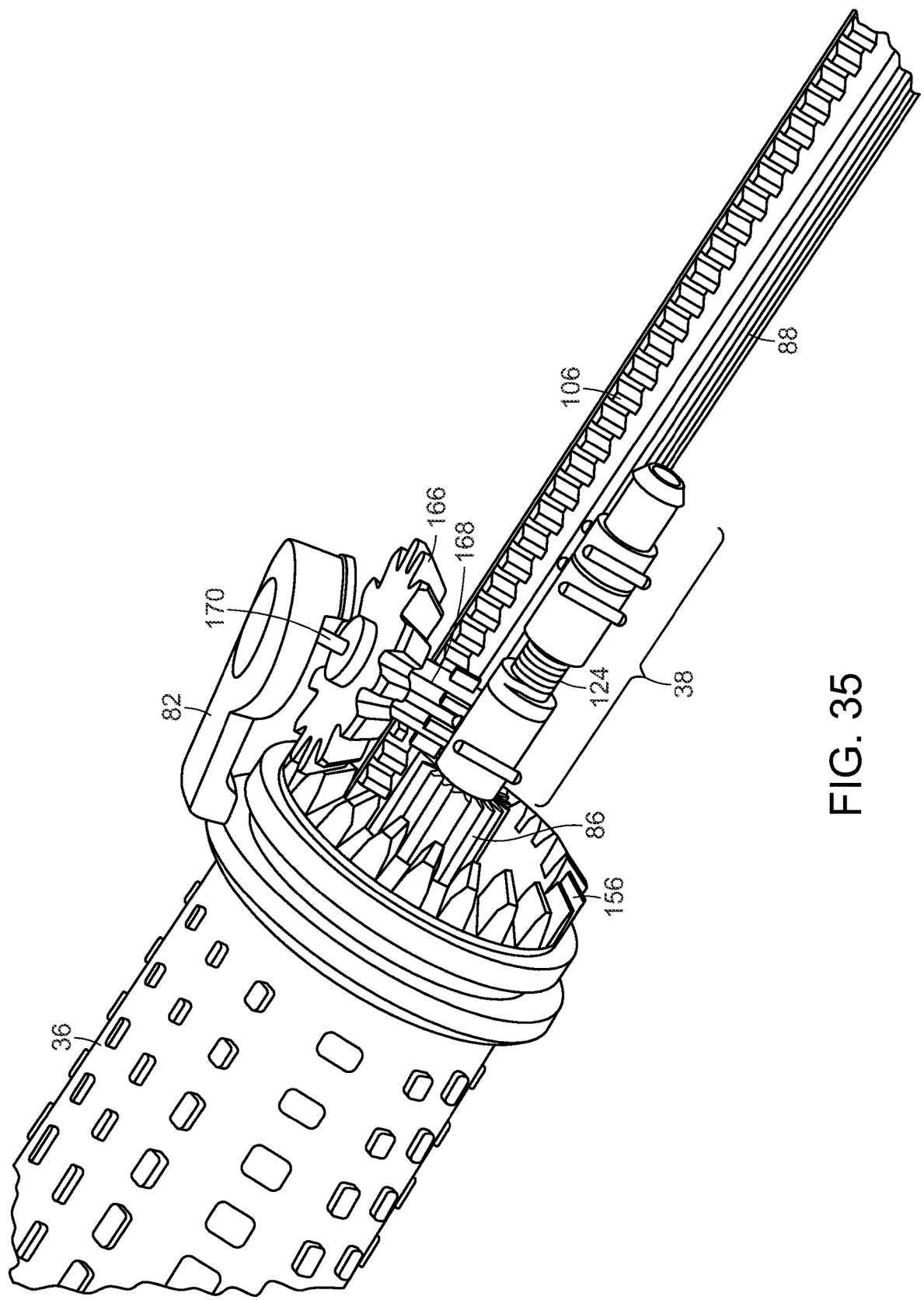
FIG. 35 is a perspective view of a rack and proximal handle of the embodiment shown in FIG. 1, and an alternate embodiment of the actuator of the invention, lacking a linking gear assembly.

As an alternative embodiment, shown in FIG. 35, push button 82 rests atop center-pin 170, which extends through upper pinion gear 166. As can also be seen in FIGS. 35 and 36, lower pinion gear 168 is engaged with gear rack 106 and includes pinion gear extension 265 that is axially aligned with lower pinion gear 168 that is axially aligned with upper pinion gear 166. Lower portion 172 of pinion gear 168 extends into opening 174 (FIG. 11) defined by first locking component housing 150 (FIG. 11), thereby fixing the position of pinion gear assembly 164 relative to first locking component housing 150 (FIG. 11), distal bearing 120 (FIG. 11), first locking component 124 and drive gear 86, all of which are shown, in a previous embodiment, in FIG. 11.

Figure 36:
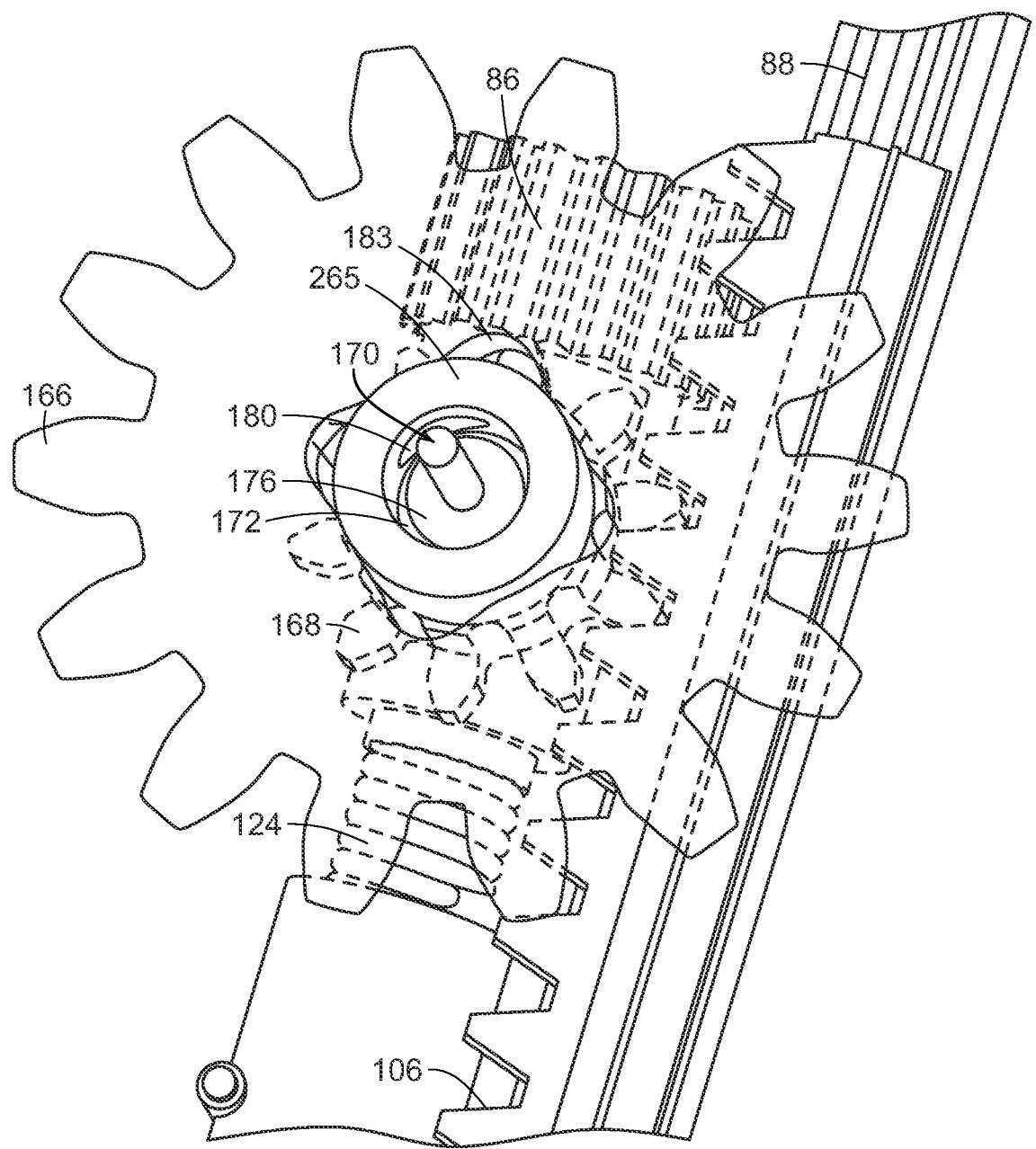
FIG. 36 is a perspective view, partially transparent, of the embodiment of the pinion gear assembly of FIG. 35.
Figure 37:
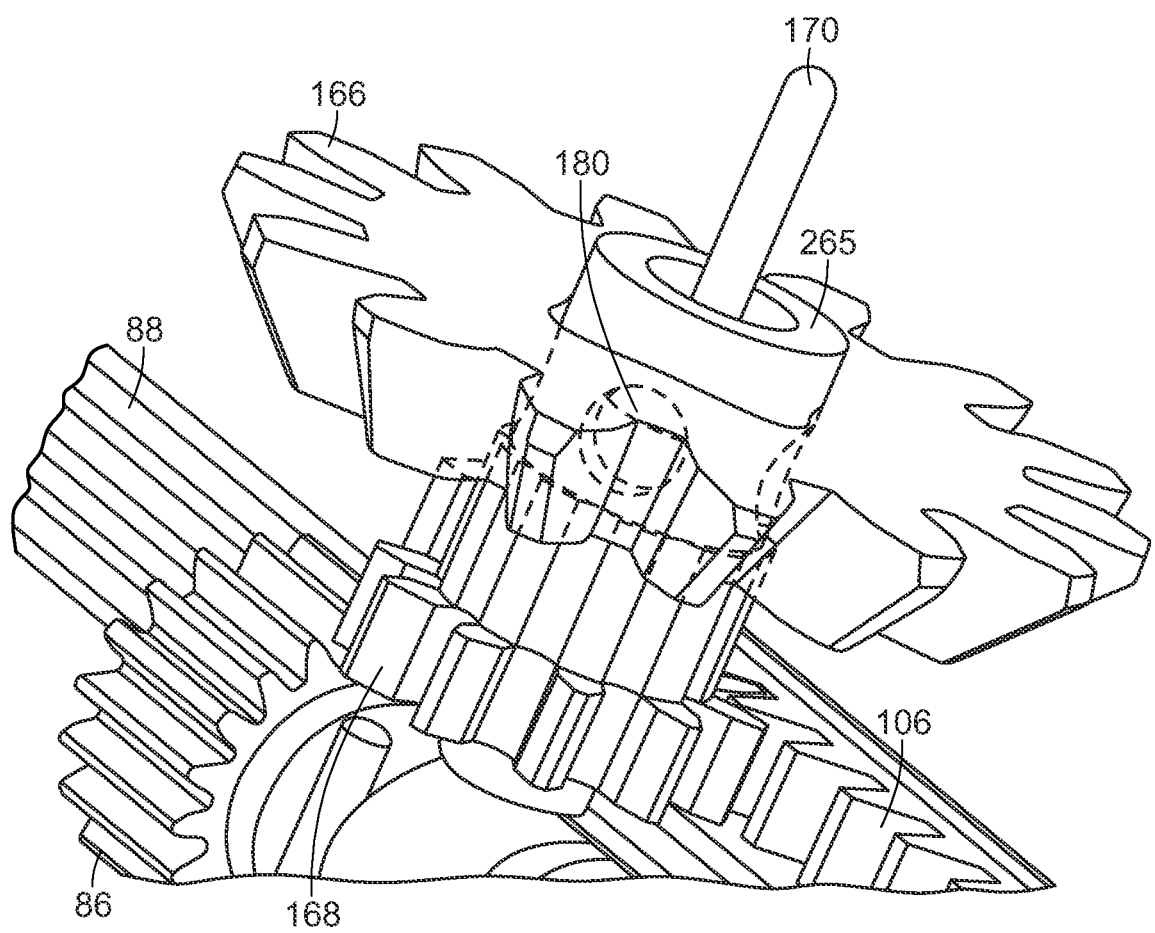
FIG. 37 is another view of the embodiment represented in FIG. 36.
Figure 38:
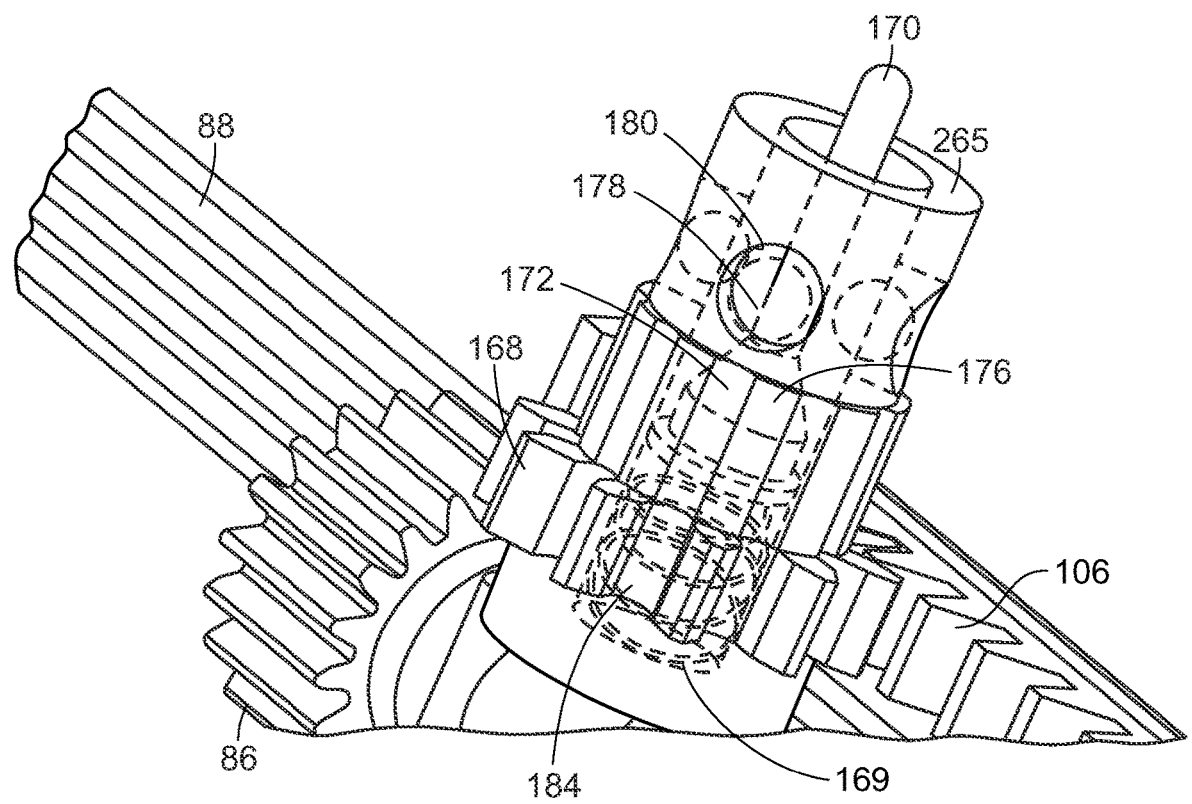
FIG. 38 is a perspective view of the embodiment shown in FIGS. 36 and 37, lacking the upper pinion gear shown in those figures.
Figure 39:
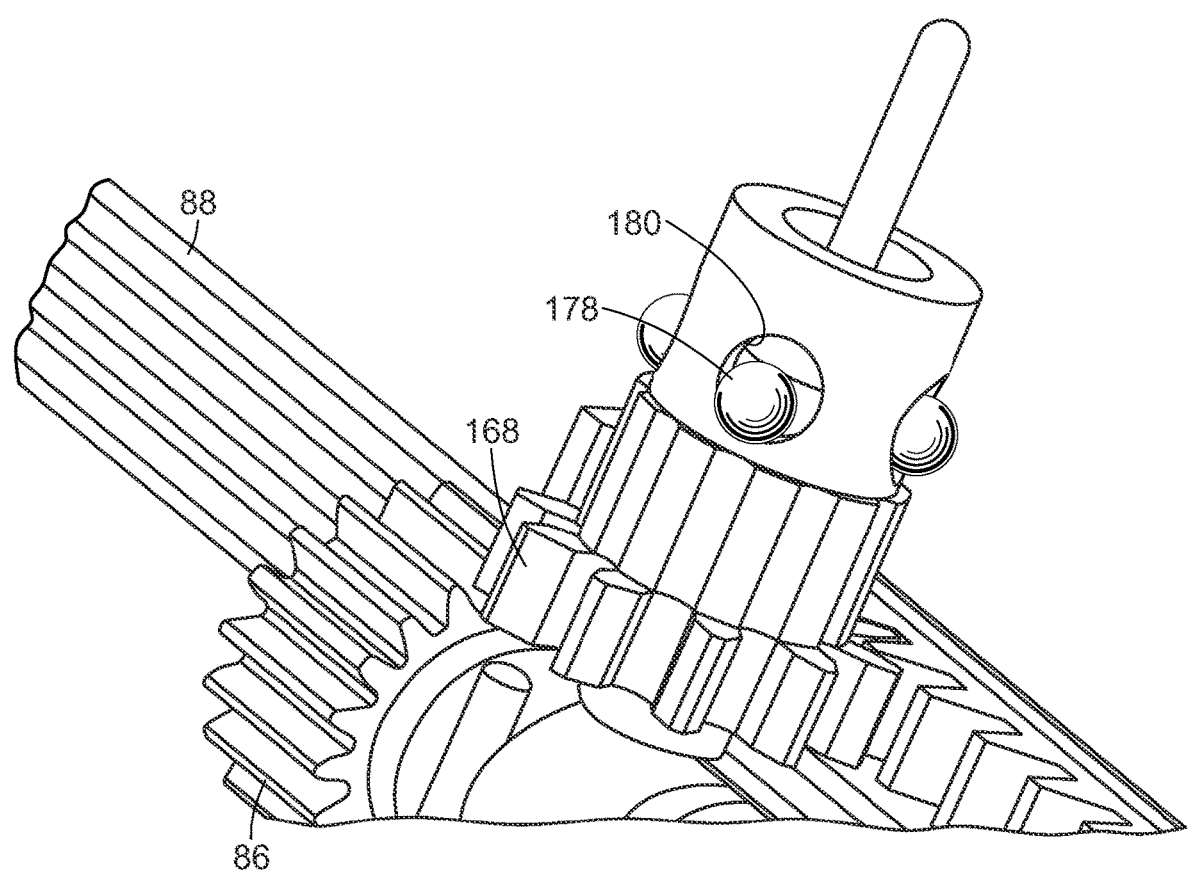
FIG. 39 is another embodiment of the representation shown in FIG. 38.

FIG. 36 is a perspective view showing engagement of lower pinion gear 168 with gear rack 106 and frustoconical portion 176 of center-pin 170. As can be seen in FIGS. 37 and 38, ball bearings 178 extend through side openings 180 defined by pinion gear extension 265 and, when center pin 170 is in an extended position, as shown in FIG. 37, frustoconical portion 176 of center pin 170 forces ball bearings 178 outwardly and into interfering relation with interference openings 183, which is defined by side openings 183 and upper pinion gear orifice 182 (FIG. 36). Upper pinion gear orifice 182 is defined by upper pinion gear 166 (FIGS. 36 and 37). When interference openings 183 are occupied by ball bearings 178, upper pinion gear 166 is engaged with lower pinion gear 168.

Figure 40A:
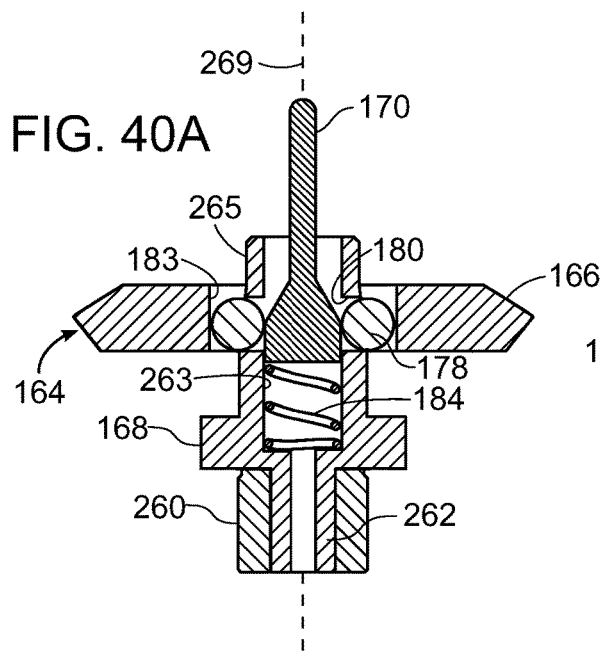
FIG. 40A is a cross-sectional view of the pinion gear assembly of FIGS. 36 through 39, wherein a pin has not been depressed, thereby causing the upper pinion gear and lower pinion gear to be in interfering relation to each other by radially outward displacement of ball bearings, and further showing a lower extension of a lower pinion gear of the pinion gear assembly, and a one-way needle roller clutch in which the lower extension is seated.
Figure 40B:
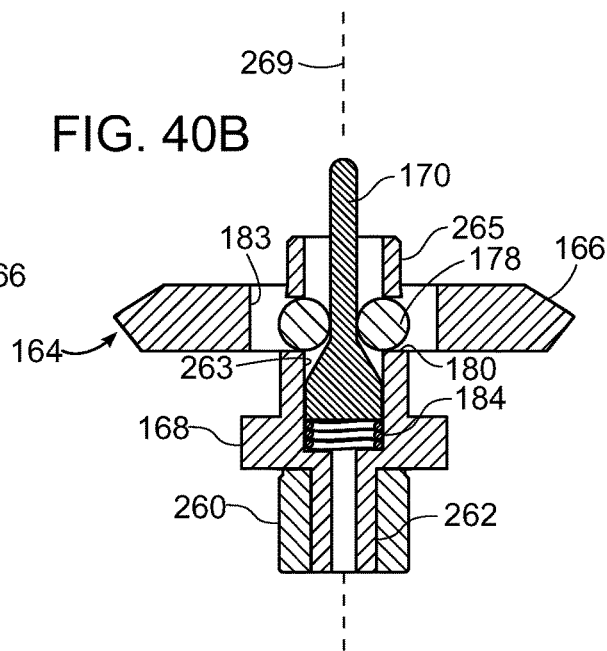
FIG. 40B is a cross-sectional view of the pinion gear assembly of FIG. 40A, wherein a center pin has been depressed, thereby compressing a biasing spring and allowing independent rotation of upper and lower pinion gears by removal of radially outward displacement of ball bearings that otherwise would cause the interfering relationship of independent rotation of the upper and lower pinion gears.
Figure 40C:
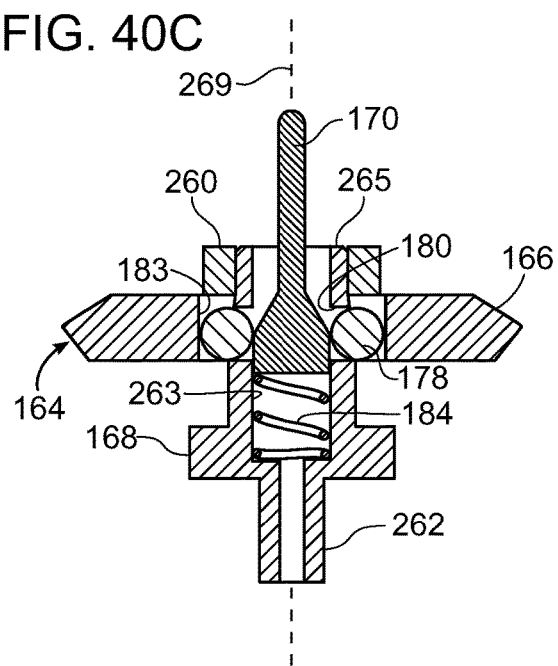
FIG. 40C is a cross-sectional view of the pinion gear assembly of FIGS. 36 through 39, wherein a pin has not been depressed, thereby causing the upper pinion gear and lower pinion gear to be in interfering relation to each other by radially outward displacement of ball bearings, and further showing an upper extension of a lower pinion gear of the pinion gear assembly, and a one-way needle roller clutch in which the upper extension is seated.
Figure 40D:
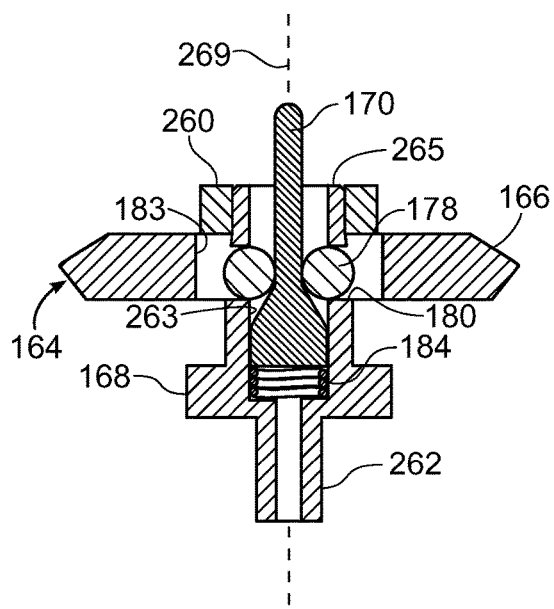
FIG. 40D is a cross-sectional view of the pinion gear assembly of FIG. 40C, wherein a center pin has been depressed, thereby compressing a biasing spring and allowing independent rotation of upper and lower pinion gears by removal of radially outward displacement of ball bearings that otherwise would cause the interfering relationship of independent rotation of the upper and lower pinion gears.

As can be seen in the transition from FIG. 40A to 40B, when center pin 170 is actuated by depressing button 82 (FIG. 1), center pin 170 moves within lower pinion gear orifice 263, and ball bearings 178 are forced inward through side openings 180 of pinion gear 265 by rotation of upper pinion gear 166 relative to lower pinion gear 168 about axis 269, whereby upper pinion gear 166 is no longer engaged with lower pinion gear 168. Centerpin 170 is biased in an outward position by biasing spring 184 and frustoconical portion 176, whereby upper pinion gear 166 is directed into engagement with lower pinion gear 168 by spring 184 located at the base of center pin 170 within pinion gear extension orifice 263 of pinion gear extension 265. As can be seen at FIGS. 40A and 40B, clutch 260 is at lower extension 262, in which case clutch 260 would be seated in socket 174, not shown, as explained below. In another embodiment, shown in FIGS. 40B and 40C, clutch is at pinion gear 265 above lower pinion gear 164. In this embodiment, clutch 260 would be seated in a socket (not shown) at an opening of housing 81 through which center pin 170 extends.

Figure 42:
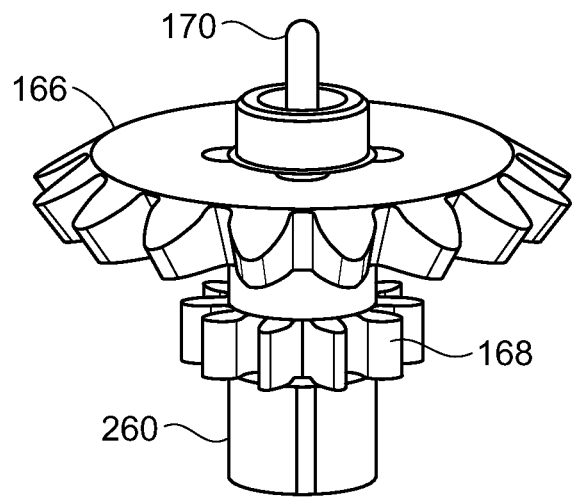
FIG. 42 is a perspective view of the linking gear assembly of FIGS. 40 and 41 in perspective.
Figure 43:
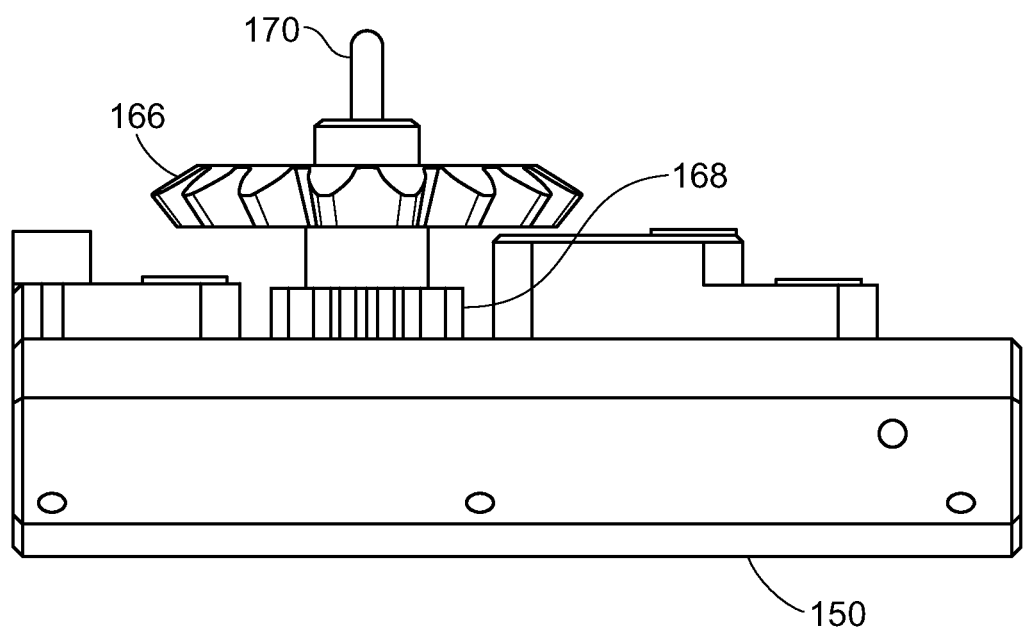
FIG. 43 is a side view of the assembled linking gear assembly of FIG. 40 through 42 when assembled with the first locking mechanism of FIG. 41.

FIG. 41 is an exploded view of the embodiment shown in FIGS. 35 through 40A and B, showing one-way needle roller bearing clutch 260 at lower extension 262 of pinion gear assembly 164. Lower extension 262 is located within one-way needle roller bearing clutch 260 which, in turn is seated, such as by being press-fit, into socket 174, shown in FIG. 41 of first locking component housing 150. A side view of pinion gear assembly 164 when assembled with one-way needle roller bearing clutch 260 and first locking mechanism 38, is shown in FIG. 43. During use, the surgeon can depress center pin 170 to compress biasing spring 184 and release ball bearings 178 from outward disposition by releasing frustoconical portion 176 of center pin 170, to thereby disengage lower pinion gear 168 from upper pinion gear 166. By doing so, the surgeon can advance a vascular prosthesis to be delivered by the delivery device of the invention to a position distal to the surgical site without rotating proximal handle 36, whereby lower pinion gear 168 (FIGS. 40-42) will continue to rotate because it continues to be engaged with pinion rack 106 (FIGS. 36-38). However, because upper pinion gear 166 is disengaged from lower pinion gear 168, upper pinion gear 166 will not rotate during longitudinal movement of proximal handle 36 and first locking mechanism 38 along handle body 20. If the surgeon releases proximal handle 36, or pulls handle 36 in a proximal direction (toward the surgeon), lower pinion gear 168 will spin in an opposite direction to that of longitudinal advancement of the vascular prosthesis. Rotation of lower pinion gear 168 in the opposite direction of advancement of vascular prosthesis, will cause one-way needle roller bearing clutch 260 will lock to lock onto lower extension 262, thereby providing resistance to further rotation of lower pinion gear 168 and, consequently, further proximal longitudinal movement of first locking mechanism 38 and the vascular prosthesis toward the surgeon. The resistance to further rotation of the lower pinion gear can be overcome by the surgeon pulling on proximal handle 36 in a proximal direction. Alternatively, proximal handle 36 can be rotated in a counterclockwise direction wherein lower pinion gear extension 262 slips rotationally within the clutch needle rollers so that the resistance to rotation is greater within the interference fit of clutch 260 and socket 174. The resistance to further rotation is friction between at least the one-way needle roller bearing clutch 260 and at least one of socket 1744 in which one-way needle roller bearing clutch 260 is press-fit and lower extension 262 of lower pinion gear 168 which is seated in one-way needle roller bearing clutch 260. Upon approach of vascular prosthesis to the surgical site where the vascular prosthesis is to be deployed, the surgeon can release center pin 170 to thereby reengage upper pinion gear 168 with lower pinion gear 166.

Once upper pinion gear 166 is reengaged with lower pinion gear 168, and proximal handle 36 (e.g. FIG. 1) is rotated in a direction, such as a clockwise direction from the surgeon's point of view, the vascular prosthesis can be advanced to a surgical site in a more controlled manner. During advancement of the vascular prosthesis by rotation of proximal handle 36, the vascular prosthesis typically is longitudinally compressed by within delivery device 10. If the surgeon releases proximal handle 36, the vascular prosthesis will exert a proximal longitudinal force (toward the surgeon) on first locking mechanism 36 and, consequently, linking gear assembly 158. Proximal longitudinal force on pinion gear assembly 164 will prompt rotation of lower pinion gear 168 because it is engaged with gear rack 106, thereby causing one-way needle roller bearing clutch 260 to lock onto lower extension 262 of lower pinion gear 168, preventing further rotation in the same direction. Also, lower pinion gear 168 and upper pinion gear 166 are locked because center pin 170 is not actuated, causing ball bearings 178 to be in interfering relation with rotation of upper pinion gear 166, thus preventing backspin of proximal handle 36 in a direction opposite to that of longitudinal advancement of the vascular prosthesis toward the surgical site, and preventing longitudinal expansion of the vascular prosthesis caused by relaxation of longitudinal compression of the vascular prosthesis, such as could be the result of the surgeon releasing the proximal handle 36 after rotation by the surgeon in a direction, such as a clockwise direction to advance the vascular prosthesis to a surgical site. The surgeon can override the friction between one-way needle roller bearing clutch 260 and at least one of socket 174 and lower extension 262 of lower pinion gear 168 by rotating proximal handle 36 in a direction opposite to that which causes advancement, such as a counter clockwise direction. At any time before or after approaching the surgical site, center pin 170 can be depressed to disengage lower pinion gear 168 from upper pinion gear 166, thereby again allowing the surgeon to longitudinally advance or retract the vascular prosthesis by directing proximal handle 36 distally or proximally without rotation of proximal handle 36.

As can be seen in FIG. 46A, nose cone 50 is fixed to guidewire catheter 12 at a distal end 16 of the guidewire catheter 12. Vascular prosthetic component 58 is disposed within delivery device 10 proximal to nose cone 50.

Figure 44:
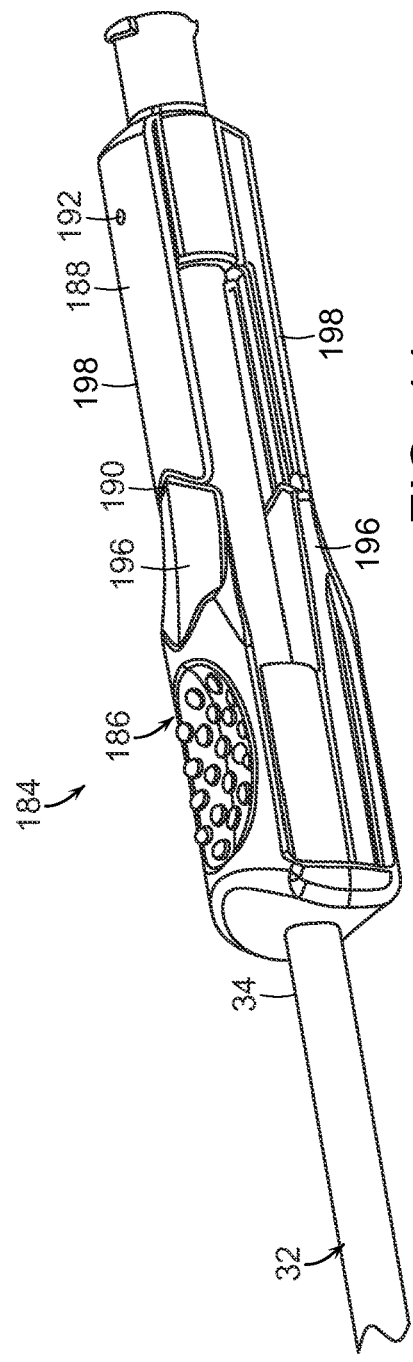
FIG. 44 is a perspective view of one embodiment of a proximal clasp assembly of one embodiment of the invention.
Figure 45:
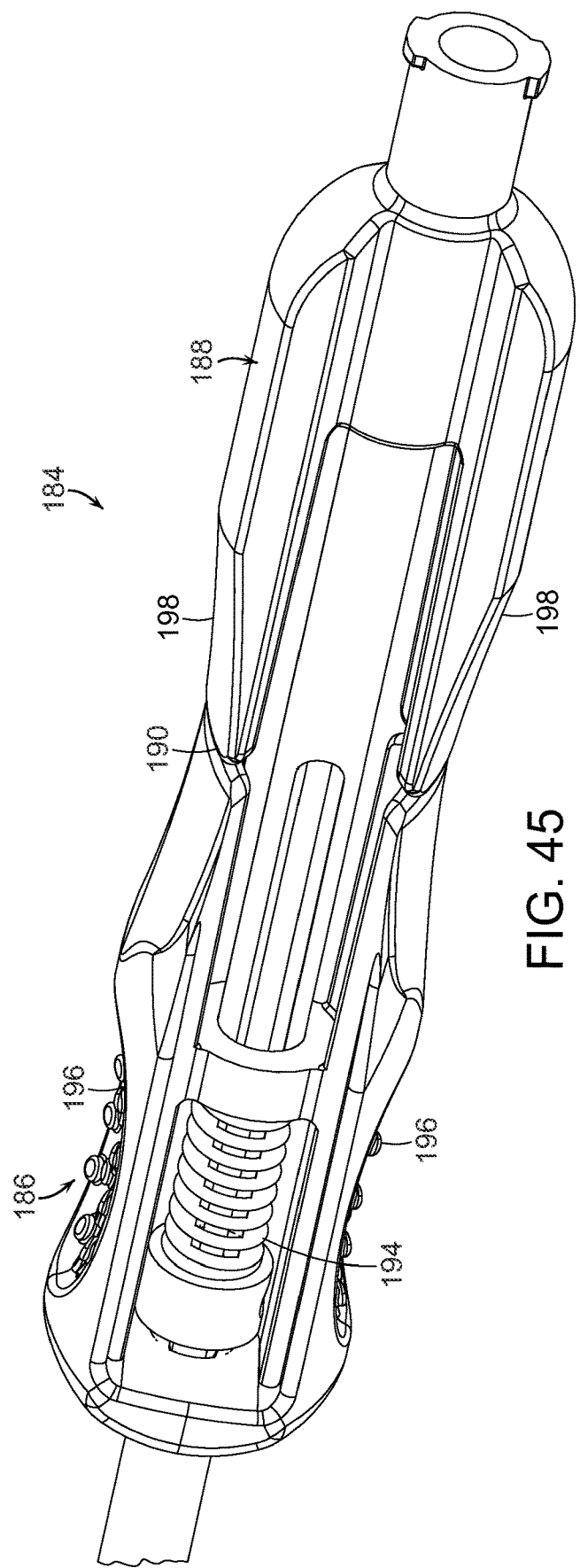
FIG. 45 is a partial cutaway of the proximal clasp assembly shown in FIG. 44.

FIGS. 44 and 45 show perspective and cut-away views, respectively, of the proximal clasp assembly 184 component of the invention. As can be seen in FIG. 44, outer coupling 186 is slideable along proximal end 34 of push rod 32. Fixed component 188 is fixed to the proximal end of the guidewire catheter by pin 192. Outer coupling 186 and fixed component 188 are in mating relation at juncture 190. Spring 194 within outer coupling 186 biases outer coupling 186 against fixed component 188. Proximal clasp assembly 184 is moved from a first position, shown in FIGS. 44, 47B to a second position, shown by applying pressure to tongues 196 on either side of outer coupling 186, and directing outer coupling 186 distally in sufficient degree to allow rotation of outer coupling 186 ninety (90) degrees and then retracting outer coupling 186 so that tongues 196 of outer coupling 186 align between tongues 198 of fixed component 188, as shown in FIG. 51B. Movement of outer coupling 186 from the first position, shown in FIG. 44, to the position shown in FIG. 51B, causes opening of apex clasp assembly 52, whereby proximal capture component is retracted from a first position that is in mating relation to the distal capture component 56 of apex clasp assembly 52 shown in FIG. 50B, to a second position, shown in FIG. 51C, wherein proximal capture component 54 is no longer in mating relation with distal capture component 56. Proximal movement of outer coupling 186 of proximal clasp assembly 184 (FIGS. 44, 47B, 51B) relative to a fixed component 188 to separate proximal capture component 54 (FIG. 50B) from distal capture component 56 (FIGS. 50B, 51C) releases apices 68 of stent 66 at proximal end 60 of vascular prosthetic component 58.

FIGS. 46A-46C are cross sectional views of a portion of delivery device 10 of the invention showing a vascular prosthetic component 58 in an undeployed state within a distal end 202 of delivery device 10. Specifically, as shown in FIG. 46A, vascular prosthetic component 58 is within delivery sheath 200. Distal end 62 of vascular prosthetic component 58 abuts buttress 204. Buttress 204, in turn, is mated to push rod 32 at distal end 206, proximal end 60 of vascular prosthetic component 58 captured at apices 68 of proximal stent 66 with apex clasp assembly 52 when apex clasp assembly 52 is in a closed position, as shown in FIG. 46A. Apex class assembly 52 includes distal capture component 56 at distal end 16 of guidewire catheter 12, and proximal capture component 54 is in mateable relation to distal capture component 56, and attached to distal end 210 of apex release catheter 154. Apex release catheter 154 extends about guidewire catheter 12, and both apex release catheter 154 and guidewire catheter 12 extend through vascular prosthetic component 58 and push rod 32 to proximal clasp assembly 184 (FIG. 45). Delivery sheath 200 is fixed at its proximal end to delivery catheter 28 at distal end 30 and extends about vascular prosthetic component 58 to apex clasp assembly 52, as can be seen in FIG. 46C. Returning to FIG. 46A, nose cone 50 is fixed at guidewire catheter 12 distally to distal capture component 56 of apex clasp assembly 52. Outer catheter 48 extends from distal handle nose 44 (FIG. 1), and about delivery catheter 28 and delivery sheath 200, to nose cone 50.

As shown in FIGS. 47A-52B, a method for delivering a vascular prosthesis to a treatment site of the subject employing a delivery device of the invention includes advancing vascular prosthesis 58, while prosthesis 58 is mounted to apex clasp assembly 52 at proximal end 60 of the prosthesis 58. Proximal apex clasp assembly 184 is in a first position shown in FIG. 47B, whereby apex clasp assembly 52 is closed (FIG. 50B). Apices of vascular prosthesis 58 are secured at apex clasp assembly 52 when proximal clasp assembly 184 is in the first position. Apex clasp assembly 52 is, in turn, fixed to distal end 16 of guidewire catheter 12, shifting knob 42 is in a first position when pin 108 is in slot 110 (FIG. 47C), causing push rod 32 to move with longitudinal movement of proximal handle 36. Prosthesis 58 is advanced to a position distal to a vascular treatment site of the subject by rotation of proximal handle 36 in a first direction about handle body 20, having distal end 26, of delivery device 10 through which guidewire catheter 12 extends. Guidewire catheter 12 is disposed within push rod 32 that also extends through handle body 20, wherein guidewire catheter 12 is fixed to push rod 32, such as at a proximal end of guidewire catheter 12 or push rod 32 by pin 192 (FIG. 44), whereby rotation of proximal handle 36 causes longitudinal movement of guidewire catheter 12 and push rod 32 along handle body 20 to thereby at least partially advance prosthesis 58 from outer catheter 48 as can be seen in FIGS. 48A-48B. Optionally, push button 82 of actuator 80 can be depressed to disengage rotation of proximal handle 36 from longitudinal movement of proximal handle 36 along handle body 20, to thereby allow manual advancement of vascular prosthesis 58 to the vascular treatment site of the subject without rotation of proximal handle 36 about handle body 20.

Shifting knob 42 is shifted from a first position, wherein first locking component 124 (FIGS. 10, 11) secures proximal handle 36 to push rod 32, to a second position, whereby first locking component 124 (FIGS. 10, 11) disengages proximal handle 36 from push rod 32 and second locking component 144 (FIGS. 10, 11) engages push rod 32 with handle body 20 at proximal end 24 of handle body 20.

As can be seen in FIGS. 50A and 50B, proximal handle 36 can then be rotated in a second direction, while actuator push button 82 is not depressed, whereby delivery catheter 28, having a distal end 30 (FIG. 53A) and extending about push rod 32, is withdrawn along push rod 32, and delivery sheath 200 extending from distal end of the delivery catheter (FIGS. 4 through 9) is at least partially retracted from about prosthesis 52. Optionally, push-button 82 of actuator 80 can be depressed, thereby disengaging rotation of proximal handle 36 from handle body 20, to thereby fully retract of delivery sheath 200 from vascular prosthesis 58 without rotation of proximal handle 36 about handle body 20, as can be seen in FIG. 51A.

Proximal clasp assembly 184 is then actuated by compressing outer coupling 186 and moving outer coupling 186 first distally, then rotating outer coupling 186 ninety degrees, and thereafter retracting outer coupling 186 to a second position, shown in FIG. 51B, thereby retracting apex release catheter 154 within push rod 32 (FIGS. 10, 11) and retracting proximal capture component 54 from distal capture component 56. Apices 68 of stent 66 at the proximal end 60 of vascular prosthesis 58 are released from apex clasp assembly 52, and prosthesis 58 is thereby released from the delivery device 10, as can be seen in FIG. 51C. Shifting knob 42 is then moved from the second position to the third position, wherein pin 108 is located in slot 114 between first slot 110 and second slot 112, as can be seen in FIG. 52B, thereby disengaging push rod 32 from handle body 20. Push rod 32 and guidewire catheter 12 are then withdrawn from vascular prosthesis 58 by pulling push rod 32 through handle body 20, thereby completing delivery of vascular prosthesis 58 to the treatment site, as can be seen in FIG. 52A.

While this invention has been particularly shown and described with references to example embodiments thereof, it will be understood by those skilled in the art that various changes in form and details may be made therein without departing from the scope of the invention encompassed by the appended claims.

The relevant portion of all references cited herein and U.S. Pat. Nos. 8,070,790, 9,101,506, 9,364,314, 9,554,929, and 10,299,951, and U.S. patent application Ser. No. 16/413,916 (Publication No.: 2019/0269539), are incorporated by reference in their entirety.

What is claimed is:

1. A delivery device (10), comprising:
   a) a handle body (20), having a longitudinal axis (22), a proximal end (24), and a distal end (26);
   b) a gear rack (106) extending within the handle body (20);
   c) a proximal handle (36) extending about the gear rack (106) and defining teeth (156), the proximal handle (36) being rotatable about the handle body (20) and the gear rack (106);
   d) a distal handle (40) that extends around the handle body (20) at the distal end (26) of the handle body (20);
   e) a guidewire catheter (12) having a proximal end (14) and a distal end (16), the guidewire catheter (12) extending through the handle body (20), the proximal handle (36), and the distal handle (40), and along the longitudinal axis (22);
   f) a delivery catheter (28) axially fixed to the proximal handle (36), and having a distal end (30) extending from within the distal end (26) of the handle body (20) and about the guidewire catheter (12);
   g) an outer catheter (48) extending distally from the distal handle (40), and about the delivery catheter (28) when the delivery catheter (28) is in a first, retracted position;
   h) a gear assembly linking the teeth (156) of the proximal handle (36) to the gear rack (106), whereby rotation of the proximal handle (36) about the longitudinal axis (22) moves the proximal handle (36) and the delivery catheter (28) along the longitudinal axis (22) relative to the gear rack (106);
   i.) the gear assembly further including:
      1) A pinion gear assembly (164) engaging the gear rack (106); and
      2) a linking gear assembly (158) including an upper linking gear (160) engaging the teeth (156) of the proximal handle (36) and a lower linking gear (162) fixed to the upper linking gear (160) and between the upper linking gear (160) and the longitudinal axis (22) of the handle body (20), and having teeth engaging the pinion gear assembly (164), the upper linking gear (166) and the lower linking gear (162) having a common axis of rotation that is normal to the longitudinal axis (22) of the handle body (20), wherein the upper linking gear (160) and the lower linking gear (162) each define a central opening along the common axis of rotation;
i) a clutch at the gear assembly, whereby the clutch engages the gear assembly with the proximal handle and thereby biases longitudinal movement of the gear assembly and associated rotation of the proximal handle (36) about the longitudinal axis;
wherein rotation of the proximal handle (36) about the longitudinal axis (22) when the clutch is engaged is resisted by friction between the clutch and at least one of the gear assembly and a portion of the remainder of the delivery device (10), and
wherein the clutch engages when the gear assembly is directed in a proximal direction along the longitudinal axis;
j) a push rod (32) extending about the guidewire catheter (12) and within the delivery catheter (28), the push rod (32) being fixed to the guidewire catheter (12) at the proximal end of the guidewire catheter (12) proximal to the handle body (20), and selectively fixed to the proximal handle (36); and
k) a locking mechanism assembly extending about the push rod, the locking mechanism including
  i.) a first locking mechanism (38) that locks the delivery catheter to the push rod when the locking mechanism is in a first locking position, and
  ii.) a second locking mechanism (132) fixed to the distal end (26) of the handle body (20) that locks the push rod (32) to the handle body (20) when the locking mechanism assembly is in a second locking position, wherein the first locking position and the second locking position are mutually exclusive
l.) An actuator (80) that includes the gear assembly and which further includes
  i.) a housing (81) extending about the handle body (20) and having a proximal end defining a proximal opening and a distal end defining a distal opening, the housing (81) further defining an aperture between the proximal opening and the distal opening; and
  ii.) a center pin extending through the central openings of the upper linking gear (160) and the lower linking gear (162), the pin including the center pin including opposite ends that are at the locking mechanism assembly and the housing (81), wherein the clutch selectively engages the pin with the linking gear assembly whereby engagement depends upon the direction of rotation of the proximal handle (36) about the handle body (20);
m) wherein the linking gear assembly (158) further includes a second clutch that engages the linking gear assembly (158) with the pin when the pinion gear assembly 164) is directed distally along the gear rack (106) during the engagement of the linking gear assembly (158) with the pinion gear assembly (164);
n) wherein the second clutch is a second one-way needle roller clutch bearing that is press-fit into a first socket or a second socket into which the pin extends, whereby the second one-way needle roller clutch bearing engages the linking gear assembly (158) with the pin when the pinion gear assembly (163) is directed proximally along the gear rack (106) during engagement of the linking gear assembly (158) with the pinion gear assembly (164), and wherein resistance to proximal movement of the pinion gear assembly while the second one-way needle roller clutch is engaged is caused by at least one of resistance to rotation of the second roller needle clutch bearing within the socket within which the one-way needle roller bearing is press-fit or the interface between the pin and the second one-way needle roller clutch, and wherein the resistance is less than that between the first roller needle clutch and the pin.

2. The delivery device of claim 1, wherein the gear assembly includes a pinion gear assembly (164) that includes
  a) an upper pinion gear (166) engaged with the proximal handle (36), the upper pinion gear (166) defining a non-circular pinion gear orifice (182) and rotatable about a pinion gear axis (269); and
  b) a lower pinion gear (168) axially aligned with the upper pinion gear (166) and defining a lower pinion gear orifice (263), the lower pinion gear (168) engaged with the gear rack (106) and selectively engaged with the upper pinion gear (166), wherein the clutch (260) engages the lower pinion gear (168) when the gear assembly is directed in a proximal direction.

3. The delivery device of claim 2, wherein the lower pinion gear (168) includes
  a. a lower portion extending toward the longitudinal axis (22) of the handle body (20);
  b. a gear portion engaged with the gear rack (106);
  c. a pinion gear extension (265) that extends within the upper pinion gear orifice (182), wherein the pinion gear extension (265) defines a side opening (180), the side opening (180) and the upper pinion gear orifice (182) of the upper pinion gear (166) together defining an interference opening (183) that, when occupied, prevents rotation of the upper pinion gear (166) and the lower pinion gear (168) relative to each other;
  d. a ball bearing (178) in at least one of each side opening (180), the ball bearing (178) having a diameter greater than a thickness of a wall defining the side opening (180);
  e. a center pin (170) moveable along the pinion gear axis and within the upper pinion gear orifice, the lower pinion gear orifice, and the pinion gear extension orifice, the center pin (170) including a frustoconical portion (176) between a base portion having a first diameter within the lower pinion gear orifice and a second diameter that is less than the first diameter, and located in the upper pinion gear orifice, whereby movement of the frustoconical portion (176) of the center pin (170) causes radially outward displacement of the ball bearing (178) into the interference opening (183), thereby causing an interfering relation between rotation of the upper pinion gear (166) and the lower pinion gear (168); and
  f. a spring (184) at the lower pinion gear (168) that provides bias to the center pin (170) radially outward from the longitudinal axis (22) of the handle body (20), whereby the ball bearing (178) is directed radially outward through the side opening (180), thereby causing the interfering relation between the upper pinion gear (166) and the lower pinion gear (168), whereby depressing the center pin (170) removes outward displacement of the ball bearing (178) and eliminates the interfering relation between rotation of the upper pinion gear (166) and the lower pinion gear (168) to cause rotation of the proximal handle (36) to be independent of longitudinal movement of the delivery catheter (28) relative to the handle body (20) along the longitudinal axis (22).

4. The delivery devise of claim 1, wherein the pin is integral to or fused with at least one of the locking mechanism assembly and the housing (81).

5. The delivery device of claim 1, wherein the first locking mechanism (38) defines a first socket (174) and the housing (81) defines a second socket, and wherein the opposite ends of the pin are seated in the first socket (174) and the second socket.

6. The delivery device of claim 5, wherein the clutch engages the pin when the gear assembly is directed in a proximal direction.

7. The delivery device of claim 6, wherein rotation of the proximal handle (20) that directs the gear assembly in a proximal direction is resisted by an interfering relationship between the pin and at least one of the first and the second sockets.

8. The delivery device of claim 6, wherein rotation of the proximal handle (20) that directs the gear assembly in a proximal direction is resisted by an interfering relationship between the clutch and at least one of the first and the second sockets.

9. The delivery device of claim 6, wherein rotation of the proximal handle (20) that directs the gear assembly in a proximal direction is resisted by an interfering relationship between the clutch and the pin.

10. The delivery device of claim 1, wherein the second clutch is a coil spring that is fixed at one end to the first locking mechanism (38) and the pin extends through the coil spring, whereby the coil spring is engaged with the pin when the pinion gear assembly (164) is directed distally along the gear rack (106) during engagement of the linking gear assembly (158) with the pinion gear assembly (164).

11. The delivery device of claim 1, wherein the second clutch is a coil spring that is fixed at one end to the housing (81) and the pin extends through the coil spring, whereby the coil spring is engaged with the pin when the pinion gear assembly (164) is directed distally along the gear rack (106) during engagement of the linking gear assembly (158) with the pinion gear assembly (164).

12. A delivery device (10), comprising:
  a. a handle body (20), having a longitudinal axis (22), a proximal end (24), and a distal end (26);
  b. a gear rack (106) extending within the handle body (20);
  c. a proximal handle (36) extending about the gear rack (106) and defining teeth (156), the proximal handle (36) being rotatable about the handle body (20) and the gear rack (106);
  d. a distal handle (40) that extends around the handle body (20) at the distal end (26) of the handle body (20);
  e. a guidewire catheter (12) having a proximal end (14) and a distal end (16), the guidewire catheter (12) extending through the handle body (20), the proximal handle (36), the distal handle (40), and along the longitudinal axis (22);
  f. a delivery catheter (28) axially fixed to the proximal handle (36), and having a distal end (30) extending from within the distal end (26) of the handle body (20) and about the guidewire catheter (12);
  g. an outer catheter (48) extending distally from the distal handle (40), and about the delivery catheter (28) in a first, retracted position;
  h. a gear assembly linking the teeth (156) of the proximal handle (36) to the gear rack (106), whereby rotation of the proximal handle (36) about the longitudinal axis (22) moves the proximal handle (36) and the delivery catheter (28) along the longitudinal axis (22) relative to the gear rack (106), wherein the gear assembly includes
    i. A pinion gear assembly (164) engaging the gear rack (106), and
    ii. a linking gear assembly (158) including an upper linking gear (160) engaging the teeth (156) of the proximal handle (36) and a lower linking gear (162) fixed to the upper linking gear (160) and between the upper linking gear (160) and the longitudinal axis (22) of the handle body (20), and having teeth engaging the pinion gear assembly (164), the upper linking gear (166) and the lower linking gear (162) having a common axis of rotation that is normal to the longitudinal axis (22) of the handle body (20), wherein the upper linking gear (160) and the lower linking gear (162) each define a central opening along the common axis of rotation;
  i. a push rod (32) extending about the guidewire catheter (12) and within the delivery catheter (28), the push rod (32) being fixed to the guidewire catheter (12) at the proximal end of the guidewire catheter (12) proximal to the handle body (20), and selectively fixed to the proximal handle (36);
  j. a locking mechanism assembly extending about the push rod, the locking mechanism including
    i. a first locking mechanism (38) that locks the delivery catheter to the push rod when the locking mechanism is in a first locking position, wherein the first locking mechanism (38) defines a first socket (174) and the housing (81) defines a second socket, and wherein the opposite ends of the pin are seated in the first socket (174) and the second socket, and
    ii. a second locking mechanism (132) fixed to the distal end (26) of the handle body (20) that locks the push rod (32) to the handle body (20) when the locking mechanism assembly is in a second locking position, wherein the first locking position and the second locking position are mutually exclusive;
  k. an actuator (80) that includes the gear assembly and which further includes
    i. a housing (81) extending about the handle body (20) and having a proximal end defining a proximal opening and a distal end defining a distal opening, the housing (81) further defining an aperture between the proximal opening and the distal opening, and
    ii. a center pin extending through the central openings of the upper linking gear (160) and the lower linking gear (162), the pin including opposite ends that are at the locking mechanism assembly and the housing (81); and
  l. A clutch at the gear assembly, whereby the clutch engages the gear assembly with the proximal handle and thereby biases longitudinal movement of the gear assembly and associated rotation of the proximal handle (36) about the longitudinal axis, wherein rotation of the proximal handle (36) about the longitudinal axis (22) when the clutch is engaged is resisted by friction between the clutch and at least one of the gear assembly and a portion of the remainder of the delivery device (10), wherein the clutch engages the pin with the linking gear assembly when the gear assembly is directed in a proximal direction, and wherein rotation of the proximal handle (20) that directs the gear assembly in a proximal direction is resisted by an interfering relationship between the pin and at least one of the first and the second sockets;

m. wherein the linking gear assembly (158) further includes a second clutch that engages the linking gear assembly (158) with the pin when the pinion gear assembly (164) is directed distally along the gear rack (106) during the engagement of the linking gear assembly (158) with the pinion gear assembly (164), wherein the second clutch is a second one-way needle roller clutch bearing that is press-fit into the first socket or the second socket into which the pin extends, whereby the second one-way needle roller clutch bearing engages the linking gear assembly (158) with the pin when the pinion gear assembly (163) is directed proximally along the gear rack (106) during engagement of the linking gear assembly (158) with the pinion gear assembly (164), and wherein resistance to proximal movement of the pinion gear assembly while the second one-way needle roller clutch is engaged is caused by at least one of resistance to rotation of the second roller needle clutch bearing within the socket within which the one-way needle roller bearing is press-fit or the interface between the pin and the second one-way needle roller clutch, and wherein the resistance is less than that between the first roller needle clutch and the pin.

* * * * *